United States Patent
Morton et al.

(10) Patent No.: US 9,751,932 B2
(45) Date of Patent: Sep. 5, 2017

(54) ANTI-BIG-ENDOTHELIN-1 (BIG-ET-1) ANTIBODIES AND USES THEREOF

(71) Applicant: Regeneron Pharmaceuticals, Inc., Tarrytown, NY (US)

(72) Inventors: Lori C. Morton, Chappaqua, NY (US); Douglas MacDonald, New York, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 166 days.

(21) Appl. No.: 13/774,695

(22) Filed: Feb. 22, 2013

(65) Prior Publication Data
US 2013/0216547 A1 Aug. 22, 2013

Related U.S. Application Data

(60) Provisional application No. 61/601,622, filed on Feb. 22, 2012, provisional application No. 61/677,024, filed on Jul. 30, 2012.

(51) Int. Cl.
| | | |
|---|---|---|
| C07K 16/22 | (2006.01) | |
| C07K 16/24 | (2006.01) | |
| C07K 16/26 | (2006.01) | |
| A61K 39/395 | (2006.01) | |
| C07K 16/18 | (2006.01) | |
| A61K 39/00 | (2006.01) | |

(52) U.S. Cl.
CPC .......... *C07K 16/18* (2013.01); *C07K 16/26* (2013.01); *A61K 2039/505* (2013.01); *C07K 2317/52* (2013.01); *C07K 2317/76* (2013.01)

(58) Field of Classification Search
None
See application file for complete search history.

(56) References Cited

U.S. PATENT DOCUMENTS

2013/0096050 A1* 4/2013 Shandler .......... C07K 14/57563
514/1.7

FOREIGN PATENT DOCUMENTS

| EP | 0331100 A1 | 9/1989 |
| EP | 0384144 A1 | 8/1990 |
| EP | 0406628 B1 | 11/1994 |
| WO | WO 2011/133948 A2 | 10/2011 |
| WO | WO 2013/126740 A1 | 8/2013 |

OTHER PUBLICATIONS

Susuki et al. Sandwich-enzyme immunoassays for endothelin family peptides. Journal of cardiovascular pharmacology, vol. 17 Suppl 7, pp. S420-S422 (1991).*
Aubin et al., "Sandwich-type enzyme immunoassay for big endothelin-I in plasma: concentrations in healthy human subjects unaffected by sex or posture.", Clinical Chemistry, 43(1):64-70, (1997).
Bagnato et al., "Role of the endothelin axis and its antagonists in the treatment of cancer", British Journal of Pharmacology, 163(2):220-233, (2011).
WIPO Application No. PCT/US2013/027380, PCT International Search Report and Written Opinion of the International Searching Authority mailed Jun. 6, 2013.
GenBank: AAA94499.1, "Sequence 1 from U.S. Pat. No. 546862," Nov. 21, 1995. [Retrieved from the Internet Sep. 30, 2014: <URL: http://www.ncbi.nlm.nih.gov/protein/AAA94499>].
GenBank: ABY15159.1, "Sequence 534 from U.S. Pat. No. 7,306,913," Dec. 14, 2007. [Retrieved from the Internet Sep. 30, 2014: <URL: http://www.ncbi.nlm.nih.gov/protein/ABY15159>].
GenBank: ACN03404.1, "Sequence 40 from U.S. Pat. No. 7,482,124," Feb 13, 2009. [Retrieved from the Internet Sep. 30, 2014: <URL: http://www.ncbi.nlm.nih.gov/protein/ACN03404>].
GenBank: ADS13399.1, "Sequence 36 from U.S. Pat. No. 7,754,859," Dec. 12, 2010. [Retrieved from the Internet Sep. 30, 2014: <URL: http://www.ncbi.nlm.nih.gov/protein/ADS13399>].
GenBank: AFL27095.1, "Sequence 197 from U.S. Pat. No. 8,168,588," Jun. 5, 2012. [Retrieved from the Internet Sep. 30, 2014: <URL: http://www.ncbi.nlm.nih.gov/protein/AFL27095>].
GenBank: EHH52718.1, "Preproendothelin-1 [Macaca fascicularis]," Nov. 4, 2011. [Retrieved from the Internet Sep. 30, 2014: <URL: http://www.ncbi.nlm.nih.gov/protein/EHH52718>].
NCBI Reference Sequence: XP_004043330.1, "PREDICTED: endothelin-1 [Gorilla gorilla gorilla]," Dec. 3, 2012. [Retrieved from the Internet Sep. 30, 2014: <URL: http://www.ncbi.nlm.nih.gov/protein/XP_004043330>].
NCBI Reference Sequence: XP001089874.1, "PREDICTED: endothelin-1 [Macaca mulatta]," Jun. 1 2010. [Retrieved from the Internet Sep. 30, 2014: <URL: http://www.ncbi.nlm.nih.gov/protein/XP_001089874>].
PIR: S23230. "Ig kappa chain precursor V-J region—human (fragment) [*Homo sapiens*]," Jan. 21, 2000. [Retrieved from the Internet Sep. 30, 2014: <URL: http://www.ncbi.nlm.nih.gov/protein/S23230>].
WIPO Application No. PCT/US2013/027380, PCT International Preliminary Report on Patentability mailed Sep. 4, 2014.

* cited by examiner

*Primary Examiner* — Elizabeth C Kemmerer
*Assistant Examiner* — Regina M Deberry
(74) *Attorney, Agent, or Firm* — Schwabe, Williamson & Wyatt PC; Christopher Westberg

(57) ABSTRACT

The present invention provides antibodies that bind big-endothelin-1 ("big-ET-1"), and methods of using same. According to certain embodiments of the invention, the antibodies specifically bind human big-ET-1 but do not bind human small-ET-1 (i.e., the active form of endothelin-1 that results from proteolytic cleavage of big-ET-1 by endothelin-converting enzyme-1 [ECE-1]). According to certain embodiments of the invention, the anti-big-ET-1 antibodies are capable of blocking cleavage of big-ET-1 by ECE-1. The antibodies of the invention are useful for the treatment of big-ET-1-related disorders, including hypertension disorders, fibrotic disorders, neurodegenerative disorders, retinal disorders, pain and cancers.

20 Claims, 11 Drawing Sheets ived from a ~200

SEQUENCE LISTING

```
<160> NUMBER OF SEQ ID NOS: 437

<210> SEQ ID NO 1
<211> LENGTH: 354
<212> TYPE: DNA
<213> ORGANISM: Artificial Sequence
```

<220> FEATURE:
<223> OTHER INFORMATION: Synthetic

<400> SEQUENCE: 1

```
gaggtgcagc tggtggagtc tgggggaggc ctggtcaagc ctggggggtc cctgagactc      60
tcctgtgcag cctctggatt caccttcagt agttataaca tgaactgggt ccgtcaggct     120
ccagggaagg ggctggagtg ggtctcatcc attagtagta gtagtagtta catatactac     180
gcagactcag tgaagggccg attcaccatc tccagagaca cgccaagaa ctcactgtat      240
ctgcaaatga acagcctgag agccgaggac acggctgtgt attactgtgc gagagataac     300
tggaactaca gctttgacta ctggggccag ggaaccctgg tcaccgtctc ctca           354
```

<210> SEQ ID NO 2
<211> LENGTH: 118
<212> TYPE: PRT
<213> ORGANISM: Artificial Sequence
<220> FEATURE:
<223> OTHER INFORMATION: Synthetic

<400> SEQUENCE: 2

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Asn Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Trp Asn Tyr Ser Phe Asp Tyr Trp Gly Gln Gly Thr
            100                 105                 110

Leu Val Thr Val Ser Ser
        115
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggattcacct tcagtagtta taac                                             24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Phe Thr Phe Ser Ser Tyr Asn
 1               5
```

<210> SEQ ID NO 5
<211> LENGTH: 24

```
<212> TYPE: DNA
<213> ORGANISM: Artificial Sequence
<220> FEATURE:
<223> OTHER INFORMATION: Synthetic

<400> SEQUENCE: 5
attagtagta gtagtagtta cata                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Ser Ser Ser Ser Tyr Ile
 1               5

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7
gcgagagata actggaacta cagctttgac tac                                33

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Ala Arg Asp Asn Trp Asn Tyr Ser Phe Asp Tyr
 1               5                  10

<210> SEQ ID NO 9
<211> LENGTH: 324
<212> TYPE: DNA
<213> ORGANISM: Artificial Sequence
<220> FEATURE:
<223> OTHER INFORMATION: Synthetic

<400> SEQUENCE: 9
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcagtc tcaccatcag cagactggag   240
cctgaagatt ttgcactgta ttactgtcag cagtatggta gctcaccgct cactttcggc   300
ggagggacca aggtggagat caaa                                         324

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10
```

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Ser Leu Thr Ile Ser Arg Leu Glu
 65                  70                  75                  80

Pro Glu Asp Phe Ala Leu Tyr Tyr Cys Gln Gln Tyr Gly Ser Ser Pro
                 85                  90                  95

Leu Thr Phe Gly Gly Gly Thr Lys Val Glu Ile Lys
                100                 105
```

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
cagagtgtta gcagcagcta c                                         21

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

```
Gln Ser Val Ser Ser Ser Tyr
 1               5
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ggtgcatcc                                                        9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

```
Gly Ala Ser
 1
```

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
cagcagtatg gtagctcacc gctcact    27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr Gly Ser Ser Pro Leu Thr
 1               5

<210> SEQ ID NO 17
<211> LENGTH: 366
<212> TYPE: DNA
<213> ORGANISM: Artificial Sequence
<220> FEATURE:
<223> OTHER INFORMATION: Synthetic

<400> SEQUENCE: 17
gaagtgcagt tgttggagtc tgggggggc ttggtacagc ctgggggtc cctgagactc    60 tcctgtgcag cctctggatt cacctttagc agctatgcca tgacctgggt ccgccaggct    120
ccagggaagg ggctggagtg catctcagct attagtggca gtggttatag cacatactac    180
gcagactcca tgaagggccg gttctccatc tccagagaca attccaagaa cacgctgtat    240
ctgcaaatga accgcctgag agccgaggac acggccgttt attactgtac gaaagggggc    300
cgaattttgg agtggttatt acctttgac ttctggggcc agggaaccct ggtcaccgtc    360
tcctca    366

<210> SEQ ID NO 18
<211> LENGTH: 122
<212> TYPE: PRT
<213> ORGANISM: Artificial Sequence
<220> FEATURE:
<223> OTHER INFORMATION: Synthetic

<400> SEQUENCE: 18

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Thr Trp Val Arg Gln Ala Pro Gly Lys Gly Leu Glu Cys Ile
         35                  40                  45

Ser Ala Ile Ser Gly Ser Gly Tyr Ser Thr Tyr Tyr Ala Asp Ser Met
     50                  55                  60

Lys Gly Arg Phe Ser Ile Ser Arg Asp Asn Ser Lys Asn Thr Leu Tyr
 65                  70                  75                  80

Leu Gln Met Asn Arg Leu Arg Ala Glu Asp Thr Ala Val Tyr Tyr Cys
                 85                  90                  95

Thr Lys Gly Gly Arg Ile Leu Glu Trp Leu Leu Pro Phe Asp Phe Trp
            100                 105                 110

Gly Gln Gly Thr Leu Val Thr Val Ser Ser
        115                 120

<210> SEQ ID NO 19
<211> LENGTH: 24
<212> TYPE: DNA

```
<213> ORGANISM: Artificial Sequence
<220> FEATURE:
<223> OTHER INFORMATION: Synthetic

<400> SEQUENCE: 19
ggattcacct ttagcagcta tgcc                                              24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Ser Ser Tyr Ala
 1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
attagtggca gtggttatag caca                                              24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Ser Gly Ser Gly Tyr Ser Thr
 1               5

<210> SEQ ID NO 23
<211> LENGTH: 45
<212> TYPE: DNA
<213> ORGANISM: Artificial Sequence
<220> FEATURE:
<223> OTHER INFORMATION: Synthetic

<400> SEQUENCE: 23
acgaaagggg gccgaatttt ggagtggtta ttaccctttg acttc                       45

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Thr Lys Gly Gly Arg Ile Leu Glu Trp Leu Leu Pro Phe Asp Phe
 1               5                  10                  15

<210> SEQ ID NO 25
<211> LENGTH: 336
<212> TYPE: DNA
<213> ORGANISM: Artificial Sequence
<220> FEATURE:
<223> OTHER INFORMATION: Synthetic
```

<400> SEQUENCE: 25

```
gatgttgtga tgactcagtc tccactctcc ctgcccgtca cccttggaca gccggcctcc    60
atctcctgcc ggtctagtca aagcctcgta tacagtgatg gaaacaccta cttgatttgg   120
tttcagcaga ggccaggcca atctccaagg cgcctaattt ataaggtttc taaccgggac   180
tctggggtcc cagacagatt cagcggcagt gggtcaggca ctgatttcac actgataatc   240
agcagggtgg aggctgagga tgttgggctt tattactgca tgcaaggtac acactggcct   300
cctactttcg gcggagggac caaggtggag atcaaa                             336
```

<210> SEQ ID NO 26
<211> LENGTH: 112
<212> TYPE: PRT
<213> ORGANISM: Artificial Sequence
<220> FEATURE:
<223> OTHER INFORMATION: Synthetic

<400> SEQUENCE: 26

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30

Asp Gly Asn Thr Tyr Leu Ile Trp Phe Gln Gln Arg Pro Gly Gln Ser
         35                  40                  45

Pro Arg Arg Leu Ile Tyr Lys Val Ser Asn Arg Asp Ser Gly Val Pro
     50                  55                  60

Asp Arg Phe Ser Gly Ser Gly Ser Gly Thr Asp Phe Thr Leu Ile Ile
 65                  70                  75                  80

Ser Arg Val Glu Ala Glu Asp Val Gly Leu Tyr Tyr Cys Met Gln Gly
                 85                  90                  95

Thr His Trp Pro Pro Thr Phe Gly Gly Gly Thr Lys Val Glu Ile Lys
            100                 105                 110
```

<210> SEQ ID NO 27
<211> LENGTH: 33
<212> TYPE: DNA
<213> ORGANISM: Artificial Sequence
<220> FEATURE:
<223> OTHER INFORMATION: Synthetic

<400> SEQUENCE: 27

```
caaagcctcg tatacagtga tggaaacacc tac                                 33
```

<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

```
Gln Ser Leu Val Tyr Ser Asp Gly Asn Thr Tyr
 1               5                  10
```

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 aaggtttct                                                                                    9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Lys Val Ser
 1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
atgcaaggta cacactggcc tcctact                                                                27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Met Gln Gly Thr His Trp Pro Pro Thr
 1               5

<210> SEQ ID NO 33
<211> LENGTH: 345
<212> TYPE: DNA
<213> ORGANISM: Artificial Sequence
<220> FEATURE:
<223> OTHER INFORMATION: Synthetic

<400> SEQUENCE: 33
gaggtgcagc tggtggagtc tgggggaggc ttggtaaagc ctggggggtc ccttagagtc          60
tcctgtgtag cctctggatt cacttttagt aacgcctgga tgacctgggt ccgccagact         120
ccagggaagg ggctggagtg cgttggccgt attaaaagca gaactgatgg tgggacagtt         180
gactatgttg cacccgtgaa aggcagattc accatctcaa gagatgattc aaaaaacacg         240
ctgtatctgc aaatgaacag cctgaaagcc gaggacacag ccgtttatta ctgtagggct         300
gaccttgact actggggcca gggaaccctg gtcaccgttt cctca                        345

<210> SEQ ID NO 34
<211> LENGTH: 115
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Val Lys Pro Gly Gly
 1               5                  10                  15

Ser Leu Arg Val Ser Cys Val Ala Ser Gly Phe Thr Phe Ser Asn Ala
            20                  25                  30

Trp Met Thr Trp Val Arg Gln Thr Pro Gly Lys Gly Leu Glu Cys Val
            35                  40                  45

Gly Arg Ile Lys Ser Arg Thr Asp Gly Gly Thr Val Asp Tyr Val Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Ala Glu Asp Thr Ala Val Tyr
                85                  90                  95

Tyr Cys Arg Ala Asp Leu Asp Tyr Trp Gly Gln Gly Thr Leu Val Thr
            100                 105                 110

Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcactt ttagtaacgc ctgg                                          24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Ser Asn Ala Trp
1               5

<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37
attaaaagca gaactgatgg tgggacagtt                                    30

<210> SEQ ID NO 38
<211> LENGTH: 10
<212> TYPE: PRT
<213> ORGANISM: Artificial Sequence
<220> FEATURE:
<223> OTHER INFORMATION: Synthetic

<400> SEQUENCE: 38

Ile Lys Ser Arg Thr Asp Gly Gly Thr Val
1               5                   10

<210> SEQ ID NO 39
<211> LENGTH: 18
<212> TYPE: DNA
<213> ORGANISM: Artificial Sequence
<220> FEATURE:
<223> OTHER INFORMATION: Synthetic

<400> SEQUENCE: 39
agggctgacc ttgactac                                                 18

<210> SEQ ID NO 40
<211> LENGTH: 6
<212> TYPE: PRT
<213> ORGANISM: Artificial Sequence
<220> FEATURE:
<223> OTHER INFORMATION: Synthetic

<400> SEQUENCE: 40

Arg Ala Asp Leu Asp Tyr
 1               5

<210> SEQ ID NO 41
<211> LENGTH: 336
<212> TYPE: DNA
<213> ORGANISM: Artificial Sequence
<220> FEATURE:
<223> OTHER INFORMATION: Synthetic

<400> SEQUENCE: 41
gatgttgtga tgactcagtc tccactctcc ctgcccgtct cccttggaca gccggcctcc      60
atctcctgca ggtctagtca aagcctcgta cacagtgatg gaatcaccta cttgaattgg     120
tttcagcaga ggccaggcca atctccaagg cgcctaattt ataagatttc taaccgggac     180
tctggggtcc cagacagatt cagcggcagt gggtcaggca ctgatttcac actgaaattc     240
agcagggtgg aggctgagga tgttggggtt tatttctgca tgcaaggtac acactggccg     300 tacactttg gccaggggac caagctggag atcaaa                                336

<210> SEQ ID NO 42
<211> LENGTH: 112
<212> TYPE: PRT
<213> ORGANISM: Artificial Sequence
<220> FEATURE:
<223> OTHER INFORMATION: Synthetic

<400> SEQUENCE: 42

Asp Val Val Met Thr Gln Ser Pro Leu Ser Leu Pro Val Ser Leu Gly
 1               5                  10                  15

Gln Pro Ala Ser Ile Ser Cys Arg Ser Ser Gln Ser Leu Val His Ser
             20                  25                  30

Asp Gly Ile Thr Tyr Leu Asn Trp Phe Gln Gln Arg Pro Gly Gln Ser
         35                  40                  45

Pro Arg Arg Leu Ile Tyr Lys Ile Ser Asn Arg Asp Ser Gly Val Pro
     50                  55                  60

Asp Arg Phe Ser Gly Ser Gly Ser Gly Thr Asp Phe Thr Leu Lys Phe
 65                  70                  75                  80

Ser Arg Val Glu Ala Glu Asp Val Gly Val Tyr Phe Cys Met Gln Gly
                 85                  90                  95

Thr His Trp Pro Tyr Thr Phe Gly Gln Gly Thr Lys Leu Glu Ile Lys
            100                 105                 110

<210> SEQ ID NO 43
<211> LENGTH: 33
<212> TYPE: DNA
<213> ORGANISM: Artificial Sequence
<220> FEATURE:
<223> OTHER INFORMATION: Synthetic

<400> SEQUENCE: 43
caaagcctcg tacacagtga tggaatcacc tac                                   33

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

Gln Ser Leu Val His Ser Asp Gly Ile Thr Tyr
 1               5                  10

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 aagatttct                                                            9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Lys Ile Ser
 1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
atgcaaggta cacactggcc gtacact                                       27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Met Gln Gly Thr His Trp Pro Tyr Thr
 1               5

<210> SEQ ID NO 49
<211> LENGTH: 345
<212> TYPE: DNA
<213> ORGANISM: Artificial Sequence
<220> FEATURE:
<223> OTHER INFORMATION: Synthetic

<400> SEQUENCE: 49
gaggtgcagc tggtggagtc tgggggaggc ttggtaaagc ctggggggtc ccttagagtc      60
tcctgtgtag cctctggatt cacttttagt aacgcctgga tgacctgggt ccgccagact     120
ccagggaagg ggctggagtg cgttggccgt attaaaagca gaactgatgg tgggacagtt     180

```
gactatgttg acccgtgaa aggcagattc accatctcaa gagatgattc aaaaaacacg    240
ctgtatctgc aaatgaacag cctgaaagcc gaggacacag ccgtttatta ctgtagggct    300
gaccttgact actggggcca gggaaccctg gtcaccgttt cctca                   345
```

<210> SEQ ID NO 50
<211> LENGTH: 115
<212> TYPE: PRT
<213> ORGANISM: Artificial Sequence
<220> FEATURE:
<223> OTHER INFORMATION: Synthetic

<400> SEQUENCE: 50

```
Glu Val Gln Leu Val Glu Ser Gly Gly Gly Leu Val Lys Pro Gly Gly
 1               5                  10                  15
Ser Leu Arg Val Ser Cys Val Ala Ser Gly Phe Thr Phe Ser Asn Ala
            20                  25                  30
Trp Met Thr Trp Val Arg Gln Thr Pro Gly Lys Gly Leu Glu Cys Val
        35                  40                  45
Gly Arg Ile Lys Ser Arg Thr Asp Gly Gly Thr Val Asp Tyr Val Ala
    50                  55                  60
Pro Val Lys Gly Arg Phe Thr Ile Ser Arg Asp Asp Ser Lys Asn Thr
65                  70                  75                  80
Leu Tyr Leu Gln Met Asn Ser Leu Lys Ala Glu Asp Thr Ala Val Tyr
                85                  90                  95
Tyr Cys Arg Ala Asp Leu Asp Tyr Trp Gly Gln Gly Thr Leu Val Thr
            100                 105                 110
Val Ser Ser
        115
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggattcactt ttagtaacgc ctgg                                          24
```

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

```
Gly Phe Thr Phe Ser Asn Ala Trp
 1               5
```

<210> SEQ ID NO 53
<211> LENGTH: 30
<212> TYPE: DNA
<213> ORGANISM: Artificial Sequence
<220> FEATURE:
<223> OTHER INFORMATION: Synthetic

<400> SEQUENCE: 53

```
attaaaagca gaactgatgg tgggacagtt                                    30
```

<210> SEQ ID NO 54

```
<211> LENGTH: 10
<212> TYPE: PRT
<213> ORGANISM: Artificial Sequence
<220> FEATURE:
<223> OTHER INFORMATION: Synthetic

<400> SEQUENCE: 54

Ile Lys Ser Arg Thr Asp Gly Gly Thr Val
1               5                   10

<210> SEQ ID NO 55
<211> LENGTH: 18
<212> TYPE: DNA
<213> ORGANISM: Artificial Sequence
<220> FEATURE:
<223> OTHER INFORMATION: Synthetic

<400> SEQUENCE: 55
agggctgacc ttgactac                                                   18

<210> SEQ ID NO 56
<211> LENGTH: 6
<212> TYPE: PRT
<213> ORGANISM: Artificial Sequence
<220> FEATURE:
<223> OTHER INFORMATION: Synthetic

<400> SEQUENCE: 56

Arg Ala Asp Leu Asp Tyr
1               5

<210> SEQ ID NO 57
<211> LENGTH: 336
<212> TYPE: DNA
<213> ORGANISM: Artificial Sequence
<220> FEATURE:
<223> OTHER INFORMATION: Synthetic

<400> SEQUENCE: 57
gatgttgtga tgactcagtc tccactctcc ctgcccgtct cccttggaca gccggcctcc     60
atctcctgca ggtctagtca aagcctcgta cacagtgatg gaatcaccta cttgaattgg    120
tttcagcaga ggccaggcca atctccaagg cgcctaattt ataagatttc taaccgggac    180
tctggggtcc cagacagatt cagcggcagt gggtcaggca ctgatttcac actgaaattc    240
agcagggtgg aggctgagga tgttggggtt tatttctgca tgcaaggtac acactggccg    300 tacactttg gccaggggac caagctggag atcaaa                               336

<210> SEQ ID NO 58
<211> LENGTH: 112
<212> TYPE: PRT
<213> ORGANISM: Artificial Sequence
<220> FEATURE:
<223> OTHER INFORMATION: Synthetic

<400> SEQUENCE: 58

Asp Val Val Met Thr Gln Ser Pro Leu Ser Leu Pro Val Ser Leu Gly
1               5                   10                  15

Gln Pro Ala Ser Ile Ser Cys Arg Ser Ser Gln Ser Leu Val His Ser
            20                  25                  30

Asp Gly Ile Thr Tyr Leu Asn Trp Phe Gln Gln Arg Pro Gly Gln Ser
        35                  40                  45

Pro Arg Arg Leu Ile Tyr Lys Ile Ser Asn Arg Asp Ser Gly Val Pro
    50                  55                  60
```

Asp Arg Phe Ser Gly Ser Gly Ser Gly Thr Asp Phe Thr Leu Lys Phe
65                  70                  75                  80

Ser Arg Val Glu Ala Glu Asp Val Gly Val Tyr Phe Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 59
<211> LENGTH: 33
<212> TYPE: DNA
<213> ORGANISM: Artificial Sequence
<220> FEATURE:
<223> OTHER INFORMATION: Synthetic

<400> SEQUENCE: 59
caaagcctcg tacacagtga tggaatcacc tac                                    33

<210> SEQ ID NO 60
<211> LENGTH: 11
<212> TYPE: PRT
<213> ORGANISM: Artificial Sequence
<220> FEATURE:
<223> OTHER INFORMATION: Synthetic

<400> SEQUENCE: 60

Gln Ser Leu Val His Ser Asp Gly Ile Thr Tyr
 1               5                  10

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 aagatttct                                                               9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Lys Ile Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
atgcaaggta cacactggcc gtacact                                           27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Met Gln Gly Thr His Trp Pro Tyr Thr
1               5

<210> SEQ ID NO 65
<211> LENGTH: 363
<212> TYPE: DNA
<213> ORGANISM: Artificial Sequence
<220> FEATURE:
<223> OTHER INFORMATION: Synthetic

<400> SEQUENCE: 65

```
caggtgcagc tggtggagtc tgggggaggc gtggtccagc ctggggaggtc cctgagactc    60
tcctgtgcag cgtctggatt caccttcaga agctatggca tgcactgggt ccgccaggct   120
ccaggcaagg ggctggagtg ggtggcagtt atatggtatg atggaagtga taaatactat   180
gcagactccg tgaagggccg attcaccatc tccagagaca attccaagaa cacgctgtat   240
ctgcaaatga acagcctgag agccgaggac acggctgttt atttctgtgc gaaagatgaa   300
tataagacca gggcggcta ctttgactac tggggccagg gaaccctggt caccgtctcc   360
tca                                                                363
```

<210> SEQ ID NO 66
<211> LENGTH: 121
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Glu Tyr Lys Thr Arg Gly Gly Tyr Phe Asp Tyr Trp Gly
            100                 105                 110

Gln Gly Thr Leu Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67

```
ggattcacct tcagaagcta tggc                                           24
```

<210> SEQ ID NO 68
<211> LENGTH: 8

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Arg Ser Tyr Gly
1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
atatggtatg atggaagtga taaa                                              24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ile Trp Tyr Asp Gly Ser Asp Lys
1               5

<210> SEQ ID NO 71
<211> LENGTH: 42
<212> TYPE: DNA
<213> ORGANISM: Artificial Sequence
<220> FEATURE:
<223> OTHER INFORMATION: Synthetic

<400> SEQUENCE: 71
gcgaaagatg aatataagac caggggcggc tactttgact ac                          42

<210> SEQ ID NO 72
<211> LENGTH: 14
<212> TYPE: PRT
<213> ORGANISM: Artificial Sequence
<220> FEATURE:
<223> OTHER INFORMATION: Synthetic

<400> SEQUENCE: 72

Ala Lys Asp Glu Tyr Lys Thr Arg Gly Gly Tyr Phe Asp Tyr
1               5                   10

<210> SEQ ID NO 73
<211> LENGTH: 336
<212> TYPE: DNA
<213> ORGANISM: Artificial Sequence
<220> FEATURE:
<223> OTHER INFORMATION: Synthetic

<400> SEQUENCE: 73
gatgttgtga tgactcagtc tccactctcc ctgcccgtca cccttggaca gccggcctcc       60
atctcctgca ggtctagtca agcctcgta tacagtgatg aaacaccta cttgaattgg       120 tttcaacaga ggccaggcca atctccaagg cgcctaattt ataaggtttc taaccgggac      180
tctggggtcc cagacagatt cagcggcagt gggtcaggca ctgatttcac actgaaaatc      240
agcagggtgg aggctgagga tgttggggtt tattactgca tgcaaggtac acactggcct      300

-continued

```
cccactttg gccaggggac caaactggag atcaaa                                  336
```

<210> SEQ ID NO 74
<211> LENGTH: 112
<212> TYPE: PRT
<213> ORGANISM: Artificial Sequence
<220> FEATURE:
<223> OTHER INFORMATION: Synthetic
<400> SEQUENCE: 74

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Leu Glu Ile Lys
            100                 105                 110
```

<210> SEQ ID NO 75
<211> LENGTH: 33
<212> TYPE: DNA
<213> ORGANISM: Artificial Sequence
<220> FEATURE:
<223> OTHER INFORMATION: Synthetic
<400> SEQUENCE: 75

```
caaagcctcg tatacagtga tggaaacacc tac                                     33
```

<210> SEQ ID NO 76
<211> LENGTH: 11
<212> TYPE: PRT
<213> ORGANISM: Artificial Sequence
<220> FEATURE:
<223> OTHER INFORMATION: Synthetic
<400> SEQUENCE: 76

```
Gln Ser Leu Val Tyr Ser Asp Gly Asn Thr Tyr
 1               5                  10
```

<210> SEQ ID NO 77
<211> LENGTH: 9
<212> TYPE: DNA
<213> ORGANISM: Artificial Sequence
<220> FEATURE:
<223> OTHER INFORMATION: Synthetic
<400> SEQUENCE: 77

```
aaggtttct                                                                 9
```

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Lys Val Ser
 1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
atgcaaggta cacactggcc tcccact                                         27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Met Gln Gly Thr His Trp Pro Pro Thr
 1               5

<210> SEQ ID NO 81
<211> LENGTH: 363
<212> TYPE: DNA
<213> ORGANISM: Artificial Sequence
<220> FEATURE:
<223> OTHER INFORMATION: Synthetic

<400> SEQUENCE: 81
caggtgcagc tggtggagtc tgggggaggc gtggtccagc ctgggaggtc cctgagactc      60
tcctgtgcag cgtctggatt caccttcaga agctatggca tgcactgggt ccgccaggct     120
ccaggcaagg ggctggagtg ggtggcagtt atatggtatg atggaagtga taaatactat     180
gcagactccg tgaagggccg attcaccatc tccagagaca attccaagaa cacgctgtat     240
ctgcaaatga acagcctgag agccgaggac acggctgttt atttctgtgc gaaagatgaa     300
tataagacca ggggcggcta ctttgactac tggggccagg gaaccctggt caccgtctcc     360
tca                                                                  363

<210> SEQ ID NO 82
<211> LENGTH: 121
<212> TYPE: PRT
<213> ORGANISM: Artificial Sequence
<220> FEATURE:
<223> OTHER INFORMATION: Synthetic

<400> SEQUENCE: 82

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Arg Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asp Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

```
Leu Gln Met Asn Ser Leu Arg Ala Glu Asp Thr Ala Val Tyr Phe Cys
                 85                  90                  95
Ala Lys Asp Glu Tyr Lys Thr Arg Gly Gly Tyr Phe Asp Tyr Trp Gly
            100                 105                 110
Gln Gly Thr Leu Val Thr Val Ser Ser
        115                 120
```

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcacct tcagaagcta tggc                                          24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

```
Gly Phe Thr Phe Arg Ser Tyr Gly
  1               5
```

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
atatggtatg atggaagtga taaa                                          24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

```
Ile Trp Tyr Asp Gly Ser Asp Lys
  1               5
```

<210> SEQ ID NO 87
<211> LENGTH: 42
<212> TYPE: DNA
<213> ORGANISM: Artificial Sequence
<220> FEATURE:
<223> OTHER INFORMATION: Synthetic

<400> SEQUENCE: 87
gcgaaagatg aatataagac caggggcggc tactttgact ac                      42

<210> SEQ ID NO 88
<211> LENGTH: 14
<212> TYPE: PRT
<213> ORGANISM: Artificial Sequence
<220> FEATURE:
<223> OTHER INFORMATION: Synthetic

<400> SEQUENCE: 88

Ala Lys Asp Glu Tyr Lys Thr Arg Gly Gly Tyr Phe Asp Tyr
1               5                   10

<210> SEQ ID NO 89
<211> LENGTH: 336
<212> TYPE: DNA
<213> ORGANISM: Artificial Sequence
<220> FEATURE:
<223> OTHER INFORMATION: Synthetic

<400> SEQUENCE: 89

```
gatgttgtga tgactcagtc tccactctcc ctgcccgtca cccttggaca gccggcctcc    60
atctcctgca ggtctagtca aagcctcgta tacagtgatg gaaacaccta cttgaattgg   120
tttcaacaga ggccaggcca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggcct   300 cccactttg gccagggac caaactggag atcaaa                               336
```

<210> SEQ ID NO 90
<211> LENGTH: 112
<212> TYPE: PRT
<213> ORGANISM: Artificial Sequence
<220> FEATURE:
<223> OTHER INFORMATION: Synthetic

<400> SEQUENCE: 90

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Leu Glu Ile Lys
            100                 105                 110

<210> SEQ ID NO 91
<211> LENGTH: 33
<212> TYPE: DNA
<213> ORGANISM: Artificial Sequence
<220> FEATURE:
<223> OTHER INFORMATION: Synthetic

<400> SEQUENCE: 91
caaagcctcg tatacagtga tggaaacacc tac                                 33

<210> SEQ ID NO 92
<211> LENGTH: 11
<212> TYPE: PRT
<213> ORGANISM: Artificial Sequence
<220> FEATURE:
<223> OTHER INFORMATION: Synthetic

<400> SEQUENCE: 92

```
Gln Ser Leu Val Tyr Ser Asp Gly Asn Thr Tyr
 1               5                  10
```

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 aaggtttct                                                              9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

```
Lys Val Ser
 1
```

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
atgcaaggta cacactggcc tcccact                                          27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

```
Met Gln Gly Thr His Trp Pro Pro Thr
 1               5
```

<210> SEQ ID NO 97
<211> LENGTH: 348
<212> TYPE: DNA
<213> ORGANISM: Artificial Sequence
<220> FEATURE:
<223> OTHER INFORMATION: Synthetic

<400> SEQUENCE: 97
caggtgcagc tggtggagtc tgggggaggc gtggtccagc ctggagggtc cctgagactc      60
tcctgtgcag cgtctggatt caccttcagt acctatggca tgcactgggt ccgccaggct     120
ccaggcaagg gctggagtg gtggcagtt ttttggtttg atggaagtaa taaatactat      180
gcagactccg tgaagggccg attcaccatc tccagagaca attccaagaa cactatttat     240
cttcaaatga acagcctgag agccgaggac acggctatat attactgtgc gagagcttat     300
gatgcttttg atatctgggg ccaagggaca atggtcaccg tctcttca                  348

<210> SEQ ID NO 98
<211> LENGTH: 116

```
<212> TYPE: PRT
<213> ORGANISM: Artificial Sequence
<220> FEATURE:
<223> OTHER INFORMATION: Synthetic

<400> SEQUENCE: 98

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Phe Trp Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Ile Tyr
65                  70                  75                  80

Leu Gln Met Asn Ser Leu Arg Ala Glu Asp Thr Ala Ile Tyr Tyr Cys
                85                  90                  95

Ala Arg Ala Tyr Asp Ala Phe Asp Ile Trp Gly Gln Gly Thr Met Val
            100                 105                 110

Thr Val Ser Ser
        115

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcacct tcagtaccta tggc                                          24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Thr Phe Ser Thr Tyr Gly
 1               5

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
ttttggtttg atggaagtaa taaa                                          24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Phe Trp Phe Asp Gly Ser Asn Lys
```

<210> SEQ ID NO 103
<211> LENGTH: 27
<212> TYPE: DNA
<213> ORGANISM: Artificial Sequence
<220> FEATURE:
<223> OTHER INFORMATION: Synthetic

<400> SEQUENCE: 103
gcgagagctt atgatgcttt tgatatc                                        27

<210> SEQ ID NO 104
<211> LENGTH: 9
<212> TYPE: PRT
<213> ORGANISM: Artificial Sequence
<220> FEATURE:
<223> OTHER INFORMATION: Synthetic

<400> SEQUENCE: 104

Ala Arg Ala Tyr Asp Ala Phe Asp Ile
1               5

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccttccacc ctgtctgcat ctgtgggaga cagagtcacc     60
atcacttgcc gggccagtca gagtattagt agctggttgg cctggtatca gcagaaacca    120
gggaaagccc ctaaactcct gatctataag gcgtctagtt tagagagtgg ggtcccatca    180
aggttcagcg gcagtggatc cgggacagaa ttcactctca ccatcagcag cctgcagcct    240
gatgattttg caacttatta ctgccaacag tatagaagtt attctccgac gttcggccaa    300
gggaccaagg tggaaatcaa a                                              321

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Arg Ser Tyr Ser Pro
                85                  90                  95

Thr Phe Gly Gln Gly Thr Lys Val Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagagtatta gtagctgg                                                 18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Ser Ile Ser Ser Trp
 1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 aaggcgtct                                                            9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Lys Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caacagtata gaagttattc tccgacg                                       27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Gln Tyr Arg Ser Tyr Ser Pro Thr
 1               5

<210> SEQ ID NO 113
<211> LENGTH: 348

<212> TYPE: DNA
<213> ORGANISM: Artificial Sequence
<220> FEATURE:
<223> OTHER INFORMATION: Synthetic

<400> SEQUENCE: 113

```
caggtgcagc tggtggagtc tgggggaggc gtggtccagc ctggagggtc cctgagactc      60
tcctgtgaag cgtctggatt caccttcagt tcctatggca tgcactgggt ccgccaggct     120
ccaggcaagg gactggagtg gtggcagtt ttttggtatg atggaagtaa taaatactat     180
gcagactccg tgaagggccg attcaccatc tccagagaca attccaagaa tactctgtat     240
cttcaaatga acagcctgac agccgaggac acggctatat attactgtgc gagagcttat     300
gatgcttttg atatctgggg ccaagggaca atggtcaccg tctcttca                  348
```

<210> SEQ ID NO 114
<211> LENGTH: 116
<212> TYPE: PRT
<213> ORGANISM: Artificial Sequence
<220> FEATURE:
<223> OTHER INFORMATION: Synthetic

<400> SEQUENCE: 114

Gln Val Gln Leu Val Glu Ser Gly Gly Gly Val Val Gln Pro Gly Arg
1               5                   10                  15
Ser Leu Arg Leu Ser Cys Glu Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Phe Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Thr Ala Glu Asp Thr Ala Ile Tyr Tyr Cys
                85                  90                  95
Ala Arg Ala Tyr Asp Ala Phe Asp Ile Trp Gly Gln Gly Thr Met Val
            100                 105                 110
Thr Val Ser Ser
        115

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115

```
ggattcacct tcagttccta tggc                                             24
```

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Ser Ser Tyr Gly
1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
ttttggtatg atggaagtaa taaa                                          24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Phe Trp Tyr Asp Gly Ser Asn Lys
 1               5

<210> SEQ ID NO 119
<211> LENGTH: 27
<212> TYPE: DNA
<213> ORGANISM: Artificial Sequence
<220> FEATURE:
<223> OTHER INFORMATION: Synthetic

<400> SEQUENCE: 119
gcgagagctt atgatgcttt tgatatc                                       27

<210> SEQ ID NO 120
<211> LENGTH: 9
<212> TYPE: PRT
<213> ORGANISM: Artificial Sequence
<220> FEATURE:
<223> OTHER INFORMATION: Synthetic

<400> SEQUENCE: 120

Ala Arg Ala Tyr Asp Ala Phe Asp Ile
 1               5

<210> SEQ ID NO 121
<211> LENGTH: 321
<212> TYPE: DNA
<213> ORGANISM: Artificial Sequence
<220> FEATURE:
<223> OTHER INFORMATION: Synthetic

<400> SEQUENCE: 121
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaaactcct gatctataag gcgtctagtt tagagagtgg ggtcccatca   180
aggttcagcg gcagtggatc tgggacagaa ttcactctca ccatcagcag cctgcagcct   240
gatgattttg caacttatta ctgccaacag tatagaagtt attctccgac gttcggccaa   300
gggaccaagg tggaaatcaa a                                             321

<210> SEQ ID NO 122
<211> LENGTH: 107
<212> TYPE: PRT
<213> ORGANISM: Artificial Sequence
<220> FEATURE:
<223> OTHER INFORMATION: Synthetic

<400> SEQUENCE: 122

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Arg Ser Tyr Ser Pro
                85                  90                  95

Thr Phe Gly Gln Gly Thr Lys Val Glu Ile Lys
            100                 105

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123
cagagtatta gtagctgg                                                 18

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gln Ser Ile Ser Ser Trp
1               5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 aaggcgtct                                                            9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Lys Ala Ser
1

<210> SEQ ID NO 127
<211> LENGTH: 27
<212> TYPE: DNA
<213> ORGANISM: Artificial Sequence
<220> FEATURE:

<223> OTHER INFORMATION: Synthetic

<400> SEQUENCE: 127
caacagtata gaagttattc tccgacg    27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Tyr Arg Ser Tyr Ser Pro Thr
1               5

<210> SEQ ID NO 129
<211> LENGTH: 348
<212> TYPE: DNA
<213> ORGANISM: Artificial Sequence
<220> FEATURE:
<223> OTHER INFORMATION: Synthetic

<400> SEQUENCE: 129
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctggagtg ggtggcagtt ctatggtatg atggaagaaa taaatactat   180
gcagactccg tgaagggccg attcaccatc tccagagaca attccaagaa cacgctgtat   240
ctccaaatga acagcctgag agccgaggac acggctgtgt attactgtgc gagaagctat   300
gatgcttttg atatctgggg ccaagggaca atggtcaccg tctcttca              348

<210> SEQ ID NO 130
<211> LENGTH: 116
<212> TYPE: PRT
<213> ORGANISM: Artificial Sequence
<220> FEATURE:
<223> OTHER INFORMATION: Synthetic

<400> SEQUENCE: 130

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Leu Trp Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Asp Ala Phe Asp Ile Trp Gly Gln Gly Thr Met Val
            100                 105                 110

Thr Val Ser Ser
        115

<210> SEQ ID NO 131
<211> LENGTH: 24
<212> TYPE: DNA

<213> ORGANISM: Artificial Sequence
<220> FEATURE:
<223> OTHER INFORMATION: Synthetic

<400> SEQUENCE: 131
ggattcacct tcagtagcta tggc                                          24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Phe Ser Ser Tyr Gly
 1               5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
ctatggtatg atggaagaaa taaa                                          24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Leu Trp Tyr Asp Gly Arg Asn Lys
 1               5

<210> SEQ ID NO 135
<211> LENGTH: 27
<212> TYPE: DNA
<213> ORGANISM: Artificial Sequence
<220> FEATURE:
<223> OTHER INFORMATION: Synthetic

<400> SEQUENCE: 135
gcgagaagct atgatgcttt tgatatc                                       27

<210> SEQ ID NO 136
<211> LENGTH: 9
<212> TYPE: PRT
<213> ORGANISM: Artificial Sequence
<220> FEATURE:
<223> OTHER INFORMATION: Synthetic

<400> SEQUENCE: 136

Ala Arg Ser Tyr Asp Ala Phe Asp Ile
 1               5

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137
gacatccaga tgacccagtc tccttccacc ctgtctgcat ctgtaggaga cagagtcacc    60
atcacttgcc gggccagtca gagtattagt agctggttgg cctggtttca gcagggacca   120
gggagagccc ctaagctcct gatctataag gcgtctactt tacaaagtgg ggtcccatcg   180
aggttcagcg gcagtggatc tgggacagaa ttcactctca ccatcagcag cctgcagcct   240
gatgattttg caacttatta ctgccaacag tatagaagtt attctccgac gttcggccaa   300
gggaccaagg tggaaatcaa a                                              321

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Phe Gln Gln Gly Pro Gly Arg Ala Pro Lys Leu Leu Ile
         35                  40                  45

Tyr Lys Ala Ser Thr Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Arg Ser Tyr Ser Pro
                 85                  90                  95

Thr Phe Gly Gln Gly Thr Lys Val Glu Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
cagagtatta gtagctgg                                                   18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Ser Ile Ser Ser Trp
 1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 aaggcgtct 9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Lys Ala Ser
 1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caacagtata gaagttattc tccgacg 27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln Gln Tyr Arg Ser Tyr Ser Pro Thr
 1               5

<210> SEQ ID NO 145
<211> LENGTH: 348
<212> TYPE: DNA
<213> ORGANISM: Artificial Sequence
<220> FEATURE:
<223> OTHER INFORMATION: Synthetic

<400> SEQUENCE: 145
cagatcacct tgaaggagtc tggtcctccg ctggtgaaac ccacacagac cctcacgctg    60
acctgcacct tctctgggtt ctcactcaac actaatggaa tgggtgtggg ctggatccgt   120
cagcccccag gaaaggccct ggagtggctt acactcattt attggaatga tgataaacgc   180
tacagcccat ctctgaagac caggctcacc atcaccaagg acacctccaa aaaccaggtg   240
gtccttacaa tgaccaacat ggaccctgtg gacacagcca catattactg tgcacgtttt   300
ggttcgggga cttactgggg ccagggaacc ctggtcactg tctcctca             348

<210> SEQ ID NO 146
<211> LENGTH: 116
<212> TYPE: PRT
<213> ORGANISM: Artificial Sequence
<220> FEATURE:
<223> OTHER INFORMATION: Synthetic

<400> SEQUENCE: 146

Gln Ile Thr Leu Lys Glu Ser Gly Pro Pro Leu Val Lys Pro Thr Gln
 1               5                  10                  15
Thr Leu Thr Leu Thr Cys Thr Phe Ser Gly Phe Ser Leu Asn Thr Asn
                20                  25                  30

```
Gly Met Gly Val Gly Trp Ile Arg Gln Pro Pro Gly Lys Ala Leu Glu
         35                  40                  45

Trp Leu Thr Leu Ile Tyr Trp Asn Asp Asp Lys Arg Tyr Ser Pro Ser
 50                  55                  60

Leu Lys Thr Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Phe Gly Ser Gly Thr Tyr Trp Gly Gln Gly Thr Leu Val
                100                 105                 110

Thr Val Ser Ser
        115

<210> SEQ ID NO 147
<211> LENGTH: 30
<212> TYPE: DNA
<213> ORGANISM: Artificial Sequence
<220> FEATURE:
<223> OTHER INFORMATION: Synthetic

<400> SEQUENCE: 147
gggttctcac tcaacactaa tggaatgggt                                          30

<210> SEQ ID NO 148
<211> LENGTH: 10
<212> TYPE: PRT
<213> ORGANISM: Artificial Sequence
<220> FEATURE:
<223> OTHER INFORMATION: Synthetic

<400> SEQUENCE: 148

Gly Phe Ser Leu Asn Thr Asn Gly Met Gly
 1               5                  10

<210> SEQ ID NO 149
<211> LENGTH: 21
<212> TYPE: DNA
<213> ORGANISM: Artificial Sequence
<220> FEATURE:
<223> OTHER INFORMATION: Synthetic

<400> SEQUENCE: 149
atttattgga atgatgataa a                                                   21

<210> SEQ ID NO 150
<211> LENGTH: 7
<212> TYPE: PRT
<213> ORGANISM: Artificial Sequence
<220> FEATURE:
<223> OTHER INFORMATION: Synthetic

<400> SEQUENCE: 150

Ile Tyr Trp Asn Asp Asp Lys
 1               5

<210> SEQ ID NO 151
<211> LENGTH: 24
<212> TYPE: DNA
<213> ORGANISM: Artificial Sequence
<220> FEATURE:
<223> OTHER INFORMATION: Synthetic

<400> SEQUENCE: 151
gcacgttttg gttcggggac ttac                                                24
```

<210> SEQ ID NO 152
<211> LENGTH: 8
<212> TYPE: PRT
<213> ORGANISM: Artificial Sequence
<220> FEATURE:
<223> OTHER INFORMATION: Synthetic

<400> SEQUENCE: 152

Ala Arg Phe Gly Ser Gly Thr Tyr
 1               5

<210> SEQ ID NO 153
<211> LENGTH: 336
<212> TYPE: DNA
<213> ORGANISM: Artificial Sequence
<220> FEATURE:
<223> OTHER INFORMATION: Synthetic

<400> SEQUENCE: 153
gatattgtga tgactcagtc tccactctcc ctgcccgtca cccctggaga gccggcctcc      60
atctcctgca ggtctagtca gagcctcctg catagttatg gatacaactt tttggattgg     120
ttcctgcaga agccagggca gtctccacaa ctcctgatct atttgggttc tcatcgggcc     180 tccgggtcc ctgacaggtt cagtggcagt ggatcaggca cagattttac actgaaaatc      240
agcagagtgg aggctgagga tgttggggtt tattactgca tgcaagctct acaaactcct     300
ctcactttcg gcggggggac caaggtggag atcaaa                               336

<210> SEQ ID NO 154
<211> LENGTH: 112
<212> TYPE: PRT
<213> ORGANISM: Artificial Sequence
<220> FEATURE:
<223> OTHER INFORMATION: Synthetic

<400> SEQUENCE: 154

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Tyr Gly Tyr Asn Phe Leu Asp Trp Phe Leu Gln Lys Pro Gly Gln Ser
        35                  40                  45

Pro Gln Leu Leu Ile Tyr Leu Gly Ser His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 155
<211> LENGTH: 33
<212> TYPE: DNA
<213> ORGANISM: Artificial Sequence
<220> FEATURE:
<223> OTHER INFORMATION: Synthetic

<400> SEQUENCE: 155
cagagcctcc tgcatagtta tggatacaac ttt                                   33

<210> SEQ ID NO 156
<211> LENGTH: 11
<212> TYPE: PRT
<213> ORGANISM: Artificial Sequence
<220> FEATURE:
<223> OTHER INFORMATION: Synthetic

<400> SEQUENCE: 156

Gln Ser Leu Leu His Ser Tyr Gly Tyr Asn Phe
 1               5                   10

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 ttgggttct                                                                  9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Leu Gly Ser
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
atgcaagctc tacaaactcc tctcact                                             27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Met Gln Ala Leu Gln Thr Pro Leu Thr
 1               5

<210> SEQ ID NO 161
<211> LENGTH: 351
<212> TYPE: DNA
<213> ORGANISM: Artificial Sequence
<220> FEATURE:
<223> OTHER INFORMATION: Synthetic

<400> SEQUENCE: 161
cagctgcagc tgcaggagtc gggcccagga ctggtgaagc cttcggagac cctgtccctc         60
acctgcactg tctctggtgt ctccttcagc agaagtaatt actattgggg ctggagccgc        120
cagcccccag ggaaggggct ggagtggatt gggactatct actatagtgg gaccacctac        180
tataatccgt ccctcgagag tcgagtcatc atatccgcag acacgtccaa taaccagttc    240
tccctgaagg tgaactctgt gaccgccgca gacacggctg tttattattg tgcggtaaca    300
acttacgata tggacgtctg gggccaaggg accacggtca ccgtctcctc a             351

<210> SEQ ID NO 162
<211> LENGTH: 117
<212> TYPE: PRT
<213> ORGANISM: Artificial Sequence
<220> FEATURE:
<223> OTHER INFORMATION: Synthetic

<400> SEQUENCE: 162

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Val Ser Phe Ser Arg Ser
            20                  25                  30

Asn Tyr Tyr Trp Gly Trp Ser Arg Gln Pro Pro Gly Lys Gly Leu Glu
        35                  40                  45

Trp Ile Gly Thr Ile Tyr Tyr Ser Gly Thr Thr Tyr Tyr Asn Pro Ser
    50                  55                  60

Leu Glu Ser Arg Val Ile Ile Ser Ala Asp Thr Ser Asn Asn Gln Phe
65                  70                  75                  80

Ser Leu Lys Val Asn Ser Val Thr Ala Ala Asp Thr Ala Val Tyr Tyr
                85                  90                  95

Cys Ala Val Thr Thr Tyr Asp Met Asp Val Trp Gly Gln Gly Thr Thr
            100                 105                 110

Val Thr Val Ser Ser
        115

<210> SEQ ID NO 163
<211> LENGTH: 30
<212> TYPE: DNA
<213> ORGANISM: Artificial Sequence
<220> FEATURE:
<223> OTHER INFORMATION: Synthetic

<400> SEQUENCE: 163
ggtgtctcct tcagcagaag taattactat                                      30

<210> SEQ ID NO 164
<211> LENGTH: 10
<212> TYPE: PRT
<213> ORGANISM: Artificial Sequence
<220> FEATURE:
<223> OTHER INFORMATION: Synthetic

<400> SEQUENCE: 164

Gly Val Ser Phe Ser Arg Ser Asn Tyr Tyr
 1               5                  10

<210> SEQ ID NO 165
<211> LENGTH: 21
<212> TYPE: DNA
<213> ORGANISM: Artificial Sequence
<220> FEATURE:
<223> OTHER INFORMATION: Synthetic

<400> SEQUENCE: 165
atctactata gtgggaccac c                                               21

<210> SEQ ID NO 166

<210> SEQ ID NO 166
<211> LENGTH: 7
<212> TYPE: PRT
<213> ORGANISM: Artificial Sequence
<220> FEATURE:
<223> OTHER INFORMATION: Synthetic

<400> SEQUENCE: 166

Ile Tyr Tyr Ser Gly Thr Thr
1               5

<210> SEQ ID NO 167
<211> LENGTH: 27
<212> TYPE: DNA
<213> ORGANISM: Artificial Sequence
<220> FEATURE:
<223> OTHER INFORMATION: Synthetic

<400> SEQUENCE: 167
gcggtaacaa cttacgatat ggacgtc                                      27

<210> SEQ ID NO 168
<211> LENGTH: 9
<212> TYPE: PRT
<213> ORGANISM: Artificial Sequence
<220> FEATURE:
<223> OTHER INFORMATION: Synthetic

<400> SEQUENCE: 168

Ala Val Thr Thr Tyr Asp Met Asp Val
1               5

<210> SEQ ID NO 169
<211> LENGTH: 336
<212> TYPE: DNA
<213> ORGANISM: Artificial Sequence
<220> FEATURE:
<223> OTHER INFORMATION: Synthetic

<400> SEQUENCE: 169
gatgttgtga tgactcagtc tccactctcc ctgcccgtca cccttggaca gccggcctcc    60
atctcctgca ggtctagtca agcctcgta tacagtgatg caacaccta cttgaattgg    120
tttcagcaga ggccaggcca atctccaagg cgcctaattt ataaggtttc taaccgggac    180
tctggggtcc cagacagatt cagcggcagt gggtcaggca ctgatttcac actgaaaatc    240
agcagggtgg aggctgagga tgttggggtt tattactgca tgcaaggtac acactggccg    300
tacactttg ccaggggac caagctggag atcaaa                              336

<210> SEQ ID NO 170
<211> LENGTH: 112
<212> TYPE: PRT
<213> ORGANISM: Artificial Sequence
<220> FEATURE:
<223> OTHER INFORMATION: Synthetic

<400> SEQUENCE: 170

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

-continued

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 171
<211> LENGTH: 33
<212> TYPE: DNA
<213> ORGANISM: Artificial Sequence
<220> FEATURE:
<223> OTHER INFORMATION: Synthetic

<400> SEQUENCE: 171
caaagcctcg tatacagtga tggcaacacc tac                                33

<210> SEQ ID NO 172
<211> LENGTH: 11
<212> TYPE: PRT
<213> ORGANISM: Artificial Sequence
<220> FEATURE:
<223> OTHER INFORMATION: Synthetic

<400> SEQUENCE: 172

Gln Ser Leu Val Tyr Ser Asp Gly Asn Thr Tyr
1               5                   10

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 aaggtttct                                                            9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Lys Val Ser
1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
atgcaaggta cacactggcc gtacact                                       27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Met Gln Gly Thr His Trp Pro Tyr Thr
1               5

<210> SEQ ID NO 177
<211> LENGTH: 363
<212> TYPE: DNA
<213> ORGANISM: Artificial Sequence
<220> FEATURE:
<223> OTHER INFORMATION: Synthetic

<400> SEQUENCE: 177

```
caggtgcagc tggtggagtc tgggggaggc gtggtccagc ctggggaggtc cctgagactc     60
tcctgtgcag cgtctggatt caccttcagt agctatggca tgcactgggt ccgccaggct    120
ccaggcaagg ggctggagtg ggtggcagtt atatggtatg atggaagtga taaatactat    180
gcagactccg tgaagggccg attcaccatc tccagagaca attccaagaa cacgctgtat    240
ctgcaaatga acagcctgag agccgaggac acggctgtgt attactgtgc gagagatggg    300
tatggcagca gagggaacta ctttgactac tggggccagg gaaccctggt caccgtctcc    360
tca                                                                  363
```

<210> SEQ ID NO 178
<211> LENGTH: 121
<212> TYPE: PRT
<213> ORGANISM: Artificial Sequence
<220> FEATURE:
<223> OTHER INFORMATION: Synthetic

<400> SEQUENCE: 178

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Gly Ser Arg Gly Asn Tyr Phe Asp Tyr Trp Gly
            100                 105                 110

Gln Gly Thr Leu Val Thr Val Ser Ser
        115                 120

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179

```
ggattcacct tcagtagcta tggc                                            24
```

<210> SEQ ID NO 180
<211> LENGTH: 8

```
<212> TYPE: PRT
<213> ORGANISM: Artificial Sequence
<220> FEATURE:
<223> OTHER INFORMATION: Synthetic

<400> SEQUENCE: 180

Gly Phe Thr Phe Ser Ser Tyr Gly
 1               5

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
atatggtatg atggaagtga taaa                                          24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Trp Tyr Asp Gly Ser Asp Lys
 1               5

<210> SEQ ID NO 183
<211> LENGTH: 42
<212> TYPE: DNA
<213> ORGANISM: Artificial Sequence
<220> FEATURE:
<223> OTHER INFORMATION: Synthetic

<400> SEQUENCE: 183
gcgagagatg ggtatggcag cagagggaac tactttgact ac                      42

<210> SEQ ID NO 184
<211> LENGTH: 14
<212> TYPE: PRT
<213> ORGANISM: Artificial Sequence
<220> FEATURE:
<223> OTHER INFORMATION: Synthetic

<400> SEQUENCE: 184

Ala Arg Asp Gly Tyr Gly Ser Arg Gly Asn Tyr Phe Asp Tyr
 1               5                  10

<210> SEQ ID NO 185
<211> LENGTH: 336
<212> TYPE: DNA
<213> ORGANISM: Artificial Sequence
<220> FEATURE:
<223> OTHER INFORMATION: Synthetic

<400> SEQUENCE: 185
gatgttgtga tgacccagtc tccactctcc ctgcccgtca cccttggaca gccggcctcc   60
atctcctgca ggtctagtca aagcctcgta tacagtgatg aaacaccta cttgaattgg   120 tttcagcaga ggccaggcca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggcct   300
```

-continued

```
cccactttcg gcggagggac caaggtggag atcaaa                                    336
```

<210> SEQ ID NO 186
<211> LENGTH: 112
<212> TYPE: PRT
<213> ORGANISM: Artificial Sequence
<220> FEATURE:
<223> OTHER INFORMATION: Synthetic

<400> SEQUENCE: 186

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Pro Thr Phe Gly Gly Gly Thr Lys Val Glu Ile Lys
             100                 105                 110
```

<210> SEQ ID NO 187
<211> LENGTH: 33
<212> TYPE: DNA
<213> ORGANISM: Artificial Sequence
<220> FEATURE:
<223> OTHER INFORMATION: Synthetic

<400> SEQUENCE: 187

```
caaagcctcg tatacagtga tggaaacacc tac                                       33
```

<210> SEQ ID NO 188
<211> LENGTH: 11
<212> TYPE: PRT
<213> ORGANISM: Artificial Sequence
<220> FEATURE:
<223> OTHER INFORMATION: Synthetic

<400> SEQUENCE: 188

```
Gln Ser Leu Val Tyr Ser Asp Gly Asn Thr Tyr
 1               5                  10
```

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189

```
aaggtttct                                                                   9
```

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Lys Val Ser
 1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
atgcaaggta cacactggcc tcccact                                           27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Met Gln Gly Thr His Trp Pro Pro Thr
 1               5

<210> SEQ ID NO 193
<211> LENGTH: 363
<212> TYPE: DNA
<213> ORGANISM: Artificial Sequence
<220> FEATURE:
<223> OTHER INFORMATION: Synthetic

<400> SEQUENCE: 193
caggtgcagc tggtggagtc tgggggaggc gtggtccagc ctgggaggtc cctgagactc        60
tcctgtgcag cgtctggatt caccttcggt agctatggca tgcactgggt ccgccaggct       120
ccaggcaagg ggctggagtg ggtggcagtt atatggtatg atggaagtga tgaatattat       180
acagactccg tgaagggccg attcaccgtc tccagagaca attccaagta cacactgtat       240
ctgcaaatga acagcctgag agccgacgac acggctgtgt attattgtgc gagagatggg       300
tatagaacca gagggaacta ctttgactac tggggccagg gaaccctggt caccgtctcc       360
tca                                                                    363

<210> SEQ ID NO 194
<211> LENGTH: 121
<212> TYPE: PRT
<213> ORGANISM: Artificial Sequence
<220> FEATURE:
<223> OTHER INFORMATION: Synthetic

<400> SEQUENCE: 194

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Gly Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asp Glu Tyr Tyr Thr Asp Ser Val
     50                  55                  60

Lys Gly Arg Phe Thr Val Ser Arg Asp Asn Ser Lys Tyr Thr Leu Tyr
 65                  70                  75                  80

```
Leu Gln Met Asn Ser Leu Arg Ala Asp Asp Thr Ala Val Tyr Tyr Cys
                 85                  90                  95

Ala Arg Asp Gly Tyr Arg Thr Arg Gly Asn Tyr Phe Asp Tyr Trp Gly
            100                 105                 110

Gln Gly Thr Leu Val Thr Val Ser Ser
        115                 120

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
ggattcacct tcggtagcta tggc                                          24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Phe Thr Phe Gly Ser Tyr Gly
  1               5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
atatggtatg atggaagtga tgaa                                          24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Trp Tyr Asp Gly Ser Asp Glu
  1               5

<210> SEQ ID NO 199
<211> LENGTH: 42
<212> TYPE: DNA
<213> ORGANISM: Artificial Sequence
<220> FEATURE:
<223> OTHER INFORMATION: Synthetic

<400> SEQUENCE: 199
gcgagagatg ggtatagaac cagagggaac tactttgact ac                      42

<210> SEQ ID NO 200
<211> LENGTH: 14
<212> TYPE: PRT
<213> ORGANISM: Artificial Sequence
<220> FEATURE:
<223> OTHER INFORMATION: Synthetic
```

<400> SEQUENCE: 200

Ala Arg Asp Gly Tyr Arg Thr Arg Gly Asn Tyr Phe Asp Tyr
1               5                   10

<210> SEQ ID NO 201
<211> LENGTH: 336
<212> TYPE: DNA
<213> ORGANISM: Artificial Sequence
<220> FEATURE:
<223> OTHER INFORMATION: Synthetic

<400> SEQUENCE: 201
gatgttgtga tgactcagtc tccactctcc ctgcccgtcg cccttggaca gccggcctcc    60
atctcctgca ggtctagtca aagcctcgta tacagtgatg aaacaccta cttgaattgg   120 tttcagcaga ggccaggcca atctccaagg cgcctaattt ataaggtttc taaccgggac   180
tctggggtcc cagacagatt cggcggcagt gggtcaggca ctgatttcac actgaaaatc   240
agcagggtgg aggctgagga tgttggcctt tattactgca tgcaaggtac acactggcct   300
cccactttcg gcggagggac caaggtggag atcaaa                              336

<210> SEQ ID NO 202
<211> LENGTH: 112
<212> TYPE: PRT
<213> ORGANISM: Artificial Sequence
<220> FEATURE:
<223> OTHER INFORMATION: Synthetic

<400> SEQUENCE: 202

Asp Val Val Met Thr Gln Ser Pro Leu Ser Leu Pro Val Ala Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Gly Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Gly
                85                  90                  95

Thr His Trp Pro Pro Thr Phe Gly Gly Gly Thr Lys Val Glu Ile Lys
            100                 105                 110

<210> SEQ ID NO 203
<211> LENGTH: 33
<212> TYPE: DNA
<213> ORGANISM: Artificial Sequence
<220> FEATURE:
<223> OTHER INFORMATION: Synthetic

<400> SEQUENCE: 203
caaagcctcg tatacagtga tggaaacacc tac                                 33

<210> SEQ ID NO 204
<211> LENGTH: 11
<212> TYPE: PRT
<213> ORGANISM: Artificial Sequence
<220> FEATURE:
<223> OTHER INFORMATION: Synthetic

<400> SEQUENCE: 204

Gln Ser Leu Val Tyr Ser Asp Gly Asn Thr Tyr
 1               5                   10

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 aaggtttct                                                                    9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Lys Val Ser
 1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
atgcaaggta cacactggcc tcccact                                               27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Met Gln Gly Thr His Trp Pro Pro Thr
 1               5

<210> SEQ ID NO 209
<211> LENGTH: 357
<212> TYPE: DNA
<213> ORGANISM: Artificial Sequence
<220> FEATURE:
<223> OTHER INFORMATION: Synthetic

<400> SEQUENCE: 209
gaggtgcagc tggtggagtc tgggggaggc ttggtacagc cggggggtc cctgagactc         60 tcctgtgcag cctctggatt cactttagc aactatgcca tgagttgggt ccgccaggct        120
cccgggaagg gctggagtg gtctcagcg gtcagtggta gtggtgttgg cacatactac         180
gcagactccg tgaagggccg gttcaccatc tccagagaca attccaagaa cacgctgtat        240
ctgcaaatga agagcctgag cgccgaggac acggccttat attactgtac gaaaaccta         300 ggtggaaccc acgctttga tatctggggc caagggacaa tggtcaccgt ctcttca           357

<210> SEQ ID NO 210
<211> LENGTH: 119

<212> TYPE: PRT
<213> ORGANISM: Artificial Sequence
<220> FEATURE:
<223> OTHER INFORMATION: Synthetic

<400> SEQUENCE: 210

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Val Ser Gly Ser Gly Val Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Ser Ala Glu Asp Thr Ala Leu Tyr Tyr Cys
                85                  90                  95

Thr Lys Thr Leu Gly Gly Thr His Ala Phe Asp Ile Trp Gly Gln Gly
            100                 105                 110

Thr Met Val Thr Val Ser Ser
        115

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcactt ttagcaacta tgcc                                      24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Asn Tyr Ala
 1               5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
gtcagtggta gtggtgttgg caca                                      24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Val Ser Gly Ser Gly Val Gly Thr

<210> SEQ ID NO 215
<211> LENGTH: 36
<212> TYPE: DNA
<213> ORGANISM: Artificial Sequence
<220> FEATURE:
<223> OTHER INFORMATION: Synthetic

<400> SEQUENCE: 215
acgaaaaccc taggtggaac ccacgctttt gatatc        36

<210> SEQ ID NO 216
<211> LENGTH: 12
<212> TYPE: PRT
<213> ORGANISM: Artificial Sequence
<220> FEATURE:
<223> OTHER INFORMATION: Synthetic

<400> SEQUENCE: 216

Thr Lys Thr Leu Gly Gly Thr His Ala Phe Asp Ile
 1               5                  10

<210> SEQ ID NO 217
<211> LENGTH: 318
<212> TYPE: DNA
<213> ORGANISM: Artificial Sequence
<220> FEATURE:
<223> OTHER INFORMATION: Synthetic

<400> SEQUENCE: 217
gacatccaga tgacccagtc tccttccacc ctgtctgcat ctgtaggaga cagagtcacc        60
atcacttgcc gggccagtca gagtattagt aggtggttgg cctggtatca gcagaaacca       120
gggaaagccc ctaagctcct gatctataag gcgtctagtt tagaaagtgg ggtcccatca       180
aggttcagcg gcagtggatc tgggacagaa ttcactgtca ccatcaacag cctgcagcct       240
gatgattttg caacttatta ctgccaacag tataacagtt attccagttt tggccagggg       300
accaagctgg agatcaaa                                                     318

<210> SEQ ID NO 218
<211> LENGTH: 106
<212> TYPE: PRT
<213> ORGANISM: Artificial Sequence
<220> FEATURE:
<223> OTHER INFORMATION: Synthetic

<400> SEQUENCE: 218

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Arg Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Val Thr Ile Asn Ser Leu Gln Pro
 65                  70                  75                  80

Asp Asp Phe Ala Thr Tyr Tyr Cys Gln Gln Tyr Asn Ser Tyr Ser Ser
                 85                  90                  95

Phe Gly Gln Gly Thr Lys Leu Glu Ile Lys
            100                 105

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219
cagagtatta gtaggtgg                                                 18

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

Gln Ser Ile Ser Arg Trp
 1               5

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 aaggcgtct                                                            9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

Lys Ala Ser
 1

<210> SEQ ID NO 223
<211> LENGTH: 24
<212> TYPE: DNA
<213> ORGANISM: Artificial Sequence
<220> FEATURE:
<223> OTHER INFORMATION: Synthetic

<400> SEQUENCE: 223
caacagtata acagttattc cagt                                          24

<210> SEQ ID NO 224
<211> LENGTH: 8
<212> TYPE: PRT
<213> ORGANISM: Artificial Sequence
<220> FEATURE:
<223> OTHER INFORMATION: Synthetic

<400> SEQUENCE: 224

Gln Gln Tyr Asn Ser Tyr Ser Ser
 1               5

<210> SEQ ID NO 225
<211> LENGTH: 357

<212> TYPE: DNA
<213> ORGANISM: Artificial Sequence
<220> FEATURE:
<223> OTHER INFORMATION: Synthetic

<400> SEQUENCE: 225

```
gaggtgcagc tggtggagtc tggggaaggc ttggtccagc ctgggggtc cctgagactc    60
tcctgtgcag cctctggatt catctttagc agctatgcca tgagctgggt ccgccaggct   120
ccagggaagg ggctggagtg gtctcagct attagtggta gtggtgttgg cacatactac   180
gcagactccg tgaagggccg tttcaccatc tccagagaca attccaagaa cacgctgtat   240
ctgcaaatga acagcctgag agccgaggac acggccgtat attctgtgc gaaaacccta   300
tctggaaccc atgcttttga tatctggggc caagggacaa tggtcaccgt ctcttca      357
```

<210> SEQ ID NO 226
<211> LENGTH: 119
<212> TYPE: PRT
<213> ORGANISM: Artificial Sequence
<220> FEATURE:
<223> OTHER INFORMATION: Synthetic

<400> SEQUENCE: 226

```
Glu Val Gln Leu Val Glu Ser Gly Glu Gly Leu Val Gln Pro Gly Gly
 1               5                  10                  15
Ser Leu Arg Leu Ser Cys Ala Ala Ser Gly Phe Ile Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Val Gly Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Phe Cys
                85                  90                  95
Ala Lys Thr Leu Ser Gly Thr His Ala Phe Asp Ile Trp Gly Gln Gly
            100                 105                 110
Thr Met Val Thr Val Ser Ser
        115
```

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227

```
ggattcatct ttagcagcta tgcc                                            24
```

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

```
Gly Phe Ile Phe Ser Ser Tyr Ala
 1               5
```

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
attagtggta gtggtgttgg caca                                              24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Gly Ser Gly Val Gly Thr
1               5

<210> SEQ ID NO 231
<211> LENGTH: 36
<212> TYPE: DNA
<213> ORGANISM: Artificial Sequence
<220> FEATURE:
<223> OTHER INFORMATION: Synthetic

<400> SEQUENCE: 231
gcgaaaaccc tatctggaac ccatgctttt gatatc                                 36

<210> SEQ ID NO 232
<211> LENGTH: 12
<212> TYPE: PRT
<213> ORGANISM: Artificial Sequence
<220> FEATURE:
<223> OTHER INFORMATION: Synthetic

<400> SEQUENCE: 232

Ala Lys Thr Leu Ser Gly Thr His Ala Phe Asp Ile
1               5                   10

<210> SEQ ID NO 233
<211> LENGTH: 318
<212> TYPE: DNA
<213> ORGANISM: Artificial Sequence
<220> FEATURE:
<223> OTHER INFORMATION: Synthetic

<400> SEQUENCE: 233
gacatccaga tgacccagtc tccttccacc ctgtctgcat ctgtaggaga cagagtcacc       60
atcacttgcc gggccagtca gagtattagt agctggttgg cctggtatca gcagaaacca      120
gggaaagccc ctaagctcct gatctataag gcgtctagtt tacaaagtgg ggtcccatca      180
aggttcagcg gcagtggatc tgggacagag ttcactctca ccatcagcag cctgcagtct      240
gatgattttg caacttatta ctgccaacag tataatagtt attccacttt tggccagggg      300
accaagctgg agatcaaa                                                    318

<210> SEQ ID NO 234
<211> LENGTH: 106
<212> TYPE: PRT
<213> ORGANISM: Artificial Sequence
<220> FEATURE:
<223> OTHER INFORMATION: Synthetic

<400> SEQUENCE: 234

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Ser
65                  70                  75                  80

Asp Asp Phe Ala Thr Tyr Tyr Cys Gln Gln Tyr Asn Ser Tyr Ser Thr
                85                  90                  95

Phe Gly Gln Gly Thr Lys Leu Glu Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235
cagagtatta gtagctgg                                                        18

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Ser Ile Ser Ser Trp
1               5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 aaggcgtct                                                                   9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Lys Ala Ser
1

<210> SEQ ID NO 239
<211> LENGTH: 24
<212> TYPE: DNA
<213> ORGANISM: Artificial Sequence
<220> FEATURE:

<223> OTHER INFORMATION: Synthetic

<400> SEQUENCE: 239
caacagtata atagttattc cact                                                24

<210> SEQ ID NO 240
<211> LENGTH: 8
<212> TYPE: PRT
<213> ORGANISM: Artificial Sequence
<220> FEATURE:
<223> OTHER INFORMATION: Synthetic

<400> SEQUENCE: 240

Gln Gln Tyr Asn Ser Tyr Ser Thr
1               5

<210> SEQ ID NO 241
<211> LENGTH: 348
<212> TYPE: DNA
<213> ORGANISM: Artificial Sequence
<220> FEATURE:
<223> OTHER INFORMATION: Synthetic

<400> SEQUENCE: 241
gaggtgcagc tggtggagtc tgggggaggc ttggtaaagc ctgggggggtc cctaagactc          60 tcctgtgcag tctctggatt cactttcagt atcgactgga tgatctgggt ccgccaggct         120
ccagggacgg ggctggaatg ggttggccgt attaaaagaa aaactgatgg tgggacaaca         180
gactacgcag cacccgtaaa aggcagattc accatctcaa gagatgattc aaaaaacacg         240
ctttacctac aaatgaatag cctgaaaacc gaggacacag ccatatatta ctgtgccaca         300
ggaggcttcg agagggtggg ccagggaacc ctggtcaccg tctcctca                      348

<210> SEQ ID NO 242
<211> LENGTH: 116
<212> TYPE: PRT
<213> ORGANISM: Artificial Sequence
<220> FEATURE:
<223> OTHER INFORMATION: Synthetic

<400> SEQUENCE: 242

Glu Val Gln Leu Val Glu Ser Gly Gly Gly Leu Val Lys Pro Gly Gly
1               5                   10                  15

Ser Leu Arg Leu Ser Cys Ala Val Ser Gly Phe Thr Phe Ser Ile Asp
            20                  25                  30

Trp Met Ile Trp Val Arg Gln Ala Pro Gly Thr Gly Leu Glu Trp Val
        35                  40                  45

Gly Arg Ile Lys Arg Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Ile Tyr
                85                  90                  95

Tyr Cys Ala Thr Gly Gly Phe Glu Arg Val Gly Gln Gly Thr Leu Val
            100                 105                 110

Thr Val Ser Ser
        115

<210> SEQ ID NO 243
<211> LENGTH: 24
<212> TYPE: DNA

```
<213> ORGANISM: Artificial Sequence
<220> FEATURE:
<223> OTHER INFORMATION: Synthetic

<400> SEQUENCE: 243
ggattcactt tcagtatcga ctgg                                              24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Ser Ile Asp Trp
 1               5

<210> SEQ ID NO 245
<211> LENGTH: 30
<212> TYPE: DNA
<213> ORGANISM: Artificial Sequence
<220> FEATURE:
<223> OTHER INFORMATION: Synthetic

<400> SEQUENCE: 245
attaaaagaa aaactgatgg tgggacaaca                                        30

<210> SEQ ID NO 246
<211> LENGTH: 10
<212> TYPE: PRT
<213> ORGANISM: Artificial Sequence
<220> FEATURE:
<223> OTHER INFORMATION: Synthetic

<400> SEQUENCE: 246

Ile Lys Arg Lys Thr Asp Gly Gly Thr Thr
 1               5                  10

<210> SEQ ID NO 247
<211> LENGTH: 21
<212> TYPE: DNA
<213> ORGANISM: Artificial Sequence
<220> FEATURE:
<223> OTHER INFORMATION: Synthetic

<400> SEQUENCE: 247
gccacaggag gcttcgagag g                                                 21

<210> SEQ ID NO 248
<211> LENGTH: 7
<212> TYPE: PRT
<213> ORGANISM: Artificial Sequence
<220> FEATURE:
<223> OTHER INFORMATION: Synthetic

<400> SEQUENCE: 248

Ala Thr Gly Gly Phe Glu Arg
 1               5

<210> SEQ ID NO 249
<211> LENGTH: 336
<212> TYPE: DNA
<213> ORGANISM: Artificial Sequence
<220> FEATURE:
<223> OTHER INFORMATION: Synthetic
```

<400> SEQUENCE: 249

```
gatgttgtga tgactcagtc tccactctcc ctgcccgtca cccttggaca gccggcctcc    60
atctcctgca ggtctagtca aagcctcgtt tacagtgatg gaaacaccta cttgaattgg   120
tttcagcaga ggccaggcca atctccaagg cgcctaattt ataagatttc taaccgggac   180
tctggggtcc cagacagatt cagcggcagt gggtcaggca ctgatttcac actgaaaatc   240
agcagggtgg aggctgagga tgttggggttt tattactgca tgcagggtac acactggccg   300
ctcactttcg gcggagggac caaggtggag atcaaa                              336
```

<210> SEQ ID NO 250
<211> LENGTH: 112
<212> TYPE: PRT
<213> ORGANISM: Artificial Sequence
<220> FEATURE:
<223> OTHER INFORMATION: Synthetic

<400> SEQUENCE: 250

```
Asp Val Val Met Thr Gln Ser Pro Leu Ser Leu Pro Val Thr Leu Gly
  1               5                  10                  15
Gln Pro Ala Ser Ile Ser Cys Arg Ser Ser Gln Ser Leu Val Tyr Ser
             20                  25                  30
Asp Gly Asn Thr Tyr Leu Asn Trp Phe Gln Gln Arg Pro Gly Gln Ser
         35                  40                  45
Pro Arg Arg Leu Ile Tyr Lys Ile Ser Asn Arg Asp Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Phe Tyr Tyr Cys Met Gln Gly
                 85                  90                  95
Thr His Trp Pro Leu Thr Phe Gly Gly Gly Thr Lys Val Glu Ile Lys
            100                 105                 110
```

<210> SEQ ID NO 251
<211> LENGTH: 33
<212> TYPE: DNA
<213> ORGANISM: Artificial Sequence
<220> FEATURE:
<223> OTHER INFORMATION: Synthetic

<400> SEQUENCE: 251

```
caaagcctcg tttacagtga tggaaacacc tac                                  33
```

<210> SEQ ID NO 252
<211> LENGTH: 11
<212> TYPE: PRT
<213> ORGANISM: Artificial Sequence
<220> FEATURE:
<223> OTHER INFORMATION: Synthetic

<400> SEQUENCE: 252

```
Gln Ser Leu Val Tyr Ser Asp Gly Asn Thr Tyr
  1               5                  10
```

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253

```
aagatttct                                                                    9
```

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Lys Ile Ser
 1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255

```
atgcagggta cacactggcc gctcact                                               27
```

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Met Gln Gly Thr His Trp Pro Leu Thr
 1               5

<210> SEQ ID NO 257
<211> LENGTH: 348
<212> TYPE: DNA
<213> ORGANISM: Artificial Sequence
<220> FEATURE:
<223> OTHER INFORMATION: Synthetic

<400> SEQUENCE: 257

```
gaggtgcagc tggtggagtc tgggggaggc ttggtaaagc ctgggggtc cctaagactc         60 tcctgtgcag tctctggatt cactttcagt atcgactgga tgatctgggt ccgccaggct        120
ccagggacgg ggctggaatg ggttggccgt attaaaagaa aaactgatgg tgggacaaca        180
gactacgcag cacccgtaaa aggcagattc accatctcaa gagatgattc aaaaaacacg        240
ctttacctac aaatgaatag cctgaaaacc gaggacacag ccatatatta ctgtgccaca        300
ggaggcttcg agaggtgggg ccagggaacc ctggtcaccg tctcctca                     348
```

<210> SEQ ID NO 258
<211> LENGTH: 116
<212> TYPE: PRT
<213> ORGANISM: Artificial Sequence
<220> FEATURE:
<223> OTHER INFORMATION: Synthetic

<400> SEQUENCE: 258

Glu Val Gln Leu Val Glu Ser Gly Gly Gly Leu Val Lys Pro Gly Gly
 1               5                   10                  15

Ser Leu Arg Leu Ser Cys Ala Val Ser Gly Phe Thr Phe Ser Ile Asp
            20                  25                  30

-continued

```
Trp Met Ile Trp Val Arg Gln Ala Pro Gly Thr Gly Leu Glu Trp Val
         35                  40                  45
Gly Arg Ile Lys Arg Lys Thr Asp Gly Gly Thr Thr Asp Tyr Ala Ala
 50                  55                  60
Pro Val Lys Gly Arg Phe Thr Ile Ser Arg Asp Asp Ser Lys Asn Thr
 65                  70                  75                  80
Leu Tyr Leu Gln Met Asn Ser Leu Lys Thr Glu Asp Thr Ala Ile Tyr
                 85                  90                  95
Tyr Cys Ala Thr Gly Gly Phe Glu Arg Trp Gly Gln Gly Thr Leu Val
            100                 105                 110
Thr Val Ser Ser
        115

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259
ggattcactt tcagtatcga ctgg                                      24

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Gly Phe Thr Phe Ser Ile Asp Trp
 1               5

<210> SEQ ID NO 261
<211> LENGTH: 30
<212> TYPE: DNA
<213> ORGANISM: Artificial Sequence
<220> FEATURE:
<223> OTHER INFORMATION: Synthetic

<400> SEQUENCE: 261
attaaaagaa aaactgatgg tgggacaaca                                30

<210> SEQ ID NO 262
<211> LENGTH: 10
<212> TYPE: PRT
<213> ORGANISM: Artificial Sequence
<220> FEATURE:
<223> OTHER INFORMATION: Synthetic

<400> SEQUENCE: 262

Ile Lys Arg Lys Thr Asp Gly Gly Thr Thr
 1               5                  10

<210> SEQ ID NO 263
<211> LENGTH: 21
<212> TYPE: DNA
<213> ORGANISM: Artificial Sequence
<220> FEATURE:
<223> OTHER INFORMATION: Synthetic

<400> SEQUENCE: 263
gccacaggag gcttcgagag g                                         21
```

<210> SEQ ID NO 264
<211> LENGTH: 7
<212> TYPE: PRT
<213> ORGANISM: Artificial Sequence
<220> FEATURE:
<223> OTHER INFORMATION: Synthetic

<400> SEQUENCE: 264

Ala Thr Gly Gly Phe Glu Arg
 1               5

<210> SEQ ID NO 265
<211> LENGTH: 336
<212> TYPE: DNA
<213> ORGANISM: Artificial Sequence
<220> FEATURE:
<223> OTHER INFORMATION: Synthetic

<400> SEQUENCE: 265
gatgttgtga tgactcagtc tccactctcc ctgcccgtca cccttggaca gccggcctcc     60
atctcctgca ggtctagtca aagcctcgtt tacagtgatg gaaacaccta cttgaattgg    120
tttcagcaga ggccaggcca atctccaagg cgcctaattt ataagatttc taaccgggac    180
tctggggtcc cagacagatt cagcggcagt gggtcaggca ctgatttcac actgaaaatc    240
agcagggtgg aggctgagga tgttgggttt tattactgca tgcagggtac acactggccg    300
ctcactttcg gcggagggac caaggtggag atcaaa                             336

<210> SEQ ID NO 266
<211> LENGTH: 112
<212> TYPE: PRT
<213> ORGANISM: Artificial Sequence
<220> FEATURE:
<223> OTHER INFORMATION: Synthetic

<400> SEQUENCE: 266

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Ile Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Phe Tyr Tyr Cys Met Gln Gly
                 85                  90                  95

Thr His Trp Pro Leu Thr Phe Gly Gly Gly Thr Lys Val Glu Ile Lys
            100                 105                 110

<210> SEQ ID NO 267
<211> LENGTH: 33
<212> TYPE: DNA
<213> ORGANISM: Artificial Sequence
<220> FEATURE:
<223> OTHER INFORMATION: Synthetic

<400> SEQUENCE: 267
caaagcctcg tttacagtga tggaaacacc tac                                 33

<210> SEQ ID NO 268
<211> LENGTH: 11
<212> TYPE: PRT
<213> ORGANISM: Artificial Sequence
<220> FEATURE:
<223> OTHER INFORMATION: Synthetic

<400> SEQUENCE: 268

Gln Ser Leu Val Tyr Ser Asp Gly Asn Thr Tyr
 1               5                  10

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 aagatttct                                                                  9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Lys Ile Ser
 1

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
atgcagggta cacactggcc gctcact                                             27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Met Gln Gly Thr His Trp Pro Leu Thr
 1               5

<210> SEQ ID NO 273
<211> LENGTH: 348
<212> TYPE: DNA
<213> ORGANISM: Artificial Sequence
<220> FEATURE:
<223> OTHER INFORMATION: Synthetic

<400> SEQUENCE: 273
gaggtgcagc tggtggagtc tgggggaggc ttggtaaagc ctggggggtc ccttagactc          60
tcctgtgcag cctctggatt cactttcagt aacgactgga tgagctgggt ccgccaggct         120
ccagggaagg ggctggaatg ggttggccgt attaaaagga aaactgatgg tgggacaaca         180

```
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
ggaggctacg agagggggg ccagggaacc ctggtcaccg tctcctca                  348
```

<210> SEQ ID NO 274
<211> LENGTH: 116
<212> TYPE: PRT
<213> ORGANISM: Artificial Sequence
<220> FEATURE:
<223> OTHER INFORMATION: Synthetic

<400> SEQUENCE: 274

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Asp
            20                  25                  30

Trp Met Ser Trp Val Arg Gln Ala Pro Gly Lys Gly Leu Glu Trp Val
        35                  40                  45

Gly Arg Ile Lys Arg Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Gly Tyr Glu Arg Gly Gly Gln Gly Thr Leu Val
            100                 105                 110

Thr Val Ser Ser
        115
```

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275

```
ggattcactt tcagtaacga ctgg                                           24
```

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

```
Gly Phe Thr Phe Ser Asn Asp Trp
 1               5
```

<210> SEQ ID NO 277
<211> LENGTH: 30
<212> TYPE: DNA
<213> ORGANISM: Artificial Sequence
<220> FEATURE:
<223> OTHER INFORMATION: Synthetic

<400> SEQUENCE: 277

```
attaaaagga aaactgatgg tgggacaaca                                     30
```

<210> SEQ ID NO 278

<211> LENGTH: 10
<212> TYPE: PRT
<213> ORGANISM: Artificial Sequence
<220> FEATURE:
<223> OTHER INFORMATION: Synthetic

<400> SEQUENCE: 278

Ile Lys Arg Lys Thr Asp Gly Gly Thr Thr
1               5                   10

<210> SEQ ID NO 279
<211> LENGTH: 21
<212> TYPE: DNA
<213> ORGANISM: Artificial Sequence
<220> FEATURE:
<223> OTHER INFORMATION: Synthetic

<400> SEQUENCE: 279
accacaggag gctacgagag g                                         21

<210> SEQ ID NO 280
<211> LENGTH: 7
<212> TYPE: PRT
<213> ORGANISM: Artificial Sequence
<220> FEATURE:
<223> OTHER INFORMATION: Synthetic

<400> SEQUENCE: 280

Thr Thr Gly Gly Tyr Glu Arg
1               5

<210> SEQ ID NO 281
<211> LENGTH: 336
<212> TYPE: DNA
<213> ORGANISM: Artificial Sequence
<220> FEATURE:
<223> OTHER INFORMATION: Synthetic

<400> SEQUENCE: 281
gatgttgtga tgactcagtc tccactctcc ctgcccgtca cccttggaca gccggcctcc    60
atctcctgca ggtctagtca aagcctcgta tacagtgatg aaacacccta cttgaattgg   120
tttcagcaga ggccaggcca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcagggtac acactggccg   300
ctcactttcg gcggagggac caaggtggag atcaaa                             336

<210> SEQ ID NO 282
<211> LENGTH: 112
<212> TYPE: PRT
<213> ORGANISM: Artificial Sequence
<220> FEATURE:
<223> OTHER INFORMATION: Synthetic

<400> SEQUENCE: 282

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Lys Val Glu Ile Lys
            100                 105                 110
```

<210> SEQ ID NO 283
<211> LENGTH: 33
<212> TYPE: DNA
<213> ORGANISM: Artificial Sequence
<220> FEATURE:
<223> OTHER INFORMATION: Synthetic

<400> SEQUENCE: 283
caaagcctcg tatacagtga tggaaacacc tac                                   33

<210> SEQ ID NO 284
<211> LENGTH: 11
<212> TYPE: PRT
<213> ORGANISM: Artificial Sequence
<220> FEATURE:
<223> OTHER INFORMATION: Synthetic

<400> SEQUENCE: 284

```
Gln Ser Leu Val Tyr Ser Asp Gly Asn Thr Tyr
 1               5                  10
```

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 aaggtttct                                                              9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

```
Lys Val Ser
 1
```

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
atgcagggta cacactggcc gctcact                                          27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Met Gln Gly Thr His Trp Pro Leu Thr
 1               5

<210> SEQ ID NO 289
<211> LENGTH: 357
<212> TYPE: DNA
<213> ORGANISM: Artificial Sequence
<220> FEATURE:
<223> OTHER INFORMATION: Synthetic

<400> SEQUENCE: 289

```
gaggtgcagc tggtggagtc tgggggaggc ttggtacagc ctgggggtc cctgagactc     60
tcctgtgcag cctctggatt cacctttagc agctatgcca tgagctgggt ccgccaggct    120
ccagggaagg ggctggagtg ggtctcagct attagtggta gtggtgttag cacatactac    180
gcagactccg tgaagggccg gttcaccatc tccagagaca attccaagaa cacgctgtat    240
ctgcaaatga acagcctgag agccgaggac acggccgtat attactgtcc gaaagctcga    300
actggaaccc atgcttttga tatctggggc caagggacaa tggtcaccgt ctcttca       357
```

<210> SEQ ID NO 290
<211> LENGTH: 119
<212> TYPE: PRT
<213> ORGANISM: Artificial Sequence
<220> FEATURE:
<223> OTHER INFORMATION: Synthetic

<400> SEQUENCE: 290

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Val Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Pro Lys Ala Arg Thr Gly Thr His Ala Phe Asp Ile Trp Gly Gln Gly
            100                 105                 110

Thr Met Val Thr Val Ser Ser
        115

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291

```
ggattcacct ttagcagcta tgcc                                            24
```

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Thr Phe Ser Ser Tyr Ala
1               5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
attagtggta gtggtgttag caca                                              24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Ser Gly Ser Gly Val Ser Thr
1               5

<210> SEQ ID NO 295
<211> LENGTH: 36
<212> TYPE: DNA
<213> ORGANISM: Artificial Sequence
<220> FEATURE:
<223> OTHER INFORMATION: Synthetic

<400> SEQUENCE: 295
ccgaaagctc gaactggaac ccatgctttt gatatc                                 36

<210> SEQ ID NO 296
<211> LENGTH: 12
<212> TYPE: PRT
<213> ORGANISM: Artificial Sequence
<220> FEATURE:
<223> OTHER INFORMATION: Synthetic

<400> SEQUENCE: 296

Pro Lys Ala Arg Thr Gly Thr His Ala Phe Asp Ile
1               5                   10

<210> SEQ ID NO 297
<211> LENGTH: 318
<212> TYPE: DNA
<213> ORGANISM: Artificial Sequence
<220> FEATURE:
<223> OTHER INFORMATION: Synthetic

<400> SEQUENCE: 297
gacatccaga tgacccagtc tccttccacc ctgtctgcat ctgtaggaga cagagtcacc        60
atcacttgcc gggccagtca gagtattagt acctggttgg cctggtatca gcagaaacca      120
gggaaagccc ctaagctcct gatctataag gcgtctagtt tagaaagtgg ggtcccatca      180
aggttcagcg gcagtggatc tgggacagaa ttcactctca ccatcagcag cctgcagcct      240
gatgattttg caacttatta ctgccaacag tataatagtt attctacttt cggccctggg      300
accaaagtgg atatcaaa                                                   318

<210> SEQ ID NO 298
<211> LENGTH: 106
<212> TYPE: PRT
<213> ORGANISM: Artificial Sequence
<220> FEATURE:
<223> OTHER INFORMATION: Synthetic

<400> SEQUENCE: 298

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Thr
                 85                  90                  95

Phe Gly Pro Gly Thr Lys Val Asp Ile Lys
            100                 105

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299
cagagtatta gtacctgg                                                      18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Ser Ile Ser Thr Trp
 1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 aaggcgtct                                                                 9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Lys Ala Ser
 1

<210> SEQ ID NO 303
<211> LENGTH: 24
<212> TYPE: DNA
<213> ORGANISM: Artificial Sequence
<220> FEATURE:
<223> OTHER INFORMATION: Synthetic

<400> SEQUENCE: 303
caacagtata atagttattc tact                                              24

<210> SEQ ID NO 304
<211> LENGTH: 8
<212> TYPE: PRT
<213> ORGANISM: Artificial Sequence
<220> FEATURE:
<223> OTHER INFORMATION: Synthetic

<400> SEQUENCE: 304

Gln Gln Tyr Asn Ser Tyr Ser Thr
 1               5

<210> SEQ ID NO 305
<211> LENGTH: 357
<212> TYPE: DNA
<213> ORGANISM: Artificial Sequence
<220> FEATURE:
<223> OTHER INFORMATION: Synthetic

<400> SEQUENCE: 305
gaggtgcagc tggtggagtc tgggggaggc ttggtacagc ctggggggtc cctgagactc        60
tcctgtgcag cctctggatt cgcctttagc agctatgcca tgacctgggt ccgccagact       120
ccagggaagg ggctggagtg ggtctcatct attagtggta gtggtggtag cacatactac       180
gcagactccg tgaagggccg gttcaccatc tccagagaca attccaagaa cacgctgtat       240
ctgcaaatga acagcctgag agccgaggac acggccgtat attactgtgc gaaagctcga       300
actggaaccc atgctttga tatctggggc caagggacaa tggtcaccgt ctcttca          357

<210> SEQ ID NO 306
<211> LENGTH: 119
<212> TYPE: PRT
<213> ORGANISM: Artificial Sequence
<220> FEATURE:
<223> OTHER INFORMATION: Synthetic

<400> SEQUENCE: 306

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Ser Ser Tyr
            20                  25                  30

Ala Met Thr Trp Val Arg Gln Thr Pro Gly Lys Gly Leu Glu Trp Val
        35                  40                  45

Ser Ser Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ala Arg Thr Gly Thr His Ala Phe Asp Ile Trp Gly Gln Gly

```
                      100                 105                 110
Thr Met Val Thr Val Ser Ser
        115
```

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307
ggattcgcct ttagcagcta tgcc     24

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

```
Gly Phe Ala Phe Ser Ser Tyr Ala
1               5
```

<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309
attagtggta gtggtggtag caca     24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

```
Ile Ser Gly Ser Gly Gly Ser Thr
1               5
```

<210> SEQ ID NO 311
<211> LENGTH: 36
<212> TYPE: DNA
<213> ORGANISM: Artificial Sequence
<220> FEATURE:
<223> OTHER INFORMATION: Synthetic

<400> SEQUENCE: 311
gcgaaagctc gaactggaac ccatgctttt gatatc     36

<210> SEQ ID NO 312
<211> LENGTH: 12
<212> TYPE: PRT
<213> ORGANISM: Artificial Sequence
<220> FEATURE:
<223> OTHER INFORMATION: Synthetic

<400> SEQUENCE: 312

```
Ala Lys Ala Arg Thr Gly Thr His Ala Phe Asp Ile
1               5                   10
```

<210> SEQ ID NO 313
<211> LENGTH: 318
<212> TYPE: DNA
<213> ORGANISM: Artificial Sequence
<220> FEATURE:
<223> OTHER INFORMATION: Synthetic

<400> SEQUENCE: 313

```
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attctacttt cggccctggg     300
accaaagtgg atatcaaa                                                   318
```

<210> SEQ ID NO 314
<211> LENGTH: 106
<212> TYPE: PRT
<213> ORGANISM: Artificial Sequence
<220> FEATURE:
<223> OTHER INFORMATION: Synthetic

<400> SEQUENCE: 314

```
Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Thr
                 85                  90                  95

Phe Gly Pro Gly Thr Lys Val Asp Ile Lys
            100                 105
```

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315

```
cagagtatta gtagctgg                                                    18
```

<210> SEQ ID NO 316
<211> LENGTH: 6
<212> TYPE: PRT
<213> ORGANISM: Artificial Sequence
<220> FEATURE:
<223> OTHER INFORMATION: Synthetic

<400> SEQUENCE: 316

```
Gln Ser Ile Ser Ser Trp
  1               5
```

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 aaggcgtct                                                                 9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Lys Ala Ser
 1

<210> SEQ ID NO 319
<211> LENGTH: 24
<212> TYPE: DNA
<213> ORGANISM: Artificial Sequence
<220> FEATURE:
<223> OTHER INFORMATION: Synthetic

<400> SEQUENCE: 319
caacagtata atagttattc tact                                               24

<210> SEQ ID NO 320
<211> LENGTH: 8
<212> TYPE: PRT
<213> ORGANISM: Artificial Sequence
<220> FEATURE:
<223> OTHER INFORMATION: Synthetic

<400> SEQUENCE: 320

Gln Gln Tyr Asn Ser Tyr Ser Thr
 1               5

<210> SEQ ID NO 321
<211> LENGTH: 357
<212> TYPE: DNA
<213> ORGANISM: Artificial Sequence
<220> FEATURE:
<223> OTHER INFORMATION: Synthetic

<400> SEQUENCE: 321
gaggtgcagc tggtggagtc tgggggaggc ttggtacagc ctggggggtc cctgagactc         60
tcctgtgcag cctctggatt cacctttagc agctctgcca tgagctgggt ccgccaggct        120
ccagggaagg ggctggaatg ggtctcagct attagtggta gtggtgttgg cacatactac        180
gcggcctccg tgaagggccg gttcaccatc tccagagaca attccaagaa cattctgtat        240
ctgcaaatga acgacctgag agccgaggac acggccttat attactgtcc gaaagctcga        300
actggaaccc atgctttga tatctggggc caagggacaa tggtcaccgt ctcttca           357

<210> SEQ ID NO 322
<211> LENGTH: 119
<212> TYPE: PRT
<213> ORGANISM: Artificial Sequence
<220> FEATURE:
<223> OTHER INFORMATION: Synthetic

<400> SEQUENCE: 322

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Ala Ile Ser Gly Ser Gly Val Gly Thr Tyr Tyr Ala Ala Ser Val
    50                  55                  60

Lys Gly Arg Phe Thr Ile Ser Arg Asp Asn Ser Lys Asn Ile Leu Tyr
65                  70                  75                  80

Leu Gln Met Asn Asp Leu Arg Ala Glu Asp Thr Ala Leu Tyr Tyr Cys
                85                  90                  95

Pro Lys Ala Arg Thr Gly Thr His Ala Phe Asp Ile Trp Gly Gln Gly
            100                 105                 110

Thr Met Val Thr Val Ser Ser
        115

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323
ggattcacct ttagcagctc tgcc                                    24

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324

Gly Phe Thr Phe Ser Ser Ser Ala
1               5

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
attagtggta gtggtgttgg caca                                    24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Ile Ser Gly Ser Gly Val Gly Thr
1               5

<210> SEQ ID NO 327

<211> LENGTH: 36
<212> TYPE: DNA
<213> ORGANISM: Artificial Sequence
<220> FEATURE:
<223> OTHER INFORMATION: Synthetic

<400> SEQUENCE: 327
ccgaaagctc gaactggaac ccatgctttt gatatc        36

<210> SEQ ID NO 328
<211> LENGTH: 12
<212> TYPE: PRT
<213> ORGANISM: Artificial Sequence
<220> FEATURE:
<223> OTHER INFORMATION: Synthetic

<400> SEQUENCE: 328

Pro Lys Ala Arg Thr Gly Thr His Ala Phe Asp Ile
 1               5                  10

<210> SEQ ID NO 329
<211> LENGTH: 318
<212> TYPE: DNA
<213> ORGANISM: Artificial Sequence
<220> FEATURE:
<223> OTHER INFORMATION: Synthetic

<400> SEQUENCE: 329
gacatccaga tgacccagtc tccttccacc ctgtctgcat ctgtaggaga cagagtcacc        60
atcacttgcc gggccagtca gagtattagt acctggttgg cctggtatca gcagaaacca       120
gggaaagccc ctaagctcct gatctataag gcgtctagtt tagaaagtgg ggtcccatca       180
aggttcagcg gcagtggatc tgggacagaa ttcactctca ccatcagcag cctgcagcct       240
gatgattttg caacttatta ctgccaacag tataatagtt attctacttt cggccctggg       300
accaaagtgg atatcaaa                                                     318

<210> SEQ ID NO 330
<211> LENGTH: 106
<212> TYPE: PRT
<213> ORGANISM: Artificial Sequence
<220> FEATURE:
<223> OTHER INFORMATION: Synthetic

<400> SEQUENCE: 330

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Thr
                85                  90                  95

Phe Gly Pro Gly Thr Lys Val Asp Ile Lys
            100                 105

<210> SEQ ID NO 331
<211> LENGTH: 18

<212> TYPE: DNA
<213> ORGANISM: Artificial Sequence
<220> FEATURE:
<223> OTHER INFORMATION: Synthetic

<400> SEQUENCE: 331
cagagtatta gtacctgg                                             18

<210> SEQ ID NO 332
<211> LENGTH: 6
<212> TYPE: PRT
<213> ORGANISM: Artificial Sequence
<220> FEATURE:
<223> OTHER INFORMATION: Synthetic

<400> SEQUENCE: 332

Gln Ser Ile Ser Thr Trp
 1               5

<210> SEQ ID NO 333
<211> LENGTH: 9
<212> TYPE: DNA
<213> ORGANISM: Artificial Sequence
<220> FEATURE:
<223> OTHER INFORMATION: Synthetic

<400> SEQUENCE: 333 aaggcgtct                                                        9

<210> SEQ ID NO 334
<211> LENGTH: 3
<212> TYPE: PRT
<213> ORGANISM: Artificial Sequence
<220> FEATURE:
<223> OTHER INFORMATION: Synthetic

<400> SEQUENCE: 334

Lys Ala Ser
 1

<210> SEQ ID NO 335
<211> LENGTH: 24
<212> TYPE: DNA
<213> ORGANISM: Artificial Sequence
<220> FEATURE:
<223> OTHER INFORMATION: Synthetic

<400> SEQUENCE: 335
caacagtata atagttattc tact                                      24

<210> SEQ ID NO 336
<211> LENGTH: 8
<212> TYPE: PRT
<213> ORGANISM: Artificial Sequence
<220> FEATURE:
<223> OTHER INFORMATION: Synthetic

<400> SEQUENCE: 336

Gln Gln Tyr Asn Ser Tyr Ser Thr
 1               5

<210> SEQ ID NO 337
<211> LENGTH: 357
<212> TYPE: DNA
<213> ORGANISM: Artificial Sequence
<220> FEATURE:
<223> OTHER INFORMATION: Synthetic

<400> SEQUENCE: 337

```
gaggtgcagt tgttggagtc tgggggaggc ttggtacagc cggggggtc cctgagactc      60
tcctgtgcag cctctggatt cacctttagc agctatgcca tgagttgggt ccgccaggct    120
ccagggaagg ggctggaatg ggtctcagct attagtggta gtggtgttgg cacatactat    180
gcagactccg tgaagggccg gttcaccatc tccagagaca attccaagaa tacgttgtat    240
ctgcaaatga acagcctgag agccgaggac acggccgtat attactgtcc gaaagctcga    300
actggaaccc atgcttttga tatctggggc caagggacaa tggtcaccgt ctcttca       357
```

<210> SEQ ID NO 338
<211> LENGTH: 119
<212> TYPE: PRT
<213> ORGANISM: Artificial Sequence
<220> FEATURE:
<223> OTHER INFORMATION: Synthetic

<400> SEQUENCE: 338

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Val Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Pro Lys Ala Arg Thr Gly Thr His Ala Phe Asp Ile Trp Gly Gln Gly
            100                 105                 110

Thr Met Val Thr Val Ser Ser
        115
```

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339

```
ggattcacct ttagcagcta tgcc                                            24
```

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

```
Gly Phe Thr Phe Ser Ser Tyr Ala
 1               5
```

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
attagtggta gtggtgttgg caca                                              24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ile Ser Gly Ser Gly Val Gly Thr
1               5

<210> SEQ ID NO 343
<211> LENGTH: 36
<212> TYPE: DNA
<213> ORGANISM: Artificial Sequence
<220> FEATURE:
<223> OTHER INFORMATION: Synthetic

<400> SEQUENCE: 343
ccgaaagctc gaactggaac ccatgctttt gatatc                                 36

<210> SEQ ID NO 344
<211> LENGTH: 12
<212> TYPE: PRT
<213> ORGANISM: Artificial Sequence
<220> FEATURE:
<223> OTHER INFORMATION: Synthetic

<400> SEQUENCE: 344

Pro Lys Ala Arg Thr Gly Thr His Ala Phe Asp Ile
1               5                   10

<210> SEQ ID NO 345
<211> LENGTH: 318
<212> TYPE: DNA
<213> ORGANISM: Artificial Sequence
<220> FEATURE:
<223> OTHER INFORMATION: Synthetic

<400> SEQUENCE: 345
gacatccaga tgacccagtc tccttccacc ttgtctgcat ctgtaggaga cagagtcacc        60
atcacttgcc gggccagtca gagtattagt agctggttgg cctggtatca acagaaacca       120
gggaaagccc ctaagctcct gatctataag gcgtctagtt tagaaagtgg ggtcccatca       180
aggttcagcg gcagtggatc tgggacagaa ttcactctca ccatcagcag cctgcagcct       240
gatgattttg caacttatta ctgccaacag tataatagct attctacttt cggccctggg       300
accaaagtgg atatcaaa                                                    318

<210> SEQ ID NO 346
<211> LENGTH: 106
<212> TYPE: PRT
<213> ORGANISM: Artificial Sequence
<220> FEATURE:
<223> OTHER INFORMATION: Synthetic

<400> SEQUENCE: 346

Asp Ile Gln Met Thr Gln Ser Pro Ser Thr Leu Ser Ala Ser Val Gly
1               5                   10                  15

```
Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Thr
                85                  90                  95

Phe Gly Pro Gly Thr Lys Val Asp Ile Lys
            100                 105
```

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347
cagagtatta gtagctgg                                              18

<210> SEQ ID NO 348
<211> LENGTH: 6
<212> TYPE: PRT
<213> ORGANISM: Artificial Sequence
<220> FEATURE:
<223> OTHER INFORMATION: Synthetic

<400> SEQUENCE: 348

```
Gln Ser Ile Ser Ser Trp
 1               5
```

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 aaggcgtct                                                         9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

```
Lys Ala Ser
 1
```

<210> SEQ ID NO 351
<211> LENGTH: 24
<212> TYPE: DNA
<213> ORGANISM: Artificial Sequence
<220> FEATURE:
<223> OTHER INFORMATION: Synthetic

<400> SEQUENCE: 351
caacagtata atagctattc tact 24

<210> SEQ ID NO 352
<211> LENGTH: 8
<212> TYPE: PRT
<213> ORGANISM: Artificial Sequence
<220> FEATURE:
<223> OTHER INFORMATION: Synthetic

<400> SEQUENCE: 352

Gln Gln Tyr Asn Ser Tyr Ser Thr
 1               5

<210> SEQ ID NO 353
<211> LENGTH: 357
<212> TYPE: DNA
<213> ORGANISM: Artificial Sequence
<220> FEATURE:
<223> OTHER INFORMATION: Synthetic

<400> SEQUENCE: 353
gaggtgcagc tggtggagtc tgggggaggc ttggtacagc cggggggtc cctgagactc        60 tcctgtgcag cctctggatt catctttagt agttatgcca tgacttgggt ccgccaggct      120
ccagggaagg ggctggaatg ggtctcagca attagtggta gtggtgttag cacatactac      180
gcagactccg tgaagggccg gttcaccatc tccagagaca attccaagaa cacgctgtat      240
ctgcaaatga acagcctgag aatcgaggac acggccgtat attactgtgg gaaagctcga      300
actggaaccc atgctttga tatctggggc caagggacaa tggtcaccgt ctcttca         357

<210> SEQ ID NO 354
<211> LENGTH: 119
<212> TYPE: PRT
<213> ORGANISM: Artificial Sequence
<220> FEATURE:
<223> OTHER INFORMATION: Synthetic

<400> SEQUENCE: 354

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ile Phe Ser Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ile Glu Asp Thr Ala Val Tyr Tyr Cys
                85                  90                  95

Gly Lys Ala Arg Thr Gly Thr His Ala Phe Asp Ile Trp Gly Gln Gly
            100                 105                 110

Thr Met Val Thr Val Ser Ser
        115

<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355
ggattcatct ttagtagtta tgcc				24

<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

Gly Phe Ile Phe Ser Ser Tyr Ala
1               5

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357
attagtggta gtggtgttag caca				24

<210> SEQ ID NO 358
<211> LENGTH: 8
<212> TYPE: PRT
<213> ORGANISM: Artificial Sequence
<220> FEATURE:
<223> OTHER INFORMATION: Synthetic

<400> SEQUENCE: 358

Ile Ser Gly Ser Gly Val Ser Thr
1               5

<210> SEQ ID NO 359
<211> LENGTH: 36
<212> TYPE: DNA
<213> ORGANISM: Artificial Sequence
<220> FEATURE:
<223> OTHER INFORMATION: Synthetic

<400> SEQUENCE: 359
gggaaagctc gaactggaac ccatgctttt gatatc				36

<210> SEQ ID NO 360
<211> LENGTH: 12
<212> TYPE: PRT
<213> ORGANISM: Artificial Sequence
<220> FEATURE:
<223> OTHER INFORMATION: Synthetic

<400> SEQUENCE: 360

Gly Lys Ala Arg Thr Gly Thr His Ala Phe Asp Ile
1               5                   10

<210> SEQ ID NO 361
<211> LENGTH: 318
<212> TYPE: DNA
<213> ORGANISM: Artificial Sequence
<220> FEATURE:
<223> OTHER INFORMATION: Synthetic

<400> SEQUENCE: 361
gacatccaga tgacccagtc tccttccacc ctgtctgcat ctgtaggaga cagagtcacc				60

```
atcacttgcc gggccagtca gagtattagt aggtggttgg cctggtatca gcagaaacca    120
ggaaaagccc ctaaactcct gatctataag gcgtctagtt tagaaactgg ggtcccatca    180
aggttcagcg gcagtggatc tgggacagaa ttcactctca ccatcagcag cctgcagcct    240
gatgattttg gaacttatta ctgccaacag tataatagtt attctagttt cggccctggg    300
accaaagtgg atatcaaa                                                  318
```

```
<210> SEQ ID NO 362
<211> LENGTH: 106
<212> TYPE: PRT
<213> ORGANISM: Artificial Sequence
<220> FEATURE:
<223> OTHER INFORMATION: Synthetic

<400> SEQUENCE: 362
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Gly Thr Tyr Tyr Cys Gln Gln Tyr Asn Ser Tyr Ser Ser
                85                  90                  95

Phe Gly Pro Gly Thr Lys Val Asp Ile Lys
            100                 105

```
<210> SEQ ID NO 363
<211> LENGTH: 18
<212> TYPE: DNA
<213> ORGANISM: Artificial Sequence
<220> FEATURE:
<223> OTHER INFORMATION: Synthetic

<400> SEQUENCE: 363
cagagtatta gtaggtgg                                                   18
```

```
<210> SEQ ID NO 364
<211> LENGTH: 6
<212> TYPE: PRT
<213> ORGANISM: Artificial Sequence
<220> FEATURE:
<223> OTHER INFORMATION: Synthetic

<400> SEQUENCE: 364
```

Gln Ser Ile Ser Arg Trp
1               5

```
<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 aaggcgtct                                                              9
```

```
<210> SEQ ID NO 366
<211> LENGTH: 3
<212> TYPE: PRT
<213> ORGANISM: Artificial Sequence
<220> FEATURE:
<223> OTHER INFORMATION: Synthetic

<400> SEQUENCE: 366

Lys Ala Ser
 1

<210> SEQ ID NO 367
<211> LENGTH: 24
<212> TYPE: DNA
<213> ORGANISM: Artificial Sequence
<220> FEATURE:
<223> OTHER INFORMATION: Synthetic

<400> SEQUENCE: 367
caacagtata atagttattc tagt                                             24

<210> SEQ ID NO 368
<211> LENGTH: 8
<212> TYPE: PRT
<213> ORGANISM: Artificial Sequence
<220> FEATURE:
<223> OTHER INFORMATION: Synthetic

<400> SEQUENCE: 368

Gln Gln Tyr Asn Ser Tyr Ser Ser
 1               5

<210> SEQ ID NO 369
<211> LENGTH: 357
<212> TYPE: DNA
<213> ORGANISM: Artificial Sequence
<220> FEATURE:
<223> OTHER INFORMATION: Synthetic

<400> SEQUENCE: 369
gaggtgcagc tggtggagtc tgggggaggc ttggtacagc ctggggggtc cctgagactc        60
tcctgtgcag cctctggatt cacctttagc aactatgcca tgagctgggt ccgccaggct       120
ccagggaagg ggctgagtg gtctcagct attagtggta gtggtgttgg cacatactac        180
gcggcctccg tgaagggccg gttcaccatc tccagagaca attccaagaa cactctgtat       240
ctgcaaatga acagcctgag agccgaggac acggccgttt attactgtcc gaaagctcga       300
actggaaccc atgcttttga tatctggggc caaggacaa tggtcaccgt ctcttca         357

<210> SEQ ID NO 370
<211> LENGTH: 119
<212> TYPE: PRT
<213> ORGANISM: Artificial Sequence
<220> FEATURE:
<223> OTHER INFORMATION: Synthetic

<400> SEQUENCE: 370

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Val Gly Thr Tyr Tyr Ala Ala Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                         85                  90                  95

Pro Lys Ala Arg Thr Gly Thr His Ala Phe Asp Ile Trp Gly Gln Gly
                100                 105                 110

Thr Met Val Thr Val Ser Ser
            115

<210> SEQ ID NO 371
<211> LENGTH: 24
<212> TYPE: DNA
<213> ORGANISM: Artificial Sequence
<220> FEATURE:
<223> OTHER INFORMATION: Synthetic

<400> SEQUENCE: 371
ggattcacct ttagcaacta tgcc                                          24

<210> SEQ ID NO 372
<211> LENGTH: 8
<212> TYPE: PRT
<213> ORGANISM: Artificial Sequence
<220> FEATURE:
<223> OTHER INFORMATION: Synthetic

<400> SEQUENCE: 372

Gly Phe Thr Phe Ser Asn Tyr Ala
 1               5

<210> SEQ ID NO 373
<211> LENGTH: 24
<212> TYPE: DNA
<213> ORGANISM: Artificial Sequence
<220> FEATURE:
<223> OTHER INFORMATION: Synthetic

<400> SEQUENCE: 373
attagtggta gtggtgttgg caca                                          24

<210> SEQ ID NO 374
<211> LENGTH: 8
<212> TYPE: PRT
<213> ORGANISM: Artificial Sequence
<220> FEATURE:
<223> OTHER INFORMATION: Synthetic

<400> SEQUENCE: 374

Ile Ser Gly Ser Gly Val Gly Thr
 1               5

<210> SEQ ID NO 375
<211> LENGTH: 36
<212> TYPE: DNA
<213> ORGANISM: Artificial Sequence
<220> FEATURE:
<223> OTHER INFORMATION: Synthetic

<400> SEQUENCE: 375
ccgaaagctc gaactggaac ccatgctttt gatatc                             36

<210> SEQ ID NO 376
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 376

Pro Lys Ala Arg Thr Gly Thr His Ala Phe Asp Ile
 1               5                  10

<210> SEQ ID NO 377
<211> LENGTH: 318
<212> TYPE: DNA
<213> ORGANISM: Artificial Sequence
<220> FEATURE:
<223> OTHER INFORMATION: Synthetic

<400> SEQUENCE: 377
gacatccaga tgacccagtc tccttccacc ctgtctgcat ctgtaggaga cagagtcacc      60
atcacttgcc gggccagtca gagtattagt acctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attctacttt cggccctggg     300
accaaagtgg atatcaaa                                                    318

<210> SEQ ID NO 378
<211> LENGTH: 106
<212> TYPE: PRT
<213> ORGANISM: Artificial Sequence
<220> FEATURE:
<223> OTHER INFORMATION: Synthetic

<400> SEQUENCE: 378

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Thr Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Thr
                 85                  90                  95

Phe Gly Pro Gly Thr Lys Val Asp Ile Lys
            100                 105

<210> SEQ ID NO 379
<211> LENGTH: 18
<212> TYPE: DNA
<213> ORGANISM: Artificial Sequence
<220> FEATURE:
<223> OTHER INFORMATION: Synthetic

<400> SEQUENCE: 379
cagagtatta gtacctgg                                                    18

<210> SEQ ID NO 380
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 380

Gln Ser Ile Ser Thr Trp
1               5

<210> SEQ ID NO 381
<211> LENGTH: 9
<212> TYPE: DNA
<213> ORGANISM: Artificial Sequence
<220> FEATURE:
<223> OTHER INFORMATION: Synthetic

<400> SEQUENCE: 381 aaggcgtct                                                             9

<210> SEQ ID NO 382
<211> LENGTH: 3
<212> TYPE: PRT
<213> ORGANISM: Artificial Sequence
<220> FEATURE:
<223> OTHER INFORMATION: Synthetic

<400> SEQUENCE: 382

Lys Ala Ser
1

<210> SEQ ID NO 383
<211> LENGTH: 24
<212> TYPE: DNA
<213> ORGANISM: Artificial Sequence
<220> FEATURE:
<223> OTHER INFORMATION: Synthetic

<400> SEQUENCE: 383
caacagtata atagttattc tact                                           24

<210> SEQ ID NO 384
<211> LENGTH: 8
<212> TYPE: PRT
<213> ORGANISM: Artificial Sequence
<220> FEATURE:
<223> OTHER INFORMATION: Synthetic

<400> SEQUENCE: 384

Gln Gln Tyr Asn Ser Tyr Ser Thr
1               5

<210> SEQ ID NO 385
<211> LENGTH: 345
<212> TYPE: DNA
<213> ORGANISM: Artificial Sequence
<220> FEATURE:
<223> OTHER INFORMATION: Synthetic

<400> SEQUENCE: 385
gaggtgcagc tggtggagtc tgggggaggc ctggtaaagc ctggggggtc ccttagactc      60
tcctgtgcag cctctggatt cagtttcaat tacgcctgga tgagttgggt ccgccaggct     120
ccaggaaagg ggctggagtg gattggccgt attaagagca aaattaatgg tgggacaaca     180
gactacactg cacccgtgaa aggcagattc accatctcac gagatgattc aaaaaacacg     240
ctgtatctgc aaatgaacag cctgaaaacc gaggacacag ccgtgtatta ctgtagggt      300
```
gatgaggact tctggggcca gggaaccctg gtcactgtct cctca 345

<210> SEQ ID NO 386
<211> LENGTH: 115
<212> TYPE: PRT
<213> ORGANISM: Artificial Sequence
<220> FEATURE:
<223> OTHER INFORMATION: Synthetic

<400> SEQUENCE: 386

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Ser Phe Asn Tyr Ala
            20                  25                  30
Trp Met Ser Trp Val Arg Gln Ala Pro Gly Lys Gly Leu Glu Trp Ile
        35                  40                  45
Gly Arg Ile Lys Ser Lys Ile Asn Gly Gly Thr Thr Asp Tyr Thr Ala
    50                  55                  60
Pro Val Lys Gly Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
                85                  90                  95
Tyr Cys Arg Gly Asp Glu Asp Phe Trp Gly Gln Gly Thr Leu Val Thr
            100                 105                 110
Val Ser Ser
        115

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387
ggattcagtt tcaattacgc ctgg 24

<210> SEQ ID NO 388
<211> LENGTH: 8
<212> TYPE: PRT
<213> ORGANISM: Artificial Sequence
<220> FEATURE:
<223> OTHER INFORMATION: Synthetic

<400> SEQUENCE: 388

Gly Phe Ser Phe Asn Tyr Ala Trp
1               5

<210> SEQ ID NO 389
<211> LENGTH: 30
<212> TYPE: DNA
<213> ORGANISM: Artificial Sequence
<220> FEATURE:
<223> OTHER INFORMATION: Synthetic

<400> SEQUENCE: 389
attaagagca aaattaatgg tgggacaaca 30

<210> SEQ ID NO 390
<211> LENGTH: 10
<212> TYPE: PRT
<213> ORGANISM: Artificial Sequence
<220> FEATURE:

<223> OTHER INFORMATION: Synthetic

<400> SEQUENCE: 390

Ile Lys Ser Lys Ile Asn Gly Gly Thr Thr
1               5                   10

<210> SEQ ID NO 391
<211> LENGTH: 18
<212> TYPE: DNA
<213> ORGANISM: Artificial Sequence
<220> FEATURE:
<223> OTHER INFORMATION: Synthetic

<400> SEQUENCE: 391
aggggtgatg aggacttc                                                   18

<210> SEQ ID NO 392
<211> LENGTH: 6
<212> TYPE: PRT
<213> ORGANISM: Artificial Sequence
<220> FEATURE:
<223> OTHER INFORMATION: Synthetic

<400> SEQUENCE: 392

Arg Gly Asp Glu Asp Phe
1               5

<210> SEQ ID NO 393
<211> LENGTH: 336
<212> TYPE: DNA
<213> ORGANISM: Artificial Sequence
<220> FEATURE:
<223> OTHER INFORMATION: Synthetic

<400> SEQUENCE: 393
gatgttgtga tgactcagtc tccactctcc ctgcccgtca cccttggaca gccggcctcc     60
atctcctgca ggtctagtca aagcctcgta tacagtgatg gattcaccta cttgaattgg   120
tttcggcaga ggccaggcca atctccaagg cgcctaattt ataaggtttc taaccgggac   180
tctggggtcc cagacagatt cagcggcagt gggtcaggca ctgatttcac actgagaatc   240
agcagggtgg aggctgagga tgttgggatt tattactgca tgcaaggtac acactggccg   300
tacacttttg gccaggggac caagctggag atcaaa                             336

<210> SEQ ID NO 394
<211> LENGTH: 112
<212> TYPE: PRT
<213> ORGANISM: Artificial Sequence
<220> FEATURE:
<223> OTHER INFORMATION: Synthetic

<400> SEQUENCE: 394

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Phe Thr Tyr Leu Asn Trp Phe Arg Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Gly
            85                  90                  95

Thr His Trp Pro Tyr Thr Phe Gly Gln Gly Thr Lys Leu Glu Ile Lys
            100                 105                 110

<210> SEQ ID NO 395
<211> LENGTH: 33
<212> TYPE: DNA
<213> ORGANISM: Artificial Sequence
<220> FEATURE:
<223> OTHER INFORMATION: Synthetic

<400> SEQUENCE: 395
caaagcctcg tatacagtga tggattcacc tac                                    33

<210> SEQ ID NO 396
<211> LENGTH: 11
<212> TYPE: PRT
<213> ORGANISM: Artificial Sequence
<220> FEATURE:
<223> OTHER INFORMATION: Synthetic

<400> SEQUENCE: 396

Gln Ser Leu Val Tyr Ser Asp Gly Phe Thr Tyr
1               5                   10

<210> SEQ ID NO 397
<211> LENGTH: 9
<212> TYPE: DNA
<213> ORGANISM: Artificial Sequence
<220> FEATURE:
<223> OTHER INFORMATION: Synthetic

<400> SEQUENCE: 397 aaggtttct                                                                9

<210> SEQ ID NO 398
<211> LENGTH: 3
<212> TYPE: PRT
<213> ORGANISM: Artificial Sequence
<220> FEATURE:
<223> OTHER INFORMATION: Synthetic

<400> SEQUENCE: 398

Lys Val Ser
1

<210> SEQ ID NO 399
<211> LENGTH: 27
<212> TYPE: DNA
<213> ORGANISM: Artificial Sequence
<220> FEATURE:
<223> OTHER INFORMATION: Synthetic

<400> SEQUENCE: 399
atgcaaggta cacactggcc gtacact                                           27

<210> SEQ ID NO 400
<211> LENGTH: 9
<212> TYPE: PRT
<213> ORGANISM: Artificial Sequence
<220> FEATURE:
<223> OTHER INFORMATION: Synthetic

<400> SEQUENCE: 400

Met Gln Gly Thr His Trp Pro Tyr Thr

<210> SEQ ID NO 401
<211> LENGTH: 366
<212> TYPE: DNA
<213> ORGANISM: Artificial Sequence
<220> FEATURE:
<223> OTHER INFORMATION: Synthetic

<400> SEQUENCE: 401

```
gaagtgcagt tgttggagtc tgggggggc ttggtacagc ctggggggtc cctgagactc      60
tcctgtgcag cctctggatt caccttttagc agctatgcca tgacctgggt ccgccaggct    120
ccagggaagg ggctggagtg gatctcagct attagtggca gtggttatag cacatactac    180
gcagactcca tgaagggccg gttctccatc tccagagaca attccaagaa cacgctgtat    240
ctgcaaatga accgcctgag agccgaggac acggccgttt attactgtac gaaggggggc    300
cgaattttgg agtggttatt acccttttgac ttctggggcc agggaaccct ggtcaccgtc    360
tcctca                                                                366
```

<210> SEQ ID NO 402
<211> LENGTH: 122
<212> TYPE: PRT
<213> ORGANISM: Artificial Sequence
<220> FEATURE:
<223> OTHER INFORMATION: Synthetic

<400> SEQUENCE: 402

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Ala Met Thr Trp Val Arg Gln Ala Pro Gly Lys Gly Leu Glu Trp Ile
        35                  40                  45
Ser Ala Ile Ser Gly Ser Gly Tyr Ser Thr Tyr Tyr Ala Asp Ser Met
    50                  55                  60
Lys Gly Arg Phe Ser Ile Ser Arg Asp Asn Ser Lys Asn Thr Leu Tyr
65                  70                  75                  80
Leu Gln Met Asn Arg Leu Arg Ala Glu Asp Thr Ala Val Tyr Tyr Cys
                85                  90                  95
Thr Lys Gly Gly Arg Ile Leu Glu Trp Leu Leu Pro Phe Asp Phe Trp
            100                 105                 110
Gly Gln Gly Thr Leu Val Thr Val Ser Ser
        115                 120
```

<210> SEQ ID NO 403
<211> LENGTH: 24
<212> TYPE: DNA
<213> ORGANISM: Artificial Sequence
<220> FEATURE:
<223> OTHER INFORMATION: Synthetic

<400> SEQUENCE: 403

```
ggattcacct ttagcagcta tgcc                                            24
```

<210> SEQ ID NO 404
<211> LENGTH: 8
<212> TYPE: PRT
<213> ORGANISM: Artificial Sequence
<220> FEATURE:
<223> OTHER INFORMATION: Synthetic
```

<400> SEQUENCE: 404

Gly Phe Thr Phe Ser Ser Tyr Ala
 1               5

<210> SEQ ID NO 405
<211> LENGTH: 24
<212> TYPE: DNA
<213> ORGANISM: Artificial Sequence
<220> FEATURE:
<223> OTHER INFORMATION: Synthetic

<400> SEQUENCE: 405
attagtggca gtggttatag caca                                          24

<210> SEQ ID NO 406
<211> LENGTH: 8
<212> TYPE: PRT
<213> ORGANISM: Artificial Sequence
<220> FEATURE:
<223> OTHER INFORMATION: Synthetic

<400> SEQUENCE: 406

Ile Ser Gly Ser Gly Tyr Ser Thr
 1               5

<210> SEQ ID NO 407
<211> LENGTH: 45
<212> TYPE: DNA
<213> ORGANISM: Artificial Sequence
<220> FEATURE:
<223> OTHER INFORMATION: Synthetic

<400> SEQUENCE: 407
acgaaagggg gccgaatttt ggagtggtta ttaccctttg acttc                   45

<210> SEQ ID NO 408
<211> LENGTH: 15
<212> TYPE: PRT
<213> ORGANISM: Artificial Sequence
<220> FEATURE:
<223> OTHER INFORMATION: Synthetic

<400> SEQUENCE: 408

Thr Lys Gly Gly Arg Ile Leu Glu Trp Leu Leu Pro Phe Asp Phe
 1               5                  10                  15

<210> SEQ ID NO 409
<211> LENGTH: 336
<212> TYPE: DNA
<213> ORGANISM: Artificial Sequence
<220> FEATURE:
<223> OTHER INFORMATION: Synthetic

<400> SEQUENCE: 409
gatgttgtga tgactcagtc tccactctcc ctgcccgtca cccttggaca gccggcctcc    60
atctcctgcc ggtctagtca aagcctcgta tacagtgatg gaaacaccta cttgatttgg   120
tttcagcaga ggccaggcca atctccaagg cgcctaattt ataaggtttc taaccgggac   180
tctggggtcc cagacagatt cagcggcagt gggtcaggca ctgatttcac actgataatc   240
agcagggtgg aggctgagga tgttggggctt tattactgca tgcaaggtac acactggcct   300
cctactttcg gcggagggac caaggtggag atcaaa                            336

```
<210> SEQ ID NO 410
<211> LENGTH: 112
<212> TYPE: PRT
<213> ORGANISM: Artificial Sequence
<220> FEATURE:
<223> OTHER INFORMATION: Synthetic

<400> SEQUENCE: 410
```

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ile Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Ile Ile
65                  70                  75                  80

Ser Arg Val Glu Ala Glu Asp Val Gly Leu Tyr Tyr Cys Met Gln Gly
                85                  90                  95

Thr His Trp Pro Pro Thr Phe Gly Gly Gly Thr Lys Val Glu Ile Lys
            100                 105                 110

```
<210> SEQ ID NO 411
<211> LENGTH: 33
<212> TYPE: DNA
<213> ORGANISM: Artificial Sequence
<220> FEATURE:
<223> OTHER INFORMATION: Synthetic

<400> SEQUENCE: 411
caaagcctcg tatacagtga tggaaacacc tac                               33

<210> SEQ ID NO 412
<211> LENGTH: 11
<212> TYPE: PRT
<213> ORGANISM: Artificial Sequence
<220> FEATURE:
<223> OTHER INFORMATION: Synthetic

<400> SEQUENCE: 412
```

Gln Ser Leu Val Tyr Ser Asp Gly Asn Thr Tyr
1               5                   10

```
<210> SEQ ID NO 413
<211> LENGTH: 9
<212> TYPE: DNA
<213> ORGANISM: Artificial Sequence
<220> FEATURE:
<223> OTHER INFORMATION: Synthetic

<400> SEQUENCE: 413 aaggtttct                                                          9

<210> SEQ ID NO 414
<211> LENGTH: 3
<212> TYPE: PRT
<213> ORGANISM: Artificial Sequence
<220> FEATURE:
<223> OTHER INFORMATION: Synthetic

<400> SEQUENCE: 414
```

Lys Val Ser
1

<210> SEQ ID NO 415
<211> LENGTH: 27
<212> TYPE: DNA
<213> ORGANISM: Artificial Sequence
<220> FEATURE:
<223> OTHER INFORMATION: Synthetic

<400> SEQUENCE: 415
atgcaaggta cacactggcc tcctact      27

<210> SEQ ID NO 416
<211> LENGTH: 9
<212> TYPE: PRT
<213> ORGANISM: Artificial Sequence
<220> FEATURE:
<223> OTHER INFORMATION: Synthetic

<400> SEQUENCE: 416

Met Gln Gly Thr His Trp Pro Pro Thr
 1               5

<210> SEQ ID NO 417
<211> LENGTH: 345
<212> TYPE: DNA
<213> ORGANISM: Artificial Sequence
<220> FEATURE:
<223> OTHER INFORMATION: Synthetic

<400> SEQUENCE: 417
gaggtgcagc tggtggagtc tgggggaggc ttggtaaagc ctggggggtc ccttagagtc      60
tcctgtgtag cctctggatt cacttttagt aacgcctgga tgacctgggt ccgccagact     120
ccagggaagg ggctgagtg ggttggccgt attaaaagca gaactgatgg tgggacagtt     180
gactatgttg cacccgtgaa aggcagattc accatctcaa gagatgattc aaaaaacacg     240
ctgtatctgc aaatgaacag cctgaaagcc gaggacacag ccgttttatta ctgtagggct     300 gaccttgact actggggcca gggaaccctg gtcaccgttt cctca                    345

<210> SEQ ID NO 418
<211> LENGTH: 115
<212> TYPE: PRT
<213> ORGANISM: Artificial Sequence
<220> FEATURE:
<223> OTHER INFORMATION: Synthetic

<400> SEQUENCE: 418

Glu Val Gln Leu Val Glu Ser Gly Gly Gly Leu Val Lys Pro Gly Gly
 1               5                  10                  15

Ser Leu Arg Val Ser Cys Val Ala Ser Gly Phe Thr Phe Ser Asn Ala
                20                  25                  30

Trp Met Thr Trp Val Arg Gln Thr Pro Gly Lys Gly Leu Glu Trp Val
            35                  40                  45

Gly Arg Ile Lys Ser Arg Thr Asp Gly Gly Thr Val Asp Tyr Val Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Ala Glu Asp Thr Ala Val Tyr
                85                  90                  95

Tyr Cys Arg Ala Asp Leu Asp Tyr Trp Gly Gln Gly Thr Leu Val Thr
            100                 105                 110

Val Ser Ser
        115

<210> SEQ ID NO 419
<211> LENGTH: 24
<212> TYPE: DNA
<213> ORGANISM: Artificial Sequence
<220> FEATURE:
<223> OTHER INFORMATION: Synthetic

<400> SEQUENCE: 419
ggattcactt ttagtaacgc ctgg                                    24

<210> SEQ ID NO 420
<211> LENGTH: 8
<212> TYPE: PRT
<213> ORGANISM: Artificial Sequence
<220> FEATURE:
<223> OTHER INFORMATION: Synthetic

<400> SEQUENCE: 420

Gly Phe Thr Phe Ser Asn Ala Trp
1               5

<210> SEQ ID NO 421
<211> LENGTH: 30
<212> TYPE: DNA
<213> ORGANISM: Artificial Sequence
<220> FEATURE:
<223> OTHER INFORMATION: Synthetic

<400> SEQUENCE: 421
attaaaagca gaactgatgg tgggacagtt                              30

<210> SEQ ID NO 422
<211> LENGTH: 10
<212> TYPE: PRT
<213> ORGANISM: Artificial Sequence
<220> FEATURE:
<223> OTHER INFORMATION: Synthetic

<400> SEQUENCE: 422

Ile Lys Ser Arg Thr Asp Gly Gly Thr Val
1               5                   10

<210> SEQ ID NO 423
<211> LENGTH: 18
<212> TYPE: DNA
<213> ORGANISM: Artificial Sequence
<220> FEATURE:
<223> OTHER INFORMATION: Synthetic

<400> SEQUENCE: 423
agggctgacc ttgactac                                           18

<210> SEQ ID NO 424
<211> LENGTH: 6
<212> TYPE: PRT
<213> ORGANISM: Artificial Sequence
<220> FEATURE:
<223> OTHER INFORMATION: Synthetic

<400> SEQUENCE: 424

Arg Ala Asp Leu Asp Tyr
1               5

<210> SEQ ID NO 425
<211> LENGTH: 336
<212> TYPE: DNA
<213> ORGANISM: Artificial Sequence
<220> FEATURE:
<223> OTHER INFORMATION: Synthetic

<400> SEQUENCE: 425

```
gatgttgtga tgactcagtc tccactctcc ctgcccgtct cccttggaca gccggcctcc    60
atctcctgca ggtctagtca aagcctcgta cacagtgatg gaatcaccta cttgaattgg   120
tttcagcaga ggccaggcca atctccaagg cgcctaattt ataagatttc taaccgggac   180
tctggggtcc cagacagatt cagcggcagt gggtcaggca ctgatttcac actgaaattc   240
agcagggtgg aggctgagga tgttggggtt tatttctgca tgcaaggtac acactggccg   300
tacacttttg gccaggggac caagctggag atcaaa                              336
```

<210> SEQ ID NO 426
<211> LENGTH: 112
<212> TYPE: PRT
<213> ORGANISM: Artificial Sequence
<220> FEATURE:
<223> OTHER INFORMATION: Synthetic

<400> SEQUENCE: 426

```
Asp Val Val Met Thr Gln Ser Pro Leu Ser Leu Pro Val Ser Leu Gly
 1               5                  10                  15
Gln Pro Ala Ser Ile Ser Cys Arg Ser Ser Gln Ser Leu Val His Ser
             20                  25                  30
Asp Gly Ile Thr Tyr Leu Asn Trp Phe Gln Gln Arg Pro Gly Gln Ser
         35                  40                  45
Pro Arg Arg Leu Ile Tyr Lys Ile Ser Asn Arg Asp Ser Gly Val Pro
     50                  55                  60
Asp Arg Phe Ser Gly Ser Gly Ser Gly Thr Asp Phe Thr Leu Lys Phe
 65                  70                  75                  80
Ser Arg Val Glu Ala Glu Asp Val Gly Val Tyr Phe Cys Met Gln Gly
                 85                  90                  95
Thr His Trp Pro Tyr Thr Phe Gly Gln Gly Thr Lys Leu Glu Ile Lys
                100                 105                 110
```

<210> SEQ ID NO 427
<211> LENGTH: 33
<212> TYPE: DNA
<213> ORGANISM: Artificial Sequence
<220> FEATURE:
<223> OTHER INFORMATION: Synthetic

<400> SEQUENCE: 427

```
caaagcctcg tacacagtga tggaatcacc tac                                 33
```

<210> SEQ ID NO 428
<211> LENGTH: 11
<212> TYPE: PRT
<213> ORGANISM: Artificial Sequence
<220> FEATURE:
<223> OTHER INFORMATION: Synthetic

<400> SEQUENCE: 428

```
Gln Ser Leu Val His Ser Asp Gly Ile Thr Tyr
 1               5                  10
```

<210> SEQ ID NO 429

<210> SEQ ID NO 429
<211> LENGTH: 9
<212> TYPE: DNA
<213> ORGANISM: Artificial Sequence
<220> FEATURE:
<223> OTHER INFORMATION: Synthetic

<400> SEQUENCE: 429 aagatttct                                                                                              9

<210> SEQ ID NO 430
<211> LENGTH: 3
<212> TYPE: PRT
<213> ORGANISM: Artificial Sequence
<220> FEATURE:
<223> OTHER INFORMATION: Synthetic

<400> SEQUENCE: 430

Lys Ile Ser
 1

<210> SEQ ID NO 431
<211> LENGTH: 27
<212> TYPE: DNA
<213> ORGANISM: Artificial Sequence
<220> FEATURE:
<223> OTHER INFORMATION: Synthetic

<400> SEQUENCE: 431
atgcaaggta cacactggcc gtacact                                                                         27

<210> SEQ ID NO 432
<211> LENGTH: 9
<212> TYPE: PRT
<213> ORGANISM: Artificial Sequence
<220> FEATURE:
<223> OTHER INFORMATION: Synthetic

<400> SEQUENCE: 432

Met Gln Gly Thr His Trp Pro Tyr Thr
 1               5

<210> SEQ ID NO 433
<211> LENGTH: 212
<212> TYPE: PRT
<213> ORGANISM: Homo sapiens

<400> SEQUENCE: 433

Met Asp Tyr Leu Leu Met Ile Phe Ser Leu Leu Phe Val Ala Cys Gln
 1               5                  10                  15

Gly Ala Pro Glu Thr Ala Val Leu Gly Ala Glu Leu Ser Ala Val Gly
             20                  25                  30

Glu Asn Gly Gly Glu Lys Pro Thr Pro Ser Pro Pro Trp Arg Leu Arg
         35                  40                  45

Arg Ser Lys Arg Cys Ser Cys Ser Ser Leu Met Asp Lys Glu Cys Val
     50                  55                  60

Tyr Phe Cys His Leu Asp Ile Ile Trp Val Asn Thr Pro Glu His Val
 65                  70                  75                  80

Val Pro Tyr Gly Leu Gly Ser Pro Arg Ser Lys Arg Ala Leu Glu Asn
                 85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
        115                 120                 125

Leu Arg Ala Glu Asp Ile Met Glu Lys Asp Trp Asn Asn His Lys Lys
130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu Glu His Leu Arg Gln
            165                 170                 175

Thr Arg Ser Glu Thr Met Arg Asn Ser Val Lys Ser Ser Phe His Asp
        180                 185                 190

Pro Lys Leu Lys Gly Lys Pro Ser Arg Glu Arg Tyr Val Thr His Asn
    195                 200                 205

Arg Ala His Trp
    210

<210> SEQ ID NO 434
<211> LENGTH: 38
<212> TYPE: PRT
<213> ORGANISM: Homo sapiens

<400> SEQUENCE: 434

Cys Ser Cys Ser Ser Leu Met Asp Lys Glu Cys Val Tyr Phe Cys His
1               5                   10                  15

Leu Asp Ile Ile Trp Val Asn Thr Pro Glu His Val Val Pro Tyr Gly
            20                  25                  30

Leu Gly Ser Pro Arg Ser
        35

<210> SEQ ID NO 435
<211> LENGTH: 21
<212> TYPE: PRT
<213> ORGANISM: Homo sapiens

<400> SEQUENCE: 435

Cys Ser Cys Ser Ser Leu Met Asp Lys Glu Cys Val Tyr Phe Cys His
1               5                   10                  15

Leu Asp Ile Ile Trp
            20

<210> SEQ ID NO 436
<211> LENGTH: 754
<212> TYPE: PRT
<213> ORGANISM: Homo sapiens

<400> SEQUENCE: 436

Met Met Ser Thr Tyr Lys Arg Ala Thr Leu Asp Glu Glu Asp Leu Val
1               5                   10                  15

Asp Ser Leu Ser Glu Gly Asp Ala Tyr Pro Asn Gly Leu Gln Val Asn
            20                  25                  30

Phe His Ser Pro Arg Ser Gly Gln Arg Cys Trp Ala Ala Arg Thr Gln
        35                  40                  45

Val Glu Lys Arg Leu Val Val Leu Val Leu Leu Ala Ala Gly Leu
    50                  55                  60

Val Ala Cys Leu Ala Ala Leu Gly Ile Gln Tyr Gln Thr Arg Ser Pro
65                  70                  75                  80

Ser Val Cys Leu Ser Glu Ala Cys Val Ser Val Thr Ser Ser Ile Leu
                85                  90                  95

Ser Ser Met Asp Pro Thr Val Asp Pro Cys His Asp Phe Phe Ser Tyr
            100                 105                 110

-continued

Ala Cys Gly Gly Trp Ile Lys Ala Asn Pro Val Pro Asp Gly His Ser
115                 120                 125

Arg Trp Gly Thr Phe Ser Asn Leu Trp Glu His Asn Gln Ala Ile Ile
130                 135                 140

Lys His Leu Leu Glu Asn Ser Thr Ala Ser Val Ser Glu Ala Glu Arg
145                 150                 155                 160

Lys Ala Gln Val Tyr Tyr Arg Ala Cys Met Asn Glu Thr Arg Ile Glu
                165                 170                 175

Glu Leu Arg Ala Lys Pro Leu Met Glu Leu Ile Glu Arg Leu Gly Gly
            180                 185                 190

Trp Asn Ile Thr Gly Pro Trp Ala Lys Asp Asn Phe Gln Asp Thr Leu
        195                 200                 205

Gln Val Val Thr Ala His Tyr Arg Thr Ser Pro Phe Ser Val Tyr
    210                 215                 220

Val Ser Ala Asp Ser Lys Asn Ser Asn Ser Asn Val Ile Gln Val Asp
225                 230                 235                 240

Gln Ser Gly Leu Gly Leu Pro Ser Arg Asp Tyr Tyr Leu Asn Lys Thr
                245                 250                 255

Glu Asn Glu Lys Val Leu Thr Gly Tyr Leu Asn Tyr Met Val Gln Leu
            260                 265                 270

Gly Lys Leu Leu Gly Gly Gly Asp Glu Glu Ala Ile Arg Pro Gln Met
        275                 280                 285

Gln Gln Ile Leu Asp Phe Glu Thr Ala Leu Ala Asn Ile Thr Ile Pro
    290                 295                 300

Gln Glu Lys Arg Arg Asp Glu Glu Leu Ile Tyr His Lys Val Thr Ala
305                 310                 315                 320

Ala Glu Leu Gln Thr Leu Ala Pro Ala Ile Asn Trp Leu Pro Phe Leu
                325                 330                 335

Asn Thr Ile Phe Tyr Pro Val Glu Ile Asn Glu Ser Glu Pro Ile Val
            340                 345                 350

Val Tyr Asp Lys Glu Tyr Leu Glu Gln Ile Ser Thr Leu Ile Asn Thr
        355                 360                 365

Thr Asp Arg Cys Leu Leu Asn Asn Tyr Met Ile Trp Asn Leu Val Arg
370                 375                 380

Lys Thr Ser Ser Phe Leu Asp Gln Arg Phe Gln Asp Ala Asp Glu Lys
385                 390                 395                 400

Phe Met Glu Val Met Tyr Gly Thr Lys Lys Thr Cys Leu Pro Arg Trp
                405                 410                 415

Lys Phe Cys Val Ser Asp Thr Glu Asn Asn Leu Gly Phe Ala Leu Gly
            420                 425                 430

Pro Met Phe Val Lys Ala Thr Phe Ala Glu Asp Ser Lys Ser Ile Ala
        435                 440                 445

Thr Glu Ile Ile Leu Glu Ile Lys Lys Ala Phe Glu Glu Ser Leu Ser
450                 455                 460

Thr Leu Lys Trp Met Asp Glu Glu Thr Arg Lys Ser Ala Lys Glu Lys
465                 470                 475                 480

Ala Asp Ala Ile Tyr Asn Met Ile Gly Tyr Pro Asn Phe Ile Met Asp
                485                 490                 495

Pro Lys Glu Leu Asp Lys Val Phe Asn Asp Tyr Thr Ala Val Pro Asp
            500                 505                 510

Leu Tyr Phe Glu Asn Ala Met Arg Phe Phe Asn Phe Ser Trp Arg Val
        515                 520                 525

Thr Ala Asp Gln Leu Arg Lys Ala Pro Asn Arg Asp Gln Trp Ser Met

```
                    530                 535                 540
Thr Pro Pro Met Val Asn Ala Tyr Tyr Ser Pro Thr Lys Asn Glu Ile
545                     550                 555                 560

Val Phe Pro Ala Gly Ile Leu Gln Ala Pro Phe Tyr Thr Arg Ser Ser
                565                 570                 575

Pro Lys Ala Leu Asn Phe Gly Gly Ile Gly Val Val Gly His Glu
                580                 585                 590

Leu Thr His Ala Phe Asp Asp Gln Gly Arg Glu Tyr Asp Lys Asp Gly
            595                 600                 605

Asn Leu Arg Pro Trp Trp Lys Asn Ser Ser Val Glu Ala Phe Lys Arg
            610                 615                 620

Gln Thr Glu Cys Met Val Glu Gln Tyr Ser Asn Tyr Ser Val Asn Gly
625                 630                 635                 640

Glu Pro Val Asn Gly Arg His Thr Leu Gly Glu Asn Ile Ala Asp Asn
                645                 650                 655

Gly Gly Leu Lys Ala Ala Tyr Arg Ala Tyr Gln Asn Trp Val Lys Lys
                660                 665                 670

Asn Gly Ala Glu His Ser Leu Pro Thr Leu Gly Leu Thr Asn Asn Gln
            675                 680                 685

Leu Phe Phe Leu Gly Phe Ala Gln Val Trp Cys Ser Val Arg Thr Pro
            690                 695                 700

Glu Ser His Glu Gly Leu Ile Thr Asp Pro His Ser Pro Ser Arg
705                 710                 715                 720

Phe Arg Val Ile Gly Ser Leu Ser Asn Ser Lys Glu Phe Ser Glu His
                725                 730                 735

Phe Arg Cys Pro Pro Gly Ser Pro Met Asn Pro Pro His Lys Cys Glu
                740                 745                 750

Val Trp

<210> SEQ ID NO 437
<211> LENGTH: 39
<212> TYPE: PRT
<213> ORGANISM: Homo sapiens

<400> SEQUENCE: 437

Cys Ser Cys Ser Ser Leu Met Asp Lys Glu Cys Val Tyr Phe Cys His
1               5                   10                  15

Leu Asp Ile Ile Trp Val Asn Thr Pro Glu Arg Val Val Pro Tyr Gly
                20                  25                  30

Leu Gly Gly Ser Ser Arg Ser
            35
```

ANTI-BIG-ENDOTHELIN-1 (BIG-ET-1) ANTIBODIES AND USES THEREOF

FIELD OF THE INVENTION

The present invention relates to antibodies, and antigen-binding fragments thereof, which are specific for human big-endothelin-1.

BACKGROUND

Endothelin-1 (also referred to as "ET-1", "small-ET-1", and "EDN1") is a 21 amino acid vasoconstrictor agent that was originally isolated and characterized from culture medium of porcine aortic endothelial cells. (Yanagisawa et al. (1988) *Nature* 332:411-415). ET-1 is derived from a ~200 amino acid prepro-ET-1 molecule which is cleaved by an endopeptidase to produce a 38 amino acid form called "big-ET-1" (also referred to as "pro-ET-1"). Big-ET-1 is further cleaved by endothelin converting enzyme (ECE-1) to produce the vasoactive 21 amino acid ET-1 peptide. ET-1 can activate endothelin receptors type-A ("ETaR") and type-B ("ETbR"). Activation of ETaR or ETbR in smooth muscle cells results in vasoconstriction, and intravenous administration of ET-1 to experimental animal models causes sustained elevation of arterial pressure. In the lung, endothelin gene expression is upregulated by hypoxia, leading to a feed-forward effect on vascular smooth muscle hypertrophy, vasoconstriction, inflammation and cardiac hypertrophy, and fibrosis in pulmonary hypertension.

Consistent with the foregoing properties, endothelin-1 has been implicated in various diseases and disorders including, e.g., pulmonary hypertension, heart failure, systemic hypertension, fibrotic diseases, neurodegenerative diseases, and cancer. For example, ET-1, the product of Big-ET-1 cleavage, is thought to be involved in the pathogenesis of pulmonary fibrosis due to its ability to induce fibroblast proliferation as well as stimulating collagen metabolism (see Fonseca et al. (2011) *Am J Respir Cell Mol Biol* 44:1-10). Elevated endothelin-1 levels have also been linked to eye diseases (e.g., glaucoma [e.g., normal tension glaucoma, hypertensive glaucoma, open angle glaucoma]) (see Sugiyama et al. (1995) *Surv Ophthalmol* 39 Suppl 1:S49-56; Emre et al. (2005) *Br J Ophthalmol* 89:60-63; Galassi et al. (2011) *Invest Opthalmol Vis Sci* 52:4467-4471; Ghanem et al. (2011) *Ophthalmic Res* 46:98-102; Tezel et al. (1997) *J. Glaucoma* 6:83-89; Chauhan (2008) *Can J Ophthalmol* 43:356-360). Accordingly, several small molecule antagonists of endothelin receptors ($ET_A$ and $ET_B$) have been tested or proposed for the treatment of disorders such as pulmonary hypertension, cardiovascular disorders, inflammatory diseases, kidney diseases, cancers, and Alzheimer's disease.

Anti-ET-1 antibodies are mentioned in EP0406628B1; however, the antibodies of EP0406628B1 were raised against synthetic ET-1 (i.e., small-ET-1) conjugated to bovine thyroglobulin. Since small-ET-1 was used as the immunogen, the antibodies of EP0406628B1 would not be expected to bind big-ET-1, nor are they expected to have the ability to reduce or inhibit the cleavage of big-ET-1 by endothelin converting enzyme. A therapeutic agent which blocks the cleavage of big-ET-1 into small-ET-1 would act at an earlier point in the endothelin signaling process and thereby potentially provide more robust inhibitory activity than an antibody specific for ET-1 per se. Thus, there remains a need in the art for novel inhibitors of endothelin signaling, including antibodies that specifically bind human big-ET-1 and block the formation of small-ET-1.

BRIEF SUMMARY OF THE INVENTION

The present invention provides antibodies that bind human big-ET-1. The antibodies of the invention are useful, inter alia, for inhibiting ET-1-mediated signaling and for treating diseases and disorders caused by or related to ET-1 activity and/or signaling.

The antibodies of the present invention, according to certain embodiments, specifically bind human big-ET-1 but do not bind human small-ET-1. The present invention also provides antibodies that block endothelin-converting enzyme-1 (ECE-1)-mediated cleavage of big-ET-1. As illustrated herein, anti-big-ET-1 antibodies which block ECE-1-mediated cleavage of big-ET-1 are potent inhibitors of endothelin-1 activity both in vitro and in vivo.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., (2000) *J. Immunol.* 164:1925-1933).

The present invention provides an antibody or antigen-binding fragment of an antibody comprising a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 370, 386, 402, and 418, or a substantially similar sequence thereof having at least 90%, at least 95%, at least 98% or at least 99% sequence identity.

The present invention also provides an antibody or antigen-binding fragment of an antibody comprising a light chain variable region (LCVR) having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, 394, 410, and 426, or a substantially similar sequence thereof having at least 90%, at least 95%, at least 98% or at least 99% sequence identity.

The present invention also provides an antibody or antigen-binding fragment thereof comprising a HCVR and LCVR (HCVR/LCVR) sequence pair selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, and 418/426.

The present invention also provides an antibody or antigen-binding fragment of an antibody comprising a heavy chain CDR3 (HCDR3) domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, 376, 392, 408, and 424, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, 384, 400, 416, and 432, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 24/32, 40/48, 56/64, 72/80, 88/96, 104/112, 120/128, 136/144, 152/160, 168/176, 184/192, 200/208, 216/224, 232/240, 248/256, 264/272, 280/288, 296/304, 312/320, 328/336, 344/352, 360/368, 376/384, 392/400, 408/416, and 424/432.

The present invention also provides an antibody or fragment thereof further comprising a heavy chain CDR1 (HCDR1) domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, 372, 388, 404, and 420, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, 374, 390, 406, and 422, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, 380, 396, 412, and 428, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, 398, 414, and 430, or a substantially similar sequence thereof having at least 90%, at least 95%, at least 98% or at least 99% sequence identity.

Certain non-limiting, exemplary antibodies and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H2M6486N); 20-22-24-28-30-32 (e.g. H2M6490N); 36-38-40-44-46-48 (e.g. H1M6492N); 52-54-56-60-62-64 (e.g. H1M6494N); 68-70-72-76-78-80 (e.g. H2M6495N); 84-86-88-92-94-96 (e.g. H2M6741N); 100-102-104-108-110-112 (e.g. H4H6311P); 116-118-120-124-126-128 (e.g. H4H6316P); 132-134-136-140-142-144 (e.g. H4H6317P); 148-150-152-156-158-160 (e.g. H4H6323P); 164-166-168-172-174-176 (e.g. H4H6327P2); 180-182-184-188-190-192 (e.g. H4H6328P); 196-198-200-204-206-208 (e.g. H4H6329P); 212-214-216-220-222-224 (e.g. H4H6330P); 228-230-232-236-238-240 (e.g. H4H6332P); 244-246-248-252-254-256 (e.g. H4H6334P); 260-262-264-268-270-272 (e.g. H4H6334P2); 276-278-280-284-286-288 (e.g. H4H6335P); 292-294-296-300-302-304 (e.g. H4H6337P); 308-310-312-316-318-320 (e.g. H4H6338P); 324-326-328-332-334-336 (e.g. H4H6340P); 340-342-344-348-350-352 (e.g. H4H6343P); 356-358-360-364-366-368 (e.g. H4H6345P); 372-374-376-380-382-384 (e.g. H4H6347P); 388-390-392-396-398-400 (e.g. H4H6353P); 404-406-408-412-414-416 (e.g. H4H6490N2); and 420-422-424-428-430-432 (e.g. H4H6492N2).

In a related embodiment, the invention includes an antibody or antigen-binding fragment of an antibody which specifically binds human big-ET-1, wherein the antibody or fragment comprises the heavy and light chain CDR domains contained within heavy and light chain sequences selected from the group consisting of SEQ ID NO: 2/10, 18/26, 34/42, 50/58, 66/74, 82/90, 98/106, 114/122, 130/138, 146/ 154, 162/170, 178/186, 194/202, 210/218, 226/234, 242/250, 258/266, 274/282, 290/298, 306/314, 322/330, 338/346, 354/362, 370/378, 386/394, 402/410, and 418/426. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., (1997) *J. Mol. Biol.* 273:927-948; and Martin et al. (1989) *Proc. Natl. Acad. Sci. USA* 86:9268-9272. Public databases are also available for identifying CDR sequences within an antibody.

In another aspect, the invention provides nucleic acid molecules encoding anti-human big-ET-1 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273, 289, 305, 321, 337, 353, 369, 385, 401, and 417, or a substantially identical sequence having at least 90%, at least 95%, at least 98%, or at least 99% homology thereof.

The present invention also provides an antibody or fragment thereof comprising a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281, 297, 313, 329, 345, 361, 377, 393, 409, and 425, or a substantially identical sequence having at least 90%, at least 95%, at least 98%, or at least 99% homology thereof.

The present invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 295, 311, 327, 343, 359, 375, 391, 407, and 423, or a substantially identical sequence having at least 90%, at least 95%, at least 98%, or at least 99% homology thereof; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287, 303, 319, 335, 351, 367, 383, 399, 415, and 431, or a substantially identical sequence having at least 90%, at least 95%, at least 98%, or at least 99% homology thereof.

The present invention also provides an antibody or fragment thereof which further comprises a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 291, 307, 323, 339, 355, 371, 387, 403, and 419, or a substantially identical sequence having at least 90%, at least 95%, at least 98%, or at least 99% homology thereof; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 293, 309, 325, 341, 357, 373, 389, 405, and 421, or a substantially identical sequence having at least 90%, at least 95%, at least 98%, or at least 99% homology thereof; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283, 299, 315, 331, 347, 363, 379, 395, 411, and 427, or a substantially identical sequence having at least 90%, at least 95%, at least 98%, or at least 99% homology thereof; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285, 301, 317, 333, 349, 365, 381, 397, 413, and 429, or a substantially identical sequence having at least 90%, at least 95%, at least 98%, or at least 99% homology thereof.

According to certain embodiments, the antibody or fragment thereof comprises the heavy and light chain CDR sequences encoded by the nucleic acid sequences of SEQ ID NOs: SEQ ID NOs: 1 and 9 (e.g. H2M6486N), 17 and 25 (e.g. H2M6490N), 33 and 41 (e.g. H1M6492N), 49 and 57 (e.g. H1M6494N), 65 and 73 (e.g. H2M6495N), 81 and 89 (e.g. H2M6741N), 97 and 105 (e.g. H4H6311P), 113 and 121 (e.g. H4H6316P), 129 and 137 (e.g. H4H6317P), 145 and 153 (e.g. H4H6323P), 161 and 169 (e.g. H4H6327P2), 177 and 185 (e.g. H4H6328P), 193 and 201 (e.g. H4H6329P), 209 and 217 (e.g. H4H6330P), 225 and 233 (e.g. H4H6332P), 241 and 249 (e.g. H4H6334P), 257 and 265 (e.g. H4H6334P2), 273 and 281 (e.g. H4H6335P), 289 and 297 (e.g. H4H6337P), 305 and 313 (e.g. H4H6338P), 321 and 329 (e.g. H4H6340P), 337 and 345 (e.g. H4H6343P), 353 and 361 (e.g. H4H6345P), 369 and 377 (e.g. H4H6347P), 385 and 393 (e.g. H4H6353P), 401 and 409 (e.g. H4H6490N2), and 417 and 425 (e.g. H4H6492N2).

The present invention includes anti-big-ET-1 antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) *JBC* 277:26733-26740). In other applications, modification of galactosylation can be made in order to modify complement dependent cytotoxicity (CDC).

In another aspect, the invention provides a pharmaceutical composition comprising a recombinant human antibody or fragment thereof which specifically binds big-ET-1 and a pharmaceutically acceptable carrier. In a related aspect, the invention features a composition which is a combination of an endothelin-1 inhibitor and a second therapeutic agent. In one embodiment, the endothelin-1 inhibitor is an antibody or fragment thereof. In one embodiment, the second therapeutic agent is any agent that is advantageously combined with an endothelin-1 inhibitor. Exemplary agents that may be advantageously combined with an endothelin-1 inhibitor include, without limitation, other agents (including other antibodies or antigen-binding fragments thereof, peptide inhibitors, small molecule antagonists, etc.) that inhibit the interaction between endothelin-1 and an endothelin-1 receptor, and/or agents which interfere with endothelin-1 upstream or downstream signaling.

In yet another aspect, the invention provides methods for inhibiting endothelin-1 activity using an anti-big-ET-1 antibody or antigen-binding portion of an antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of endothelin-1 activity. The anti-big-ET-1 antibody or antibody fragment of the invention may function to block the interaction between endothelin-1 and an endothelin-1 receptor (e.g., ETaR and/or ETbR), or otherwise inhibit the signaling activity of endothelin-1. In some embodiments of the invention, the disease or condition to be treated, prevented or ameliorated through methods of the invention include pulmonary hypertension (including pulmonary arterial hypertension, pulmonary hypertension associated with left heart disease, pulmonary hypertension associated with lung diseases, or pulmonary hypertension due to chronic thrombotic disease and pulmonary hypertension due to embolic disease), renal disease, allograft rejection, diabetes, cancer (including prostate cancer, breast cancer, ovarian cancer, and melanoma), heart failure, atherosclerosis, fibrotic disease, eye disease, and pain (including nociceptive pain and visceral pain). In some embodiments of the invention, the pain to be treated, prevented or ameliorated through methods of the invention includes pain associated with inflammation, post-operative incision, neuropathy, bone fracture, burn, osteoporotic fracture, bone cancer, gout, migraine headache, fibromyalgia, cancer-associated pain or chemotherapy-induced pain. In some embodiments of the invention, the eye disease or condition to be treated, prevented or ameliorated through methods of the invention include age-related macular degeneration (AMD), exudative AMD, diabetic retinopathy, central retinal vein occlusion (CRVO), iris neovascularization, glaucoma (e.g., neovascular glaucoma), post-surgical fibrosis in glaucoma, proliferative vitreoretinopathy (PVR), choroidal neovascularization, optic disc neovascularization, corneal neovascularization, retinal neovascularization, vitreal neovascularization, pannus, pterygium, macular edema, diabetic macular edema (DME), vascular retinopathy, retinal degeneration, uveitis, and inflammatory diseases of the eye. In some embodiments of the invention, the fibrotic disease or condition to be treated, prevented or ameliorated through methods of the invention include pulmonary fibrosis, ocular fibrosis, skin fibrosis, kidney fibrosis, or liver fibrosis.

The present invention also includes the use of an anti-big-ET-1 antibody or antigen binding portion of an antibody of the invention in the manufacture of a medicament for the treatment of a disease or disorder related to or caused by endothelin-1 activity in a patient.

Other embodiments will become apparent from a review of the ensuing detailed description.

DETAILED DESCRIPTION

Figure 1:
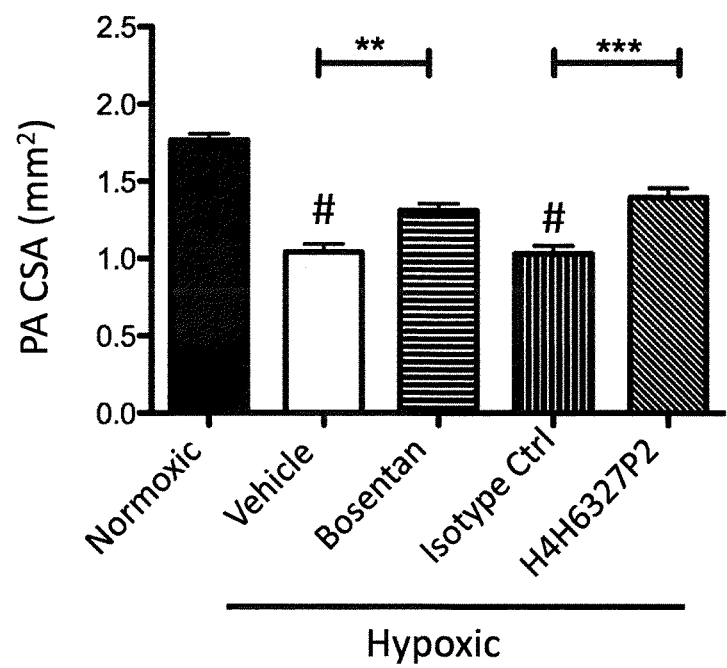
FIG. 1. Pulmonary Artery Cross-Sectional Area (PA CSA). H4H6327P2 and Bosentan treatment significantly lessen the reduction in PA CSA induced by chronic hypoxia. Preservation of PA CSA from baseline (i.e., Normoxic) reflects less muscular wall thickening (i.e., vessel remodeling) and/or less vascular tone (i.e., vasoconstriction). # designates P<0.001 vs. Normoxic. , * denote P<0.01, and 0.001, respectively.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expressions "pre-pro-endothelin-1", "pre-pro-ET-1", "pre-pro-EDN-1", and the like, as used herein, mean a polypeptide having the amino acid sequence as set forth in SEQ ID NO:433.

The expressions "big-endothelin-1", "big-EDN-1", "big-ET-1", and the like, as used herein, mean a polypeptide having the amino acid sequence of SEQ ID NO:434, which is identical to amino acids 53 through 90 of SEQ ID NO:433.

The expressions "endothelin-1", "ET-1", "EDN-1", "small-endothelin-1", "small-ET-1", "small-EDN-1", and the like, as used herein, mean a polypeptide having the amino acid sequence of SEQ ID NO:435, which is identical to amino acids 53 through 73 of SEQ ID NO:433. (The amino acid sequence of small-ET-1 is same for mouse and human versions of the peptide.)

All of the foregoing expressions (e.g., "pre-pro-ET-1", "big-ET-1", "small-ET-1", "endothelin-1", etc.), as used herein, refer to the human versions of the corresponding molecules unless specified as being from a non-human species (e.g., "mouse pre-pro-ET-1", "mouse big-ET-1", "mouse small-ET-1", "mouse endothelin-1", etc.).

The expressions "endothelin-converting enzyme-1", "ECE-1", and the like, as used herein, mean an enzyme capable of specifically cleaving big-ET-1 at the junction of Trp-21 and Val-22 of SEQ ID NO:434 (i.e., "the Tpr21/Val22 junction") to thereby generate small-ET-1 and a non-active C-terminal product having amino acids 22 through 38 of SEQ ID NO:434. An exemplary ECE-1 is the human enzyme having the amino acid sequence of SEQ ID NO:436.

The term "antibody," as used herein, means any antigen-binding molecule or molecular complex comprising at least one complementarity determining region (CDR) that specifically binds to or interacts with a particular antigen (e.g., big-ET-1). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; $V_H$-$C_L$; $V_L$-$C_H1$; (ix) $V_L$-$C_H2$; (x) $V_L$- $C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) *Proc. Natl. Acad. Sci. USA* 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) *Mol Immunol* 30:105-108) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" human big-ET-1, as used in the context of the present invention, includes antibodies that bind human big-ET-1 or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. (See, e.g., Example 3, herein). An isolated antibody that specifically binds human big-ET-1 may, however, have cross-reactivity to other antigens, such as endothelin molecules from other (non-human) species.

A "neutralizing" or "blocking" antibody, as used herein, is intended to refer to an antibody whose binding to big-ET-1: (i) inhibits or interferes with the cleavage of big-ET-1 by an endothelin converting enzyme (e.g., ECE-1), and/or (ii) results in inhibition of at least one biological function of endothelin-1. The inhibition caused by a big-ET-1 neutralizing or blocking antibody need not be complete so long as it is detectable using an appropriate assay. Exemplary assays for detecting big-ET-1 cleavage inhibition are described elsewhere herein.

The anti-big-ET-1 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-big-ET-1 antibodies comprising variants of any of the HCVR, LCVR, and/or CDR amino acid sequences disclosed herein having one or more conservative substitutions. For example, the present invention includes anti-big-ET-1 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) *Methods Mol Biol* 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Besffit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) *Methods Mol Biol* 132: 185-219). Another preferred algorithm when comparing a sequence of the invention to a database containing a large number of sequences from different organisms is the computer program BLAST, especially BLASTP or TBLASTN, using default parameters. See, e.g., Altschul et al. (1990) *J Mol Biol* 215:403-410 and Altschul et al. (1997) *Nucleic Acids Res* 25:3389-402, each herein incorporated by reference.

Biological Characteristics of the Antibodies

The antibodies of the present invention specifically bind human big-ET-1 (SEQ ID NO:434) but do not bind human small-ET-1 (SEQ ID NO:435). Any assay format that quantitatively or qualitatively measures the interaction between an antibody and an antigen can be used to determine whether an antibody specifically binds, or does not bind, human big-ET-1 and/or human small-ET-1. For example, a surface plasmon resonance assay, as illustrated in Example 3 herein, can be used to determine if a particular test antibody specifically binds, or does not bind, human big-ET-1 and/or human small-ET-1. For purposes of the present disclosure, an antibody that, when tested for binding to small-ET-1 in a surface plasmon resonance assay exhibits a $K_D$ value greater than about 1.0E-06 M (i.e., >1000 nM), or does not show any detectable binding to small-ET-1, is considered an antibody that "does not bind human small-ET-1." Certain exemplary antibodies of the present invention that do not bind human small-ET-1, as that expression is defined herein, nonetheless demonstrate specific binding to human big-ET-1 with a $K_D$ value less than about 1.0E-07 M (e.g., 1.0E-08 M, 1.0E-09 M, 1.0E-10 M, 1.0E-11 M, 1.0E-12 M, or less) when tested for binding to human big-ET-1 in a surface plasmon resonance assay, as illustrated in Example 3 herein, or similar assay.

Another characteristic of certain exemplary antibodies of the present invention is the ability to block the cleavage of big-ET-1 (SEQ ID NO:434) by endothelin-converting enzyme-1 (ECE-1). The cleavage of big-ET-1 by ECE-1 produces two fragments: small-ET-1 (corresponding to the N-terminal 21 amino acids of SEQ ID NO:434), and a non-active C-terminal product (corresponding to the C-terminal 17 amino acids of SEQ ID NO:434). Thus, when big-ET-1 is mixed with ECE-1, the appearance of biologically-active small-ET-1, and/or the appearance of the non-active C-terminal peptide, serves as an indicator of the degree to which big-ET-1 was cleaved by ECE-1.

Any assay format which detects cleavage of big-ET-1 by ECE-1 can be used to determine if an antibody "blocks cleavage," as that expression is used herein. A non-limiting, exemplary assay format that can be used to determine if an antibody blocks the cleavage of big-ET-1 by ECE-1 is shown in Example 4, herein. In this example, cleavage of big-ET-1 is indirectly detected using an engineered cell line that produces a reporter signal only in response to the presence of endothelin-1 (i.e., small-ET-1, the cleavage product of big-ET-1). In particular, this assay format uses a cell line that expresses the human endothelin receptor type A (ETaR) along with a luciferase reporter element. A cleavage reaction is first set up wherein antibodies are added to big-ET-1, followed by the addition of ECE-1, and then the reaction is allowed to incubate for an appropriate amount of time under conditions conducive to the enzymatic cleavage of big-ET-1 (e.g., overnight at 37° C.). The cleavage reactions are then added to the ETaR-expressing reporter cell line, and the amount of reporter activity (if any) is measured. Blocking antibodies will inhibit the cleavage of big-ET-1 and thus will inhibit the formation of small-ET-1. Reactions that include blocking antibodies will consequently produce reduced or no reporter activity when added to the reporter cell line. By varying the amount of antibody used in this assay format, the amount of antibody that is necessary to inhibit 50% of big-ET-1 cleavage can be calculated and expressed in terms of an $IC_{50}$ value (see, e.g., Example 4, Tables 4-5). According to the present invention, an anti-big-ET-1 antibody "blocks cleavage of big-ET-1 by ECE-1" if the antibody, when tested in the assay format described above, or a substantially similar assay, exhibits an $IC_{50}$ of less than about 1.0E-08 M (e.g., an $IC_{50}$ of about 9.0E-09 M, about 8.5E-09 M, about 8.0E-09 M, about 7.5E-09 M, about 7.0E-09 M, about 6.5E-09 M, about 6.0E-09 M, about 5.5E-09 M, about 5.0E-09 M, about 4.5E-09 M, about 4.0E-09 M, about 3.5E-09 M, 3.0E-09 M, about 2.5E-09 M, about 2.0E-09 M, about 1.5E-09 M, about 1.0E-09 M, about 9.0E-10 M, about 8.5E-10 M, about 8.0E-10 M, about 7.5E-10 M, about 7.0E-10 M, about 6.5E-10 M, about 6.0E-10 M, about 5.5E-10 M, about 5.0E-10 M, about 4.5E-10 M, about 4.0E-10 M, about 3.5E-10 M, 3.0E-10 M, about 2.5E-10 M, about 2.0E-10 M, about 1.5E-10 M, about 1.0E-10 M, or less).

An additional, or alternative, exemplary assay format that can be used to determine if an antibody blocks the cleavage of big-ET-1 by ECE-1 is shown in Example 5, herein. In this assay format, a cleavage reaction is set up wherein antibodies are added to big-ET-1, followed by the addition of ECE-1. The reaction is allowed to incubate under conditions conducive to the enzymatic cleavage of big-ET-1 (e.g., at 37° C.), and aliquots are taken at various time points (e.g., 0, 15, 30 and 60 minutes) after initiation of the reaction. The aliquots are subjected to matrix assisted laser desorption ionization-time of flight (MALDI-TOF) mass spectrometry analysis to determine the presence or absence of cleavage products. The cleavage of big-ET-1 by ECE-1 produces peptide products having characteristic molecular weights. For example, the cleavage of human big-ET-1 by ECE-1 produces small-ET-1 having a molecular weight of 2475 Da, and a non-active C-terminal peptide having a molecular weight of 1809 Da. The appearance of either or both of these fragments by MALDI-TOF indicates the cleavage of big-ET-1 by ECE-1 in this assay. If, however, after combining big-ET-1 with an anti-big-ET-1 antibody, the addition of ECE-1 does not produce one or both of the cleavage products (or produces substantially less of the cleavage products as compared to a negative control antibody), then it is concluded that the antibody "blocks cleavage of big-ET-1 by ECE-1," as that expression is used herein.

The present invention also includes antibodies that inhibit or reduce endothelin-1-mediated increases in arterial blood pressure. An exemplary animal model that can be used to assess endothelin-mediated increases in arterial blood pressure is illustrated in Example 6, herein. In this Example, mice are administered an anti-big-ET-1 antibody followed by administration of human big-ET-1 peptide. Changes in arterial pressure are measured in real time following big-ET-1 challenge. Cleavage of big-ET-1 in vivo into bioactive small-ET-1 is reflected in increases in mean arterial blood pressure. When a blocking anti-big-ET-1 antibody is administered in this assay format, mean arterial blood pressure does not increase, or increases to a lesser extent, as compared to administration of an isotype control antibody.

The present invention also includes antibodies that inhibit or reduce pain response(s) in various animal pain models. Exemplary animal pain models useful for characterizing the anti-big-ET-1 antibodies of the present invention are illustrated in Example 9, herein (e.g., nocifensive behavior reduction). The present invention also includes anti-big-ET-1 antibodies that attenuate or inhibit visceral pain responses (e.g., responses to acid-induced visceral pain in a mouse model). In particular, the present invention includes anti-big-ET-1 antibodies that exhibit at least a 20% inhibition of visceral pain responses (e.g., abdominal constrictions in response to an intraperitoneal injection of 0.6% acetic acid) when administered at a dose of about 1 or 10 mg/kg in an animal model. In certain instances, the percent inhibition in pain responses due to the administration of an antibody of the present invention can be as high as about 30%, 35%, 40%, 45%, 50%, or higher when tested in an animal pain model. Additional animal pain models that can be used to characterize the anti-big-ET-1 antibodies of the present invention include, e.g., mechanical nociception pain response models, muscle pain models, and other similar animal models available in the art. Thus, the present invention includes anti-big-ET-1 antibodies capable of attenuating or inhibiting pain responses to noxious mechanical stimuli and/or acidic-saline- or carrageenan-induced muscle hyperalgesia.

Epitope Mapping and Related Technologies

The present invention includes antibodies which interact with one or more amino acids located at or near the ECE-1 cleavage site of big-ET-1. ECE-1 cleaves big-ET-1 at the junction of Trp-21 and Val-22 of big-ET-1 (SEQ ID NO:434). Thus, the present invention includes anti-big-ET-1 antibodies that interact with one or more amino acids located within 10 amino acids of the Trp-21/Val-22 junction of big-ET-1 (SEQ ID NO:434). The epitope to which the antibodies bind may consist of a single contiguous sequence of 3 or more (e.g., 3, 4, 5, 6, 7, 8, 9, or 10) amino acids located at or near the ECE-1 cleavage site of big-ET-1. Alternatively, the epitope may consist of a plurality of non-contiguous amino acids (or amino acid sequences) located at or near (e.g., within about 10 amino acids of) the ECE-1 cleavage site of big-ET-1.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide blots analysis (Reineke (2004) *Methods Mol Biol* 248:443-463), and peptide cleavage analysis. In addition, methods such as epitope excision, epitope extraction and chemical modification of antigens can be employed (Tomer (2000) *Protein Science* 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention further includes anti-big-ET-1 antibodies that bind to the same epitope as any of the specific exemplary antibodies described herein (e.g. H2M6486N, H2M6490N, H1M6492N, H1M6494N, H2M6495N, H2M6741N, H4H6311P, H4H6316P, H4H6317P, H4H6323P, H4H6327P2, H4H6328P, H4H6329P, H4H6330P, H4H6332P, H4H6334P, H4H6334P2, H4H6335P, H4H6337P, H4H6338P, H4H6340P, H4H6343P, H4H6345P, H4H6347P, H4H6353P, H4H6490N2, H4H6492N2, etc.). Likewise, the present invention also includes anti-big-ET-1 antibodies that compete for binding to big-ET-1 with any of the specific exemplary antibodies described herein (e.g. H2M6486N, H2M6490N, H1M6492N, H1M6494N, H2M6495N, H2M6741N, H4H6311P, H4H6316P, H4H6317P, H4H6323P, H4H6327P2, H4H6328P, H4H6329P, H4H6330P, H4H6332P, H4H6334P, H4H6334P2, H4H6335P, H4H6337P, H4H6338P, H4H6340P, H4H6343P, H4H6345P, H4H6347P, H4H6353P, H4H6490N2, H4H6492N2, etc.).

One can easily determine whether an antibody binds to the same epitope as, or competes for binding with, a reference anti-big-ET-1 antibody by using routine methods known in the art. For example, to determine if a test antibody binds to the same epitope as a reference anti-big-ET-1 antibody of the invention, the reference antibody is allowed to bind to a big-ET-1 protein or peptide under saturating conditions. Next, the ability of a test antibody to bind to the big-ET-1 molecule is assessed. If the test antibody is able to bind to big-ET-1 following saturation binding with the reference anti-big-ET-1 antibody, it can be concluded that the test antibody binds to a different epitope than the reference anti-big-ET-1 antibody. On the other hand, if the test antibody is not able to bind to the big-ET-1 molecule following saturation binding with the reference anti-big-ET-1 antibody, then the test antibody may bind to the same epitope as the epitope bound by the reference anti-big-ET-1 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al. (1990) *Cancer Res* 50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-big-ET-1 antibody, the above-described binding methodology is performed in two orientations: In a first orientation, the reference antibody is allowed to bind to a big-ET-1 molecule under saturating conditions followed by assessment of binding of the test antibody to the big-ET-1 molecule. In a second orientation, the test antibody is allowed to bind to a big-ET-1 molecule under saturating conditions followed by assessment of binding of the reference antibody to the big-ET-1 molecule. If, in both orientations, only the first (saturating) antibody is capable of binding to the big-ET-1 molecule, then it is concluded that the test antibody and the reference antibody compete for binding to big-ET-1. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

Methods for generating monoclonal antibodies, including fully human monoclonal antibodies are known in the art. Any such known methods can be used in the context of the present invention to make human antibodies that specifically bind to human big-ET-1.

Using VELOCIMMUNE™ technology or any other known method for generating monoclonal antibodies, high affinity chimeric antibodies to big-ET-1 are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-big-ET-1 antibodies and antibody fragments of the present invention encompass proteins having amino acid sequences that vary from those of the described antibodies but that retain the ability to bind human big-ET-1. Such variant antibodies and antibody fragments comprise one or more additions, deletions, or substitutions of amino acids when compared to parent sequence, but exhibit biological activity that is essentially equivalent to that of the described antibodies. Likewise, the anti-big-ET-1 antibody-encoding DNA sequences of the present invention encompass sequences that comprise one or more additions, deletions, or substitutions of nucleotides when compared to the disclosed sequence, but that encode an anti-big-ET-1 antibody or antibody fragment that is essentially bioequivalent to an anti-big-ET-1 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-big-ET-1 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-big-ET-1 antibody variants comprising amino acid changes which modify the glycosylation characteristics of the antibodies, e.g., mutations which eliminate or remove glycosylation.

Species Selectivity and Species Cross-Reactivity

According to certain embodiments of the invention, the anti-big-ET-1 antibodies bind to human big-ET-1 but not to big-ET-1 from other species. The present invention also includes anti-big-ET-1 antibodies that bind to human big-ET-1 and to big-ET-1 from one or more non-human species. For example, the anti-big-ET-1 antibodies of the invention may bind to human big-ET-1 and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee big-ET-1.

Immunoconjugates

The invention encompasses anti-big-ET-1 monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see, for example, WO 05/103081).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al. (1991) *J Immunol* 147:60-69; Kufer et al. (2004) *Trends Biotechnol* 22:238-244. The anti-big-ET-1 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human big-ET-1 or a fragment thereof, and the other arm of the immunoglobulin is specific for a second therapeutic target or is conjugated to a therapeutic moiety.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Formulation and Administration

The invention provides pharmaceutical compositions comprising the anti-big-ET-1 antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with endothelin-1 activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-big-ET-1 antibodies may be determined empirically; for example, patient progress can be monitored by periodic assessment, and the dose adjusted accordingly. Moreover, interspecies scaling of dosages can be performed using well-known methods in the art (e.g., Mordenti et al. (1991) *Pharmaceut Res* 8:1351-1359).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) *J Biol Chem* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton (1987) Crit Ref Biomed Eng 14:201-240). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer (1990) Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with or mediated by endothelin-1 activity or treatable by blocking the cleavage of big-ET-1 into small-ET-1. The antibodies and antigen-binding fragments of the present invention may be used to treat, e.g., fibrotic diseases [e.g., fibrosis (e.g., pulmonary fibrosis]), inflammatory conditions, hypertrophy (e.g., hypertrophy in cardiac myocytes and/or the vasculature), vascular diseases (e.g., diseases and disorders characterized by vasoconstriction), eye diseases, cancer (e.g., tumor growth inhibition) and pain. Specific, exemplary diseases and disorders that can be treated using an anti-big-ET-1 antibody of the present invention include, e.g., pulmonary hypertension, arterial hypertension, renal disease, allograft rejection, diabetes, insulin resistance, heart failure, atherosclerosis, stroke, arrhythmia, asthma, sickle cell anemia, cerebral vasospasm, diabetic nephropathy, scleroderma, COPD, nociceptive pain and visceral pain (e.g., pain from inflammatory bowel disease/irritable bowel syndrome, interstitial cystitis, pancreatitis, endometriosis, chronic pelvic pain syndrome, etc.). Additional pain-related diseases and disorders that may be treated, prevented or ameliorated with the antibodies and antigen-binding fragments of the present invention include pain associated with inflammation (e.g., inflammatory muscle pain), polymyositis, post-operative incision (e.g., post-surgical pain), neuropathy (e.g., diabetic neuropathy), sciatica, post-herpetic neuralgia, myofascial pain syndromes (e.g., chronic myofascial pain), arthritis, sickle cell, enteric nerve ischemia, claudication pain, bone fracture, burn, osteoporotic fracture, gout, migraine headache, fibromyalgia, complex regional pain syndrome, and acute herpetic pain.

Subcategories of pulmonary hypertension that can be treated using an anti-big-ET-1 antibody of the present invention include, e.g. pulmonary arterial hypertension, pulmonary hypertension associated with left heart disease, pulmonary hypertension associated with lung diseases, pulmonary hypertension due to chronic thrombotic disease or pulmonary hypertension due to embolic disease.

Exemplary eye diseases that are treatable by administering the anti-big-ET-1 antibodies of the invention include age-related macular degeneration (e.g., "wet" AMD), exudative AMD, diabetic retinopathy (e.g., proliferative diabetic retinopathy), retinal venous occlusive diseases such as central retinal vein occlusion (CRVO), iris neovascularization, neovascular glaucoma, post-surgical fibrosis in glaucoma, proliferative vitreoretinopathy (PVR), choroidal neovascularization, optic disc neovascularization, corneal neovascularization, retinal neovascularization, vitreal neovascularization, pannus, pterygium, macular edema, diabetic macular edema (DME), vascular retinopathy, retinal degeneration, uveitis, and inflammatory diseases of the eye. For example, the administration of anti-big-ET-1 antibodies of the invention can prevent and/or treat neurodegenerative effects and optic nerve injury associated with glaucoma by blocking vasoconstriction caused by ET-1 as well as ET-1 effects on astrocytes (e.g., axonal loss) and retinal ganglion cells (e.g., apoptosis).

Additional exemplary fibrotic diseases that are treatable by administering the anti-big-ET-1 antibodies of the invention include idiopathic pulmonary fibrosis, bleomycin-induced pulmonary fibrosis, asbestos-induced pulmonary fibrosis, bronchiolitis obliterans syndrome, chronic asthma, fibrosis associated with acute lung injury and acute respiratory distress (e.g., bacterial pneumonia induced fibrosis, trauma induced fibrosis, viral pneumonia induced fibrosis, ventilator induced fibrosis, non-pulmonary sepsis induced fibrosis and aspiration induced fibrosis), silicosis, radiation-induced fibrosis, chronic obstructive pulmonary disease (COPD), ocular fibrosis, skin fibrosis (e.g., scleroderma), hepatic fibrosis (e.g., cirrhosis, alcohol-induced liver fibrosis, non-alcoholic steatohepatitis (NASH), biliary duct injury, primary biliary cirrhosis, infection- or viral-induced liver fibrosis [e.g., chronic HCV infection], autoimmune hepatitis), kidney (renal) fibrosis, cardiac fibrosis, atherosclerosis, stent restenosis, and myelofibrosis.

The anti-big-ET-1 antibodies and antigen-binding fragments thereof of the present invention are also useful for treating cancer (e.g., prostate cancer, breast cancer, ovarian cancer, melanoma, renal cancer, colorectal cancer, cervical cancer, endometrial cancer, bladder cancer, Kaposi's sarcoma, and glioma), inhibiting tumor growth, promoting tumor regression, inhibiting metastasis, and/or inhibiting pathological angiogenesis (e.g., angiogenesis related to tumor growth). Accordingly, the present invention includes methods of treating cancer, inhibiting tumor growth, promoting tumor regression, inhibiting metastasis, and/or inhibiting pathological angiogenesis (e.g., angiogenesis related to tumor growth) by administering an anti-big-ET-1 antibody as described herein to a patient in need of such treatment. For example, the antibodies and antigen-binding fragments of the present invention may be used to treat, e.g., primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the antibodies and antigen-binding fragments of the invention are used to treat one or more of the following cancers: renal cell carcinoma, pancreatic carcinoma, breast cancer, head and neck cancer (e.g., cancer of the brain, oral cavity, orophyarynx, nasopharynx, hypopharynx, nasal cavity, paranasal sinuses, larynx, lip, etc.), prostate cancer, urinary bladder cancer, malignant gliomas, osteosarcoma, osteoblastoma, osteochondroma, colorectal cancer, gastric cancer (e.g., gastric cancer with MET amplification), malignant mesothelioma, astrocytoma, glioblastoma, medulloblastoma, retinoblastoma, multiple myeloma, ovarian cancer, small cell lung cancer, non-small cell lung cancer, synovial sarcoma, thyroid cancer, connective tissue neoplasms, Kaposi's sarcoma, basal cell carcinoma, squamous cell carcinoma, or melanoma.

Combination Therapies

The present invention includes therapeutic administration regimens which comprise administering an anti-big-ET-1 antibody of the present invention in combination with at least one additional therapeutically active component. Non-limiting examples of such additional therapeutically active components include other endothelin-1 antagonists (e.g., an anti-endothelin-1 antibody, a different anti-big-ET-1 antibody, or small molecule inhibitor of endothelin-1), endothelin-A receptor antagonist, endothelin-B receptor antagonist, non-selective endothelin receptor antagonist, prostacyclin, prostacyclin analog, non-prostanoid inositol phosphate (prostacyclin) receptor agonist, Phosphodiesterase type 5 inhibitors, soluble guanylate cyclase stimulators, endothelin-converting enzyme-1 (ECE-1) inhibitor, Neprilysin inhibitor, angiotensin-II receptor agonist, and NF-kappa B inhibitor. Exemplary agents that can be administered in combination with an anti-big-ET-1 antibody of the invention include, e.g., endothelin receptor antagonists such as Bosentan (Roche), Ambrisentan (Abbott), Sitaxentan (Encysive), Clazosentan (Chugai), Darusentan (Abbott), ZD4054 (AstraZeneca), Macitentan (Actelion), Avosentan (Roche), Daglutril (Solvay), PS433540 (Bristol-Myers Squibb), S0139 (Shionogi), SLV334 (Solvay), TBC3711 (Encysive), Fandosentan (Pfizer), PABSA (Shionogi), YM598 (Astellas) and YM62899 (Astellas); phosphodiesterase type 5 inhibitors such as Sildenafil (Pfizer) and Tadalafil (Lilly ICOS); soluble guanylate cylase stimulators such as Riociguat (Bayer); and prostacyclin, prostanoids and prostacyclin receptor agonists such as iloprost (Actelion), treprostinil (United Therapeutics), beraprost (United Therapeutics), epoprostenol (Actelion), and selexipag (Actelion).

The anti-big-ET-1 antibodies of the present invention may be co-formulated with and/or administered in combination with, e.g., a VEGF antagonist, e.g., a "VEGF-trap" such as aflibercept or other VEGF-inhibiting fusion protein as set forth in U.S. Pat. No. 7,087,411, an anti-VEGF antibody or antigen binding fragment thereof (e.g., bevacizumab, ranibizumab), a small molecule kinase inhibitor of VEGF receptor (e.g., sunitinib, sorafenib or pazopanib), or an anti-VEGF receptor antibody. The anti-big-ET-1 antibody may also be combined with an anti-PDGFR-beta antibody (e.g., 2A1E2 [U.S. Pat. No. 7,060,271]; HuM4Ts.22 [U.S. Pat. No. 5,882,644]; or 1B3 or 2C5 [U.S. Pat. No. 7,740,850]), an anti PDGF ligand antagonist (e.g., an anti-PDGF-BB antibody, an anti-PDGF-DD antibody, an anti-PDGF-CC antibody, an anti-PDGF-AB antibody, or other PDGF ligand antagonist such as an aptamer, an antisense molecule, a ribozyme, an siRNA, a peptibody, a nanobody or an antibody fragment directed against a PDGF ligand). In other embodiments, the anti-big-ET-1 antibodies of the present invention may be co-formulated with and/or administered in combination with an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist specific for EGFRvIII (e.g., an antibody that specifically binds EGFRvIII), a cMET anagonist (e.g., an anti-cMET antibody), an IGF1R antagonist (e.g., an anti-IGF1R antibody), or a B-raf inhibitor (e.g., vemurafenib, sorafenib, GDC-0879, PLX-4720). In certain instances, the anti-big-ET-1 antibodies of the present invention are combined, co-formulated and/or administered in combination with a PDGFR-alpha inhibitor (e.g., an anti-PDGFR-alpha antibody), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), etc. The present invention also includes therapeutic combinations comprising any of the anti-big-ET-1 antibodies mentioned herein and an inhibitor of one or more of Ang2, Tie2, VEGF, DLL4, EGFR, or any of the aforementioned cytokines, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). Other agents that may be beneficially administered in combination with the anti-big-ET-1 antibodies of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The anti-big-ET-1 antibodies of the invention may also be administered and/or co-formulated in combination with anti-virals, antibiotics, analgesics, statins, diuretics, anti-coagulants, digoxin, corticosteroids, steroids, oxygen, antioxidants, metal chelators, IFN-gamma, and/or NSAIDs. The anti-big-ET-1 antibodies of the invention may also be administered as part of a treatment regimen that also includes radiation treatment and/or conventional chemotherapy (e.g., in the context of methods of treating cancer or inhibiting tumor growth).

Any of the aforementioned additional therapeutically active components may be administered in combination with any of the anti-big-ET-1 antibodies of the present invention for the treatment of any disease or disorder in which administration of an anti-big-ET-1 antibody is beneficial, including, e.g., any of the eye diseases, fibrotic diseases, vascular diseases and/or cancers mentioned herein. For example, in the context of treating an eye disease (e.g., wet AMD, diabetic retinopathy, CRVO, or any of the other eye diseases described herein), an anti-big-ET-1 antibody of the present invention may be co-formulated with, and/or administered in combination with a VEGF antagonist, e.g., a "VEGF-trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab).

The additional therapeutically active component(s) may be administered prior to, concurrent with, or after the administration of an anti-big-ET-1 antibody of the present invention; (for purposes of the present disclosure, such administration regimens are considered the administration of an anti-big-ET-1 antibody "in combination with" an additional therapeutically active component). In some embodiments of the invention, the additional therapeutically active component(s) may be administered to a subject prior to administration of an anti-big-ET-1 antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-big-ET-1 antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-big-ET-1 antibody of the present invention. "Concurrent" administration, for purposes of the present invention, includes, e.g., administration of an anti-big-ET-1 antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-big-ET-1 antibody and the additional therapeutically active component may be administered intravitreally, subcutaneously, etc.); alternatively, each dosage form may be administered via a different route (e.g., the anti-big-ET-1 antibody may be administered intravitreally, and the additional therapeutically active component may be administered systemically). In any event, administering the components in a single dosage from, in separate dosage forms by the same route, or in separate dosage forms by different routes are all considered "concurrent administration," for purposes of the present disclosure. For purposes of the present disclosure, administration of an anti-big-ET-1 antibody "prior to", "concurrent with," or "after" (as those terms are defined herein above) administration of an additional therapeutically active component is considered administration of an anti-big-ET-1 antibody "in combination with" an additional therapeutically active component).

The present invention includes pharmaceutical compositions in which an anti-big-ET-1 antibody of the present invention is co-formulated with one or more of the additional therapeutically active component(s) as described elsewhere herein.

Diagnostic Uses of the Antibodies

The anti-big-ET-1 antibodies of the present invention may also be used to detect and/or measure big-ET-1 in a sample, e.g., for diagnostic purposes. For example, an anti-big-ET-1 antibody, or fragment thereof, may be used to diagnose a condition or disease characterized by aberrant expression (e.g., over-expression, under-expression, lack of expression, etc.) of big-ET-1 or endothelin-1. Exemplary diagnostic assays for big-ET-1 may comprise, e.g., contacting a sample, obtained from a patient, with an anti-big-ET-1 antibody of the invention, wherein the anti-big-ET-1 antibody is labeled with a detectable label or reporter molecule. Alternatively, an unlabeled anti-big-ET-1 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure big-ET-1 in a sample include enzyme-linked immunosorbent assay (ELISA), radioimmunoassay (RIA), and fluorescence-activated cell sorting (FACS).

Samples that can be used in big-ET-1 diagnostic assays according to the present invention include any tissue or fluid sample obtainable from a patient which contains detectable quantities of big-ET-1 protein, or fragments thereof, under normal or pathological conditions. Generally, levels of big-ET-1 in a particular sample obtained from a healthy patient (e.g., a patient not afflicted with a disease or condition associated with abnormal endothelin-1 levels or activity) will be measured to initially establish a baseline, or standard, level of big-ET-1. This baseline level of big-ET-1 can then be compared against the levels of big-ET-1 measured in samples obtained from individuals suspected of having a big-ET-1 related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention.

Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Human Antibodies to Human Big-Endothelin-1 (Big-ET-1)

An immunogen comprising human big-ET-1 polypeptide (SEQ ID NO:434) was administered directly, with an adjuvant to stimulate the immune response, to a VELOCIMMUNE® mouse comprising DNA encoding human Immunoglobulin heavy and kappa light chain variable regions. The antibody immune response was monitored by a big-ET-1-specific immunoassay. When a desired immune response was achieved splenocytes were harvested and fused with mouse myeloma cells to preserve their viability and form hybridoma cell lines. The hybridoma cell lines were screened and selected to identify cell lines that produce big-ET-1-specific antibodies. Using this technique several anti-big-ET-1 chimeric antibodies (i.e., antibodies possessing human variable domains and mouse constant domains) were obtained; exemplary antibodies generated in this manner were designated as follows: 6486N, 6490N, 6492N, 6494N, 6495N, 6741N, 6490N2, and 6492N2.

Anti-big-ET-1 antibodies were also isolated directly from antigen-positive B cells without fusion to myeloma cells, as described in US 2007/0280945A1. Using this method, several fully human anti-big-ET-1 antibodies (i.e., antibodies possessing human variable domains and human constant domains) were obtained; exemplary antibodies generated in this manner were designated as follows: 6311P, 6316P, 6317P, 6323P, 6327P2, 6328P, 6329P, 6330P, 6332P, 6334P, 6335P, 6337P, 6338P, 6340P, 6343P, 6345P, 6347P, and 6353P.

Certain structural and functional properties of the exemplary anti-big-ET-1 antibodies generated in accordance with the methods of this Example are described in detail in the Examples set forth below.

Example 2: Heavy and Light Chain Variable Region Amino Acid Sequences

Table 1 sets forth the heavy and light chain variable region amino acid sequence pairs of selected anti-big-ET-1 antibodies and their corresponding antibody identifiers.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| 6486N | 2 | 4 | 6 | 8 | 10 | 12 | 14 | 16 |
| 6490N | 18 | 20 | 22 | 24 | 26 | 28 | 30 | 32 |
| 6492N | 34 | 36 | 38 | 40 | 42 | 44 | 46 | 48 |
| 6494N | 50 | 52 | 54 | 56 | 58 | 60 | 62 | 64 |
| 6495N | 66 | 68 | 70 | 72 | 74 | 76 | 78 | 80 |
| 6741N | 82 | 84 | 86 | 88 | 90 | 92 | 94 | 96 |
| 6311P | 98 | 100 | 102 | 104 | 106 | 108 | 110 | 112 |
| 6316P | 114 | 116 | 118 | 120 | 122 | 124 | 126 | 128 |
| 6317P | 130 | 132 | 134 | 136 | 138 | 140 | 142 | 144 |
| 6323P | 146 | 148 | 150 | 152 | 154 | 156 | 158 | 160 |
| 6327P2 | 162 | 164 | 166 | 168 | 170 | 172 | 174 | 176 |
| 6328P | 178 | 180 | 182 | 184 | 186 | 188 | 190 | 192 |
| 6329P | 194 | 196 | 198 | 200 | 202 | 204 | 206 | 208 |
| 6330P | 210 | 212 | 214 | 216 | 218 | 220 | 222 | 224 |
| 6332P | 226 | 228 | 230 | 232 | 234 | 236 | 238 | 240 |
| 6334P | 242 | 244 | 246 | 248 | 250 | 252 | 254 | 256 |
| 6334P2 | 258 | 260 | 262 | 264 | 266 | 268 | 270 | 272 |
| 6335P | 274 | 276 | 278 | 280 | 282 | 284 | 286 | 288 |
| 6337P | 290 | 292 | 294 | 296 | 298 | 300 | 302 | 304 |
| 6338P | 306 | 308 | 310 | 312 | 314 | 316 | 318 | 320 |
| 6340P | 322 | 324 | 326 | 328 | 330 | 332 | 334 | 336 |
| 6343P | 338 | 340 | 342 | 344 | 346 | 348 | 350 | 352 |
| 6345P | 354 | 356 | 358 | 360 | 362 | 364 | 366 | 368 |
| 6347P | 370 | 372 | 374 | 376 | 378 | 380 | 382 | 384 |
| 6353P | 386 | 388 | 390 | 392 | 394 | 396 | 398 | 400 |
| 6490N2 | 402 | 404 | 406 | 408 | 410 | 412 | 414 | 416 |
| 6492N2 | 418 | 420 | 422 | 424 | 426 | 428 | 430 | 432 |

Antibodies are typically referred to herein according to the following nomenclature: Fc prefix (e.g. "H4H", "H1M", "H2M"), followed by a numerical identifier (e.g. "6311" as shown in Table 1), followed by a "P" or "N" suffix. Thus, according to this nomenclature, an antibody may be referred to herein as, e.g., "H4H6311P". The H4H, H1M, and H2M prefixes on the antibody designations used herein indicate the particular Fc region of the antibody. For example, an "H2M" antibody has a mouse IgG2 Fc, whereas an "H4H" antibody has a human IgG4 Fc. As will be appreciated by a person of ordinary skill in the art, an H1M or H2M antibody can be converted to an H4H antibody, and vice versa, but in any event, the variable domains (including the CDRs)—which are indicated by the numerical identifiers shown in Table 1—will remain the same.

Example 3: Surface Plasmon Resonance Derived Binding Affinities and Kinetic Constants of Human Monoclonal Anti-Big-ET-1 Antibodies Binding affinities and kinetic constants of human monoclonal anti-big-ET-1 antibodies were determined by surface plasmon resonance at 37° C. using a mAb capture format (Tables 2-3). Measurements were conducted on a T200

Biacore instrument (Biacore Life Sciences division of GE Healthcare, Piscataway, N.J.). The Biacore sensor surface was derivatized with a rabbit anti-mouse for hybridoma capture (prefix H1M or H2M) or a mouse anti-human Fc surface for human IgG formatted antibodies (prefix H4H). Different concentrations of small-ET-1 (SEQ ID NO:435), human big-ET-1 (SEQ ID NO:434) or mouse big-ET-1 (SEQ ID NO:437) were injected over the anti-big-ET-1 captured surfaces at a flow rate of 100 μl/min. Peptide binding was monitored for 3 min while dissociation of mAb-bound peptide was monitored for 4 min in HBST running buffer (0.01 M HEPES pH 7.4, 0.15 M NaCl, 3 mM EDTA, 0.005% v/v Surfactant P20). Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D$ (M)=$k_d/k_a$; and $t_{1/2}$ (min)=(ln 2/(60*$k_d$). Results are shown in Tables 2 and 3 (NB=non-binding under conditions tested).

TABLE 2

Biacore Binding Affinities of Hybridoma mAbs (H1M and H2M) at 37° C.
Binding at 37° C. - mAb Capture Format

| Antibody | Analyte | ka (Ms$^{-1}$) | kd (s$^{-1}$) | $K_D$ (Molar) | T½ (min) |
|---|---|---|---|---|---|
| H2M6486N | human big-ET-1 | 3.80E+05 | 8.98E−02 | 2.39E−07 | 0.1 |
|  | mouse big-ET-1 | 8.30E+05 | 1.35E−01 | 1.60E−07 | 0.1 |
| H2M6490N | human big-ET-1 | 2.09E+05 | 3.99E−03 | 1.91E−08 | 3 |
|  | mouse big-ET-1 | NB | NB | NB | NB |
| H1M6492N | human big-ET-1 | 2.48E+05 | 1.60E−03 | 6.46E−09 | 7 |
|  | mouse big-ET-1 | NB | NB | NB | NB |
| H1M6494N | human big-ET-1 | 2.39E+05 | 1.69E−03 | 7.07E−09 | 7 |
|  | mouse big-ET-1 | NB | NB | NB | NB |
| H2M6495N | human big-ET-1 | 1.17E+05 | 1.00E−06 | 8.53E−12 | 11550 |
|  | mouse big-ET-1 | NB | NB | NB | NB |
| H2M6741N | human big-ET-1 | 5.82E+05 | 1.37E−01 | 2.36E−07 | 0.1 |
|  | mouse big-ET-1 | 3.85E+05 | 8.91E−02 | 2.32E−07 | 0.1 |

TABLE 3

Biacore Binding Affinities of Human Fc mAbs (H4H) at 37° C.
Binding at 37° C. - mAb Capture Format

|  | Analyte | ka (Ms$^{-1}$) | kd (s$^{-1}$) | $K_D$ (Molar) | T½ (min) |
|---|---|---|---|---|---|
| H4H6311P | human big-ET-1 | 1.92E+04 | 2.92E−04 | 1.52E−08 | 40 |
|  | mouse big-ET-1 | NB | NB | NB | NB |
| H4H6316P | human big-ET-1 | 2.88E+04 | 4.28E−04 | 1.48E−08 | 27 |
|  | mouse big-ET-1 | NB | NB | NB | NB |
| H4H6317P | human big-ET-1 | 3.67E+04 | 1.99E−04 | 5.42E−09 | 58 |
|  | mouse big-ET-1 | NB | NB | NB | NB |
| H4H6323P | human big-ET-1 | 5.65E+05 | 5.69E−03 | 1.01E−08 | 2 |
|  | mouse big-ET-1 | 5.80E+05 | 1.92E−02 | 3.29E−08 | 0.6 |
| H4H6327P2 | human big-ET-1 | 2.59E+05 | 3.01E−03 | 1.17E−08 | 4 |
|  | mouse big-ET-1 | 2.82E+05 | 3.13E−03 | 1.11E−08 | 4 |
| H4H6328P | human big-ET-1 | 1.58E+05 | 1.00E−06 | 6.34E−12 | 11550 |
|  | mouse big-ET-1 | NB | NB | NB | NB |
| H4H6329P | human big-ET-1 | 5.95E+05 | 1.76E−04 | 2.97E−10 | 65 |
|  | mouse big-ET-1 | 1.16E+04 | 2.23E−04 | 1.90E−08 | 52 |
| H4H6330P | human big-ET-1 | 1.42E+06 | 3.24E−02 | 2.29E−08 | 0.4 |
|  | mouse big-ET-1 | 1.50E+06 | 7.20E−02 | 5.00E−08 | 0.2 |
| H4H6332P | human big-ET-1 | 1.45E+06 | 4.29E−02 | 2.95E−08 | 0.3 |
|  | mouse big-ET-1 | 2.00E+06 | 1.96E−01 | 1.00E−07 | 0.1 |
| H4H6334P | human big-ET-1 | 2.02E+06 | 8.68E−05 | 4.30E−11 | 133 |
|  | mouse big-ET-1 | 7.90E+03 | 4.56E−04 | 5.80E−08 | 25 |
| H4H6334P2 | human big-ET-1 | 1.55E+05 | 3.49E−02 | 2.25E−07 | 0.3 |
|  | mouse big-ET-1 | ND | ND | ND | ND |
| H4H6335P | human big-ET-1 | 8.18E+05 | 4.37E−03 | 5.34E−09 | 3 |
|  | mouse big-ET-1 | NB | NB | NB | NB |
| H4H6337P | human big-ET-1 | 2.71E+06 | 4.91E−02 | 1.81E−08 | 0.2 |
|  | mouse big-ET-1 | 8.46E+05 | 1.62E−01 | 1.91E−07 | 0.1 |
| H4H6338P | human big-ET-1 | 4.54E+05 | 1.20E−01 | 2.65E−07 | 0.1 |
|  | mouse big-ET-1 | 1.90E+05 | 8.85E−01 | 4.66E−06 | 0.01 |
| H4H6340P | human big-ET-1 | 2.30E+06 | 2.49E−02 | 1.10E−08 | 0.5 |
|  | mouse big-ET-1 | 1.30E+06 | 6.03E−02 | 4.70E−08 | 0.2 |
| H4H6343P | human big-ET-1 | 1.61E+06 | 1.80E−02 | 1.12E−08 | 0.6 |
|  | mouse big-ET-1 | 1.80E+06 | 4.53E−02 | 2.52E−08 | 0.3 |
| H4H6345P | human big-ET-1 | 6.63E+05 | 5.80E−02 | 8.74E−08 | 0.2 |
|  | mouse big-ET-1 | 1.50E+06 | 9.74E−02 | 6.50E−08 | 0.1 |
| H4H6347P | human big-ET-1 | 1.81E+06 | 2.39E−02 | 1.32E−08 | 0.5 |
|  | mouse big-ET-1 | 3.10E+06 | 4.14E−02 | 1.30E−08 | 0.3 |

TABLE 3-continued

Biacore Binding Affinities of Human Fc mAbs (H4H) at 37° C.
Binding at 37° C. - mAb Capture Format

|  | Analyte | ka (Ms$^{-1}$) | kd (s$^{-1}$) | K$_D$ (Molar) | T½ (min) |
|---|---|---|---|---|---|
| H4H6353P | human big-ET-1 | 1.14E+06 | 1.16E−03 | 1.02E−09 | 10 |
|  | mouse big-ET-1 | 2.90E+03 | 2.36E−03 | 8.00E−07 | 5 |
| H4H6490N2 | human big-ET-1 | ND | ND | ND | ND |
|  | mouse big-ET-1 | ND | ND | ND | ND |
| H4H6492N2 | human big-ET-1 | 4.24E+05 | 2.97E−02 | 7.00E−08 | 0.4 |
|  | mouse big-ET-1 | ND | ND | ND | ND |
| H4H6495N | human big-ET-1 | 6.06E+05 | 3.99E−02 | 6.59E−08 | 0.3 |
|  | mouse big-ET-1 | ND | ND | ND | ND |

NB: No Binding; ND: Not Determined

As shown in Tables 2 and 3, several of the exemplary antibodies bound both human big-ET-1 (SEQ ID NO:434) and mouse big-ET-1 (SEQ ID NO:437). However, many of the exemplary antibodies tested in this Example exhibited preferential binding to human big-ET-1 over mouse big-ET-1. For example, antibodies H2M6490N, H1M6492N, H1M6494N, H2M6495N, H4H6311P, H4H6316P, H4H6317P, H4H6328P and H4H6335P each demonstrated high affinity binding to human big-ET-1 but did not show any binding to mouse big-ET-1 under the test conditions used in this Example. Antibodies H2M6495N, H4H6328P and H4H6334P each exhibited very high binding affinities to human big-ET-1 with K$_D$ values less than 50 pM.

Significantly, none of the antibodies of the present invention bound human small-ET-1 (SEQ ID NO:435).

Example 4: Anti-Big-ET-1 Antibodies of the Invention Block ECE1-Mediated Cleavage of Big-ET-1 In Vitro To determine if exemplary anti-big-ET-1 antibodies of the invention were able to block endothelin-converting enzyme-1 (ECE-1)-mediated cleavage of mouse and/or human big-ET-1, a NFAT luciferase reporter assay was utilized. Briefly, HEK293 cell lines were generated to stably express full-length human endothelin receptor type A (ETaR) along with a luciferase reporter element [NFAT (4x)-luciferase]. A single clone was isolated and maintained in 10% FBS, DMEM, NEAA, Pen/Strep, and 500 μg/ml G418 and 100 μg/ml hygromycin B.

To determine potency of inhibition, antibodies (100 nM to 0.002 nM) were incubated (1 hr; 25° C.) with either 10 nM human big-ET-1 (SEQ ID NO:434) or 20 nM mouse big-ET-1 (SEQ ID NO:437) followed by addition of 3 nM human or 5 nM mouse ECE-1, respectively. Both human and mouse big-ET-1 blocking experiments were allowed to incubate (37° C.; 5% CO$_2$) overnight. The next morning these solutions were added to the 293/ETaR/NFAT-Luc cells (20,000 cells/well) and luciferase activity was detected after 5.5 hrs (37° C.; 5% CO$_2$) using a Victor X plate reader (Perkin Elmer). The amount of luciferase activity observed under these conditions is a proportional representation of the amount of small-ET-1 generated from cleavage of either mouse or human big-ET-1. (Small-ET-1 is identical between mouse and human.) Results are presented in Tables 4 and 5 (NB=non-blocking under conditions tested; NT=not tested).

TABLE 4

Blocking Potency of Selected Anti-Big-ET-1
Hybridoma mAbs (H1M and H2M) Against Human
ECE-1-Mediated Cleavage of Human Big-ET-1

| Antibody | Blocking IC$_{50}$(M) 10 nM hBig-ET-1 + 3 nM hECE1 [Trial 1] | Blocking IC$_{50}$(M) 10 nM hBig-ET-1 + 3 nM hECE1 [Trial 2] |
|---|---|---|
| H2M6486N | 7.60E−09 | NT |
| H2M6490N | 1.90E−09 | NT |
| H1M6492N | 1.50E−09 | NT |
| H1M6494N | 1.50E−09 | NT |
| H2M6495N | 4.30E−09 | NT |
| H2M6741N | NT | 1.50E−08 |
| Isotype Ctrl | NB | NB |

TABLE 5

Blocking Potency of Selected Anti-Big-ET-1
Human Fc mAbs (H4H) Against Human ECE-1-Mediated
Cleavage of Human and Mouse Big-ET-1

| Antibody | Blocking IC$_{50}$(M) 10 nM hBig-ET-1 + 3 nM hECE1 | Blocking IC$_{50}$(M) 20 nM mBig-ET-1 + 5 nM mECE1 |
|---|---|---|
| H4H6311P | NB | NT |
| H4H6316P | NB | >1.00E−7 |
| H4H6317P | NB | >1.00E−7 |
| H4H6323P | 7.60E−09 | 4.00E−09 |
| H4H6327P2 | 2.20E−09 | 3.70E−09 |
| H4H6328P | >1.0E−07 | >1.00E−7 |
| H4H6329P | 3.30E−09 | >1.00E−7 |
| H4H6330P | 1.70E−09 | 1.60E−09 |
| H4H6332P | 3.10E−09 | 1.20E−09 |
| H4H6334P | 6.80E−10 | >1.00E−7 |
| H4H6335P | 6.60E−09 | >1.00E−7 |
| H4H6337P | 4.10E−09 | 2.10E−09 |
| H4H6338P | 2.80E−08 | 8.90E−09 |
| H4H6340P | 2.10E−09 | 1.50E−09 |
| H4H6343P | 1.20E−09 | 8.20E−10 |
| H4H6345P | 1.20E−08 | 3.70E−09 |
| H4H6347P | 1.50E−09 | 1.00E−09 |
| H4H6353P | 1.80E−09 | >1.00E−7 |
| H4H6490N2 | NB | NB |
| H4H6492N2 | 4.17E−08 | NB |
| H4H6495N | 1.33E−08 | NB |
| Isotype Ctrl | NB | NB |

As seen in Table 4 several hybridoma antibodies of the invention substantially inhibited ECE-1-mediated cleavage of human big-ET-1 (IC$_{50}$ values<10 nM). Additionally, selected antibodies in the human IgG4 format displayed the ability to not only block human big-ET-1 cleavage (Table 5; column 2) but also mouse big-ET-1 cleavage (Table 5; column 3).

Example 5: Antibody Protection of Big-ET-1 Cleavage Assessed by MALDI-TOF

Matrix Assisted Laser Desorption Ionization Time of Flight (MALDI-TOF) mass spectrometry was used to determine if selected anti-big-ET-1 antibodies could block the conversion of human big-ET-1 (SEQ ID NO:434) or mouse big-ET-1 (SEQ ID NO:437) into its respective peptides in the presence of mouse endothelin converting enzyme 1 (ECE-1). Human big-ET-1 is specifically cleaved by mECE-1 at Trp-21/Val-22 forming both biologically active small-ET-1 (SEQ ID NO:435; MH$^+$ 2474) and a non-active C-term product (amino acids 22-38 of SEQ ID NO:434; MH$^+$ 1809). Mouse big-ET-1 is cleaved at Trp-21/Val-22 into small-ET-1 (SEQ ID NO:435; MH$^+$ 2474) and its non-active C-term product (amino acids 22-39 of SEQ ID NO:437; MH$^+$ 1875). The appearance or absence of these masses, in the presence of antibody, can be monitored by MALDI-TOF. In the example below, the presence or absence of the C-term products served as an indicator for big-ET-1 cleavage since these peptides ionize more efficiently than small-ET-1 (SEQ ID NO:435; MH$^+$ 2474), thereby yielding a more sensitive readout.

Briefly, human or mouse big-ET-1 (0.5 µM) was mixed with antibody (2.5 µM), in phosphate buffered saline (PBS), at a 1:5 molar ratio (big-ET-1:mAb). After a 1-hr incubation (25° C.), mouse ECE-1 (R&D Systems) was added at 40 nM and the solution was placed at 37° C. Aliquots for mass spectrometry analysis were taken at 0, 15, 30 and 60 minutes. Each aliquot was desalted via C18 Ziptip (Millipore) and analyzed in reflextron-positive mode using a Bruker Ultraflextreme MALDI-TOF instrument (Bruker Daltonics).

The detection of C-term product from the cleavage of human or mouse big-ET-1 in the presence of antibody is summarized in Table 6.

TABLE 6

Detection of C-term Peptide Product from Cleavage of Big-ET-1

| Antibody | Species of Big-ET-1 | Detection of C-term Peptide Product at Various Time Points | | | |
|---|---|---|---|---|---|
| | | 0 min | 15 min | 30 min | 60 min |
| H2M6490N | Human | − | − | − | − |
| Mouse Fc Ctrl | Human | − | + | + | + |
| H4H6334P | Human | − | − | − | − |
| | Mouse | − | + | + | + |
| H4H6327P2 | Human | − | − | − | − |
| | Mouse | − | − | − | − |
| Human Fc Ctrl | Human | − | + | + | + |
| | Mouse | − | + | + | + |

When antibody H2M6490N was incubated with human big-ET-1 and mouse ECE-1 no C-term product was detected (denoted by "−" in Table 6). In contrast the mouse Fc control antibody did not prevent cleavage of human big-ET-1, in the presence of mouse ECE-1, and thus C-term product was identified at all time points (denoted by "+" in Table 6) except for time zero. Similar results were obtained for antibody H4H6334P. However for H4H6327P2 it was evident that this antibody can prevent cleavage of both human and mouse big-ET-1 in the presence of mouse ECE-1, since no C-term product was detected. Therefore, this Example confirms that anti-big-ET-1 antibodies of the invention (e.g., H2M6490N) are able to block the enzymatic conversion of human big-ET-1 into its biologically active form small-ET-1 in vitro.

Example 6: An Anti-Big-ET-1 Antibody Blocks Small-ET-1-Mediated Increases in Mean Arterial Blood Pressure The purpose of this Example was to evaluate the ability of an exemplary anti-big-ET-1 antibody (H2M6490N) to block small-ET-1-mediated increases in arterial pressure. Mice that had been previously infused with either blocking anti-big-ET-1 antibody or isotype control were challenged with big-ET-1 peptide. Changes in arterial pressure stemming from either big-ET-1 endogenous conversion to small-ET-1, or having its conversion blocked by circulating anti-big-ET-1 antibody, were measured. To facilitate real time measurements of arterial pressure during these experiments, mice were catheterized using standard protocols.

Briefly, naïve Taconic C57BL/6 mice (8-10 weeks of age) were anesthetized with isoflurane and the skin overlying the carotid artery and jugular vein was cut. Both the right jugular vein and left carotid artery were isolated, taking care not to damage the Vagus nerve or other blood vessels. Using standard techniques, the jugular vein was retracted and a 32-gauge needle (bent at a 90° angle) was used to puncture the vein for insertion of a saline-filled jugular vein catheter. The left carotid artery was then isolated and a Millar Micro-Tip® catheter was introduced using standard protocols. During all procedures a temperature probe was used to monitor animal body temperature, which was kept around 36.5° C. using a Gaymar heated water circulating pad. The above procedures allowed real-time pressure measurements (systolic pressure, diastolic pressure, mean arterial pressure, and body temperature) to be recorded during all big ET-1 challenge experiments.

In the first study, 150 µg (~2 mg/kg; 1×10$^{-9}$ Moles) of H2M6490N or isotype control mAb was injected i.v. using the jugular vein port followed by a bolus of saline to flush the catheter. This caused a slight and transient drop in pressure that returned to baseline and established the T=0 for the experiment. Thirty minutes after antibody dosing, human big-ET-1 peptide (SEQ ID NO:434) was injected i.v. every 15 minutes until the mean arterial pressure significantly increased above baseline. Results are summarized in Table 7.

TABLE 7

Study 1 - Mean Arterial Pressure Changes After Big-ET-1 Challenge
(Injection of Big-ET-1 30 Min After IV Antibody Dosing)

| Time (min) | Cumulative Dose Human big-ET-1 (Moles) | Cumulative Dose Antibody (Moles) | Molar Ratio (mAb:Big-ET-1) | Mean Pressure Change (mmHg) Isotype Ctrl (n = 3)* | Mean Pressure Change (mmHg) H2M6490N (n = 3)* |
|---|---|---|---|---|---|
| 0 | 0.00E+00 | 1.00E−09 | — | 0 | 0 |
| 30 | 3.85E−11 | 1.00E−09 | 26.0 | 15.1 ± 4.8 | −0.6 ± 2.6 |
| 45 | 1.16E−10 | 1.00E−09 | 8.7 | 38.6 ± 14.0 | −1.0 ± 3.5 |
| 60 | 2.32E−10 | 1.00E−09 | 4.3 | 30.6 ± 6.4 | 4.0 ± 4.7 |
| 75 | 4.66E−10 | 1.00E−09 | 2.1 | 19.7 ± 5.0 | 18.2 ± 9.6 |
| 90 | 8.16E−10 | 1.00E−09 | 1.2 | −30.7 ± 18.5 | 32.5 ± 20.8 |
| 105 | 1.28E−09 | 1.00E−09 | 0.8 | — | 25.1 ± 8.3 |
| 120 | 1.87E−09 | 1.00E−09 | 0.5 | — | −15.4 ± 8.2 |

Table 7 demonstrates that injection of human big-ET-1 into mice that had received isotype control respond with significantly increased mean arterial pressure as would be expected when big-ET-1 is cleaved endogenously into the bioactive small-ET-1 peptide (SEQ ID NO:435). In contrast mice that received the exemplary anti-big-ET-1 blocking antibody H2M6490N maintained baseline mean arterial pressure until the amount of human big-ET-1 peptide approached the molar equivalent of antibody on board.

In a second experiment, the same experimental protocol was utilized except that H2M6490N (~2 mg/kg; 1×10$^{-9}$ Moles) was injected subcutaneously (s.c.) into the mice 24 hrs before challenge with human big-ET-1 peptide. Results of the second experiment are summarized in Table 8.

TABLE 8

Study 2 - Mean Arterial Pressure Changes After Big-ET-1 Challenge
(Injection of Big-ET-1 ~ 24 hr After SC Antibody Dosing)

| Time (min) | Cumulative Dose Human big-ET-1 (Moles) | Cumulative Dose Antibody (Moles) | Molar Ratio (mAb:Big-ET-1) | Mean Pressure Change (mmHg) Isotype Ctrl (n = 2) | Mean Pressure Change (mmHg) H2M6490N (n = 2) |
|---|---|---|---|---|---|
| 0 | 0.00E+00 | 1.00E−09 | — | 0 | 0 |
| 30 | 3.85E−11 | 1.00E−09 | 26.0 | 13.1 | 1.7 |
| 45 | 1.16E−10 | 1.00E−09 | 8.7 | 32.1 | 7.6 |
| 60 | 2.32E−10 | 1.00E−09 | 4.3 | 60.7 | 14.9 |
| 75 | 4.66E−10 | 1.00E−09 | 2.1 | 60.6 | 52.1 |
| 90 | 8.16E−10 | 1.00E−09 | 1.2 | 7.3 | 45.8 |
| 105 | 1.28E−09 | 1.00E−09 | 0.8 | — | 12.0 |

As illustrated in Table 8, the results obtained when mice were challenged with big-ET-1 24 hours after subcutaneous antibody administration were similar to the results observed when mice were challenged with big-ET-1 thirty minutes after intravenous antibody dosing (Table 7). Under both experimental conditions, mice pre-infused with anti-big-ET-1 antibody H2M6490N maintained normal arterial pressures longer than those mice that were treated with isotype control antibody.

These studies therefore show that administration of H2M6490N was effective in inhibiting endothelin-1-mediated elevation in arterial pressure in vivo. Administration of antibody 30 min or 24 hr prior to challenge with human big-ET-1 significantly reduced the arterial pressure response compared to control.

Example 7: Blocking/Prevention of Hypoxia-Induced Pulmonary Hypertension with Anti-Big-ET-1 Antibodies In this Example, the ability of anti-big-ET-1 antibody H4H6327P2 to block hypoxia-induced pulmonary hypertension in mouse was evaluated. Animals were dosed prior to and during hypoxic conditions with treatment (anti-big-ET-1 antibody H4H6327P2 or Bosentan) or control (antibody vehicle (50:50 PEG 400 (v/v)) or isotype control antibody) agents and evaluated using ultrasound images and measurements of ventricular pressures and cardiac hypertrophy, in comparison to control animals maintained under normoxic conditions.

Evaluation Materials and Methods

Ultrasound measurements were acquired using the following protocol. Mice were anesthetized, placed in a supine position on a heated platform (THM 100, Indus Instruments) and 2D imaging of the pulmonary infundibulum (B- and M-mode) was carried out using a Vevo 2100 ultrasound system (VisualSonics). Images were obtained from the parasternal short-axis view at the level of the aortic valve. Pulsed-wave Doppler measurements were obtained at the tip of the pulmonary valve leaflets once the scanhead was aligned for maximal laminar flow. In addition, M-mode recordings of the right ventricle were acquired at the short axis B-mode imaging plane to obtain right ventricular free-wall dynamics through the cardiac cycle.

Ultrasound data analysis, performed in a blinded manner, analyzed the following parameters: Diastolic and systolic right ventricular free-wall thickness (RVFW, short axis M-mode), pulmonary artery diameter at end-systole (short axis B-mode), and pulmonary artery flow (PA flow, PW Doppler). From these measurements, time-velocity integral of pulmonary flow, pulmonary artery cross-sectional area (PA CSA), and right ventricle cardiac output (RV CO) were calculated. Means and standard errors of the mean were calculated for measurements at each time point, for each treatment group. All measurements were averaged on 3 cardiac cycles. Right ventricular pressures at 21 days of hypoxia were recorded using the following protocol: Mice were anesthetized, placed in the supine position on a heated platform (Water-jacketed pad heated with a Gaymar heating pump) and an incision over the right common carotid artery and right jugular vein was made isolating the right jugular taking care not to damage the carotid artery and/or the Vagus nerve. A piece of 5-0 silk suture was placed under the isolated jugular vein to allow for retraction of the vessel cranially, then a 30-gauge need was used to introduce a hole into the distal segment of the jugular vein. A high-fidelity pressure catheter (SPR-1000, Mikro-Tip®, Millar Instruments, Inc.) was introduced into the jugular vein and advanced past the right atrium and into the right ventricle (RV). The catheter allowed for recording of heart rate and both diastolic and systolic pressures. Data were digitally acquired using a PowerLab 4/35 console (ADInstruments).

Right ventricular systolic pressure analysis was conducted using LabChart Pro software (ADInstruments) at approximately 60 second intervals of pressure tracing (following a 2 minute period of recording to allow for pressure stabilization). The parameters analyzed were RV diastolic and systolic pressures, heart rate and animal temperature. The RV systolic pressures reported were the differences in minimum and maximum systolic pressures (to account for difference in initial baseline RV pressure values).

Following completion of RV systolic pressure measurement, the anesthetized animal was euthanized and the thoracic cavity was opened and heart excised. The RV was carefully cut away from the left ventricle and septum (LV+S). Both pieces of heart were separately weighed using a microbalance to estimate extent of RV hypertrophy [RV/(LV+S); Fulton Index].

Experimental Procedure

Pulmonary hypertension was induced using a modified chamber (Biospherix, Ltd.) that allowed for handling and dosing of animals while maintaining a normobaric hypoxic atmosphere (10% $O_2$). C57BL/6 male mice (10-11 weeks old) were weighed and dosed continuously over a course of 23 days as outlined in Table 9. Bosentan and Vehicle were administered orally (PO); anti-big-ET-1 antibody H4H6327P2 and isotype control antibody were administered subcutaneously (SC). Body weights were consistent between groups over the course of this study. Bosentan, an orally active non-selective antagonist of endothelin receptor-A and -B, was used as a positive control while vehicle [50:50 PEG 400 (v/v)] and an irrelevant isotype-matched antibody served as a negative control. All procedures were approved by the Regeneron Institutional Animal Care and Use Committee (IACUC).

TABLE 9

Treatment Groups and Dosing Regimen for Mice in Hypoxia-Induced Pulmonary Hypertension Model

| Group | N | Treatment Condition | % $O_2$ | Dosing Strategy |
|---|---|---|---|---|
| Treatment and Dosing Groups | | | | |
| 1 | 6 | Normoxia | 21 | — |
| Pre-dosing prior to placement in hypoxia chamber (Days 1 & 2) | | | | |
| 2 | 8 | Vehicle (50:50 PEG 400) | 21 | 10 mg/kg PO 48 h, 24 h, 0 h |
| 3 | 9 | Bosentan | 21 | 300 mg/kg PO 48 h, 24 h, 0 h |
| 4 | 8 | Mab Isotype Ctrl | 21 | 25 mg/kg SC 48 h, 0 h |
| 5 | 9 | H4H6327P2 | 21 | 25 mg/kg SC 48 h, 0 h |
| Dosing during placement in hypoxia chamber (Days 3-23) | | | | |
| 2 | 8 | Vehicle (50:50 PEG 400) | 10 | 10 mg/kg PO SID |
| 3 | 9 | Bosentan | 10 | 300 mg/kg PO SID |
| 4 | 8 | Mab Isotype Ctrl | 10 | 25 mg/kg SC every 3 days |
| 5 | 9 | H4H6327P2 | 10 | 25 mg/kg SC every 3 days |

Non-invasive ultrasound scanning was performed to determine pulmonary artery cross-sectional area (PA CSA), right ventricle cardiac output (RV CO) and right ventricular free wall thickness (RVFW) on the $18^{th}$ day of hypoxia. Right ventricular diastolic and systolic pressures were acquired using a high-fidelity pressure catheter (Mikro-Tip®, Millar Instruments) in the right ventricle; in addition, right ventricular hypertrophy measurements (i.e., weight ratio of right ventricle-to-left ventricle+septum; Fulton Index) were measured at 21 days of hypoxia.

Results

Figure 2:
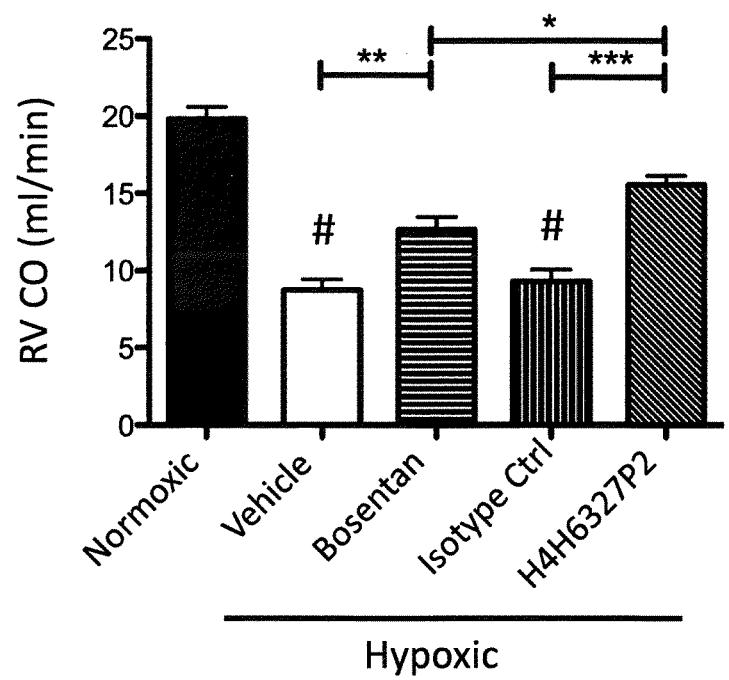
FIG. 2. Right Ventricular Cardiac Output (RV CO). H4H6327P2 preserves RV CO with greater efficacy than Bosentan. Reduction of RV CO during chronic hypoxia is associated with elevated vascular resistance in the pulmonary arteries. Greater preservation of RV CO in H4H6327P2-treated than Bosentan-treated animals suggest that H4H6327P2 may have greater efficacy in reducing RV afterload (i.e., pulmonary artery resistance). # designates $P<0.001$ vs. Normoxic. *, , * denote $P<0.05, 0.01$, and 0.001, respectively.
Figure 3:
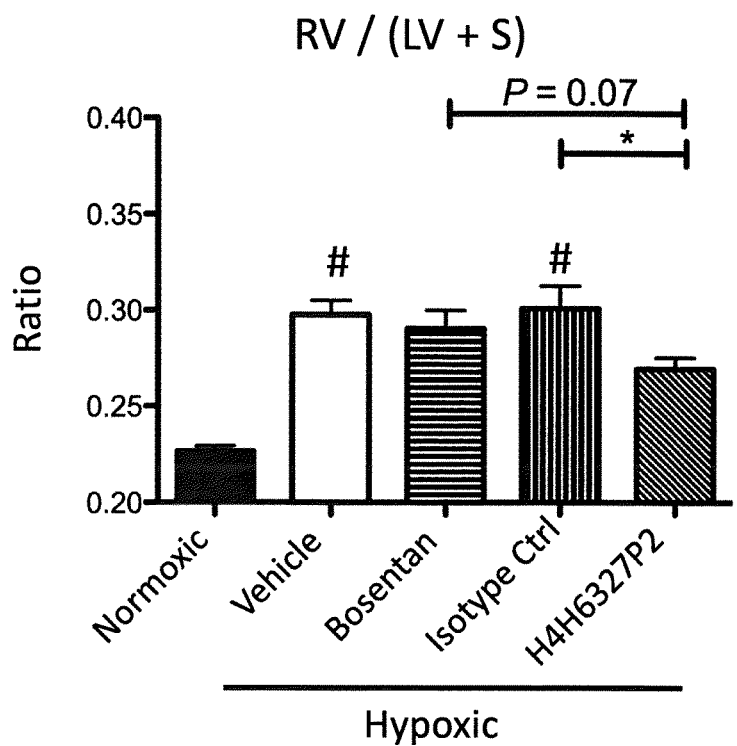
FIG. 3. Right Ventricle-to-Left Ventricle+Septum (RV/(LV+S)). H4H6327P2 treatment during chronic hypoxia significantly lessens the increase in RV/(LV+S) weight ratio. The greater the ratio is from baseline (i.e., Normoxic), the greater the extent of RV hypertrophy, which arises as a compensatory mechanism required for maintaining blood flow through the pulmonary arteries despite greater vascular resistance. The weight ratio from Bosentan treatment is similar to both Vehicle and Isotype Ctrl groups, indicating development of RV hypertrophy with exposure to chronic hypoxia. # denotes $P<0.001$ vs. Normoxic. * designates $P<0.05$.
Figure 4:
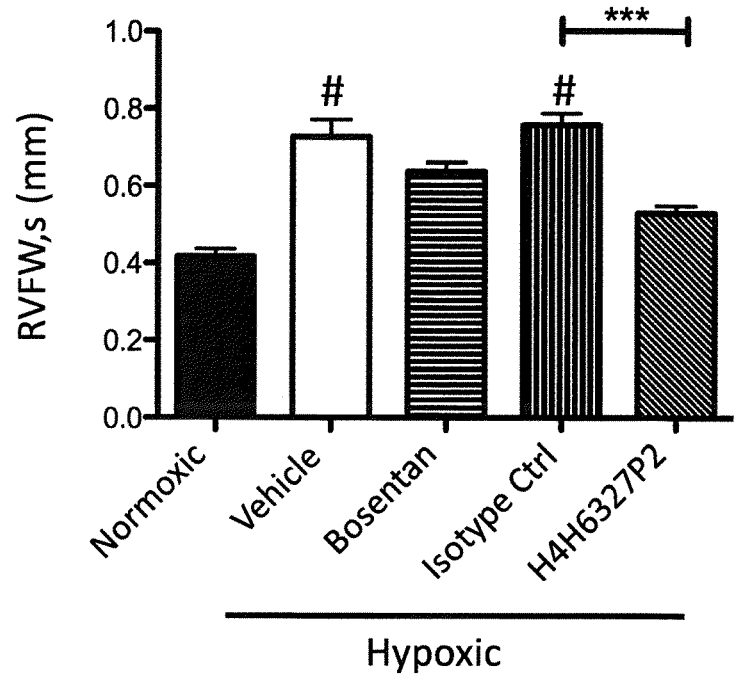
FIG. 4. Right Ventricular Free Wall Thickness, systole (RVFW,s). H4H6327P2 treatment significantly reduces RVFW thickening in chronic hypoxia. Wall thickening (i.e., hypertrophy) of the RV develops as a compensatory mechanism necessary to maintain blood flow though the pulmonary arteries despite greater vascular resistance. Greater RV wall thicknesses in Vehicle and Isotype Ctrl groups (relative to Normoxic) indicate development of RV hypertrophy; Bosentan treatment tends to reduce (not significant) the thickening of the RVFW in comparison to Vehicle treatment. # denotes $P<0.001$ vs. Normoxic. *** denotes $P<0.001$.

Treatment with anti-big-ET-1 antibody H4H6327P2 attenuated development of hypoxia-induced pulmonary hypertension in mice. Antibody-treated animals exhibited significantly (P 0.001) smaller reductions in measured PA CSA relative to isotype control-treated mice (FIG. 1), indicating less vasoconstriction and/or reduced pulmonary artery remodeling induced by exposure to chronic hypoxia. Bosentan, known to reduce symptoms associated with hypoxia-induced pulmonary hypertension in rodents, showed a similar yet reduced capacity to maintain basal PA CSA. Bosentan-treated animals showed a greater preservation of RV CO compared to the vehicle-treated group (FIG. 2). Animals treated with anti-big-ET-1 antibody showed statistically greater (P≤0.05) preservation of RV CO compared to both bosentan-treated and isotype-treated cohorts. Additionally, animals treated with anti-big-ET-1 antibody exhibited significantly less RV hypertrophy, as confirmed by both ultrasound (RVFW) and Fulton Index measurements (FIG. 3). Additionally, reduced RV hypertrophy was evidenced by significantly thinner right ventricular walls of the heart in anti-big-ET-1 antibody treated mice, relative to isotype control. (FIG. 4).

Conclusion

This study therefore demonstrates that anti-big-ET-1 antibodies of the present invention are effective in attenuating symptoms associated with hypoxia-induced pulmonary hypertension and surpassed the benchmark molecule Bosentan in some endpoints.

Example 8: Treatment of Hypoxia-Induced Pulmonary Hypertension with Anti-Big-ET-1 Antibodies In this Example, the ability of anti-big-ET-1 antibody H4H6327P2 to treat hypoxia-induced pulmonary hypertension in mouse was evaluated. Experimental group animals were subjected to hypoxic conditions for 21 days (Day 1-21) and dosed with H4H6327P2, Bosentan, or control isotype antibody starting on Day 14. At Day 21, animals were evaluated using ultrasound images and measurements of ventricular pressures and cardiac hypertrophy (see Evaluation Materials and Methods in Example 7) and compared to control animals (maintained under normoxic conditions, hypoxia for 14 days, or hypoxia for 14 days followed by normoxia for 7 days).

Experimental Procedure

Pulmonary hypertension was induced through exposure of a normobaric hypoxic atmosphere (10% $O_2$) via a modified chamber (Biospherix, Ltd.). C57BL/6 male mice (10-11 weeks old) were weighed and treated or treated and dosed over a course of 21 days as outlined in Table 10. Bosentan was administered orally (PO); anti-big-ET-1 antibody H4H6327P2 and isotype control antibody were administered subcutaneously (SC). Body weights were consistent between groups over the course of this study. Bosentan, an orally active non-selective antagonist of endothelin receptor-A and -B, was used as a positive control while an irrelevant isotype-matched antibody served as the negative control. All procedures were approved by the Regeneron Institutional Animal Care and Use Committee (IACUC).

TABLE 10

Treatment Groups and Dosing Regimen for Mice in Hypoxia-Induced Pulmonary Hypertension Model

| Group | N | Treatment Condition | % $O_2$ | Dosing Strategy |
|---|---|---|---|---|
| Treatment and Dosing Groups | | | | |
| 1 | 10 | Normoxia Placement in hypoxia chamber | 21 | — |
| 2 | 7 | Hypoxia for 14 days | 10 | — |
| 3 | 8 | Hypoxia for 14 days; normoxia for 7 days | 10/21 | — |
| Dosing after 14 days in hypoxia (Days 14-21) | | | | |
| 4 | 7 | Bosentan | 10 | 300 mg/kg PO SID |
| 5 | 6 | Mab Isotype Ctrl | 10 | 25 mg/kg SC every 3 days |
| 6 | 7 | H4H6327P2 | 10 | 25 mg/kg SC every 3 days |

Non-invasive ultrasound scanning was performed to determine pulmonary artery cross-sectional area (PA CSA), right ventricle cardiac output (RV CO) and right ventricular free wall thickness (RVFW) on the $21^{st}$ day of hypoxia. Right ventricular diastolic and systolic pressures were acquired using a high-fidelity pressure catheter (Mikro-Tip®, Millar Instruments) in the right ventricle; in addition, right ventricular hypertrophy measurements (i.e., weight ratio of right ventricle-to-left ventricle+septum; Fulton Index) were measured at 21 days of hypoxia.

Results

Figure 5:
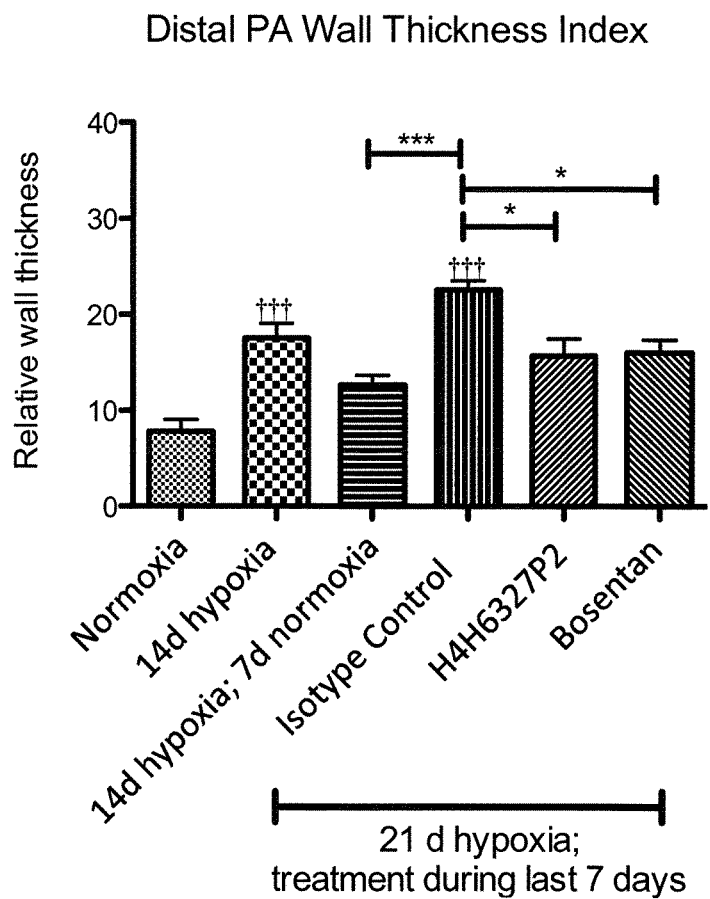
FIG. 5. Distal Pulmonary Arteriole Wall Thickening. Treatment with H4H6327P2 and Bosentan significantly reverses distal pulmonary arteriole wall thickening induced by chronic hypoxia, as shown by a smaller wall thickness-to-vessel diameter ratio (reflective of less smooth muscle layer proliferation and/or smooth muscle cell recruitment (i.e., less vessel remodeling)). Vessel wall thickening is reversible once animals are returned to normoxia for several days. ††† designates $P<0.001$ vs. Normoxia. *, *** denote $P<0.05, 0.001$. [text from original figure legend]
Figure 6:
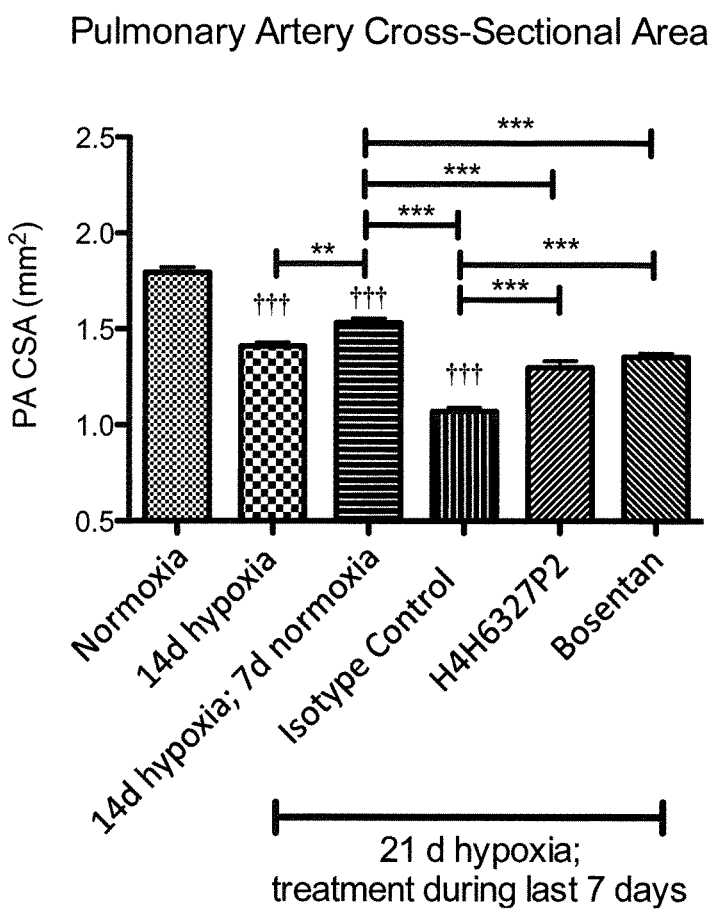
FIG. 6. Pulmonary Artery Cross-Sectional Area (PA CSA). H4H6327P2 and Bosentan significantly reverse the reduction in pulmonary artery cross-sectional area (PA CSA) induced by chronic hypoxia. Preservation of PA CSA from baseline (i.e., Normoxic) reflects less muscular wall thickening (i.e., vessel remodeling) and/or less vascular tone (i.e., vasoconstriction). Reduction in vessel cross-sectional area is reversible once animals are returned to normoxia for several days. ††† designates $P<0.001$ vs. Normoxia. *** denote $P<0.01, 0.001$.
Figure 7:
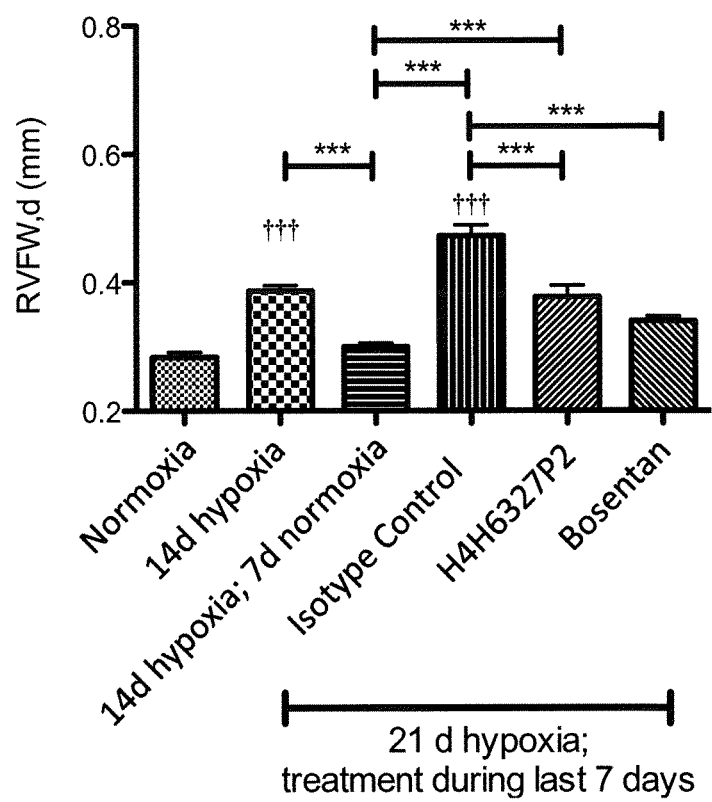
FIG. 7. Right Ventricular Free Wall (RVFW) Thickening. H4H6327P2 and Bosentan treatments significantly reverse right ventricular free wall (RVFW) thickening in chronic hypoxia. Wall thickening (ie, hypertrophy) of the RV develops as a compensatory mechanism necessary to maintain blood flow though the pulmonary arteries despite greater vascular resistance. Greater RV wall thicknesses in the isotype Ctrl group (relative to Normoxic) indicates development of RV hypertrophy. Ventricular wall thickening is reversible once animals are returned to normoxia for several days. ††† $P<0.001$ vs. Normoxia. *** denotes $P<0.001$.
Figure 8:
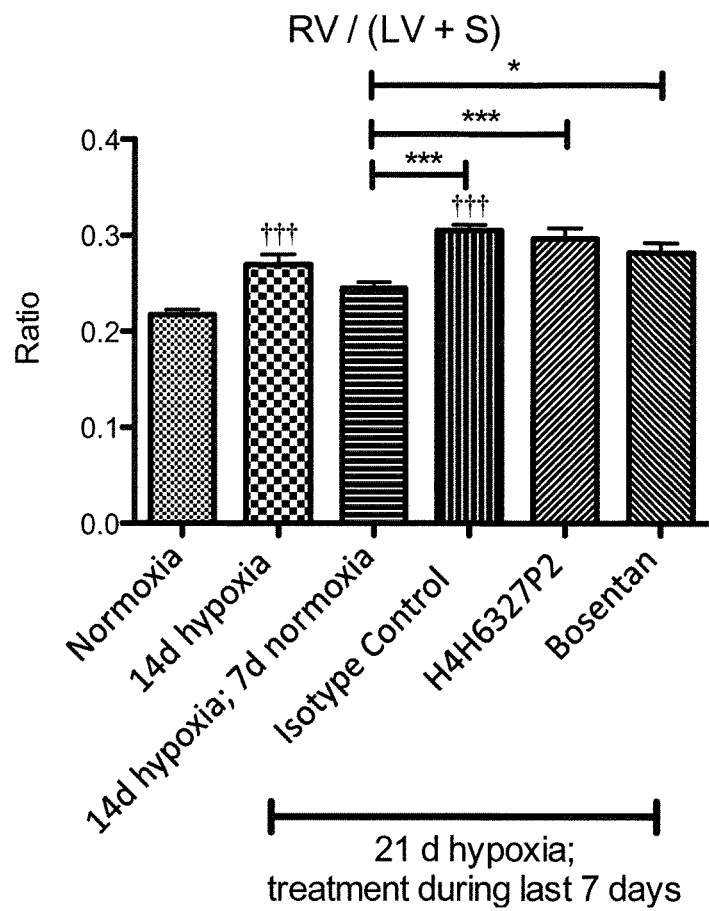
FIG. 8. Ratio of right ventricle-to-left ventricle+septum [RV/(LV+S)] weight. H4H6327P2 treatment during chronic hypoxia has little effect on the ratio of right ventricle-to-left ventricle+septum [RV/(LV+S)] weight. The greater the ratio from baseline (i.e., Normoxic), the greater the extent of RV hypertrophy, which arises as a compensatory mechanism required for maintaining blood flow through the pulmonary arteries despite greater vascular resistance. The weight ratio for H4H6327P2 and bosentan treatment is similar to Isotype Ctrl group, indicating development of RV hypertrophy with exposure to chronic hypoxia. ††\ denotes $P<0.001$ vs. Normoxia. *. *** designates $P<0.05, 0.001$.
Figure 9:
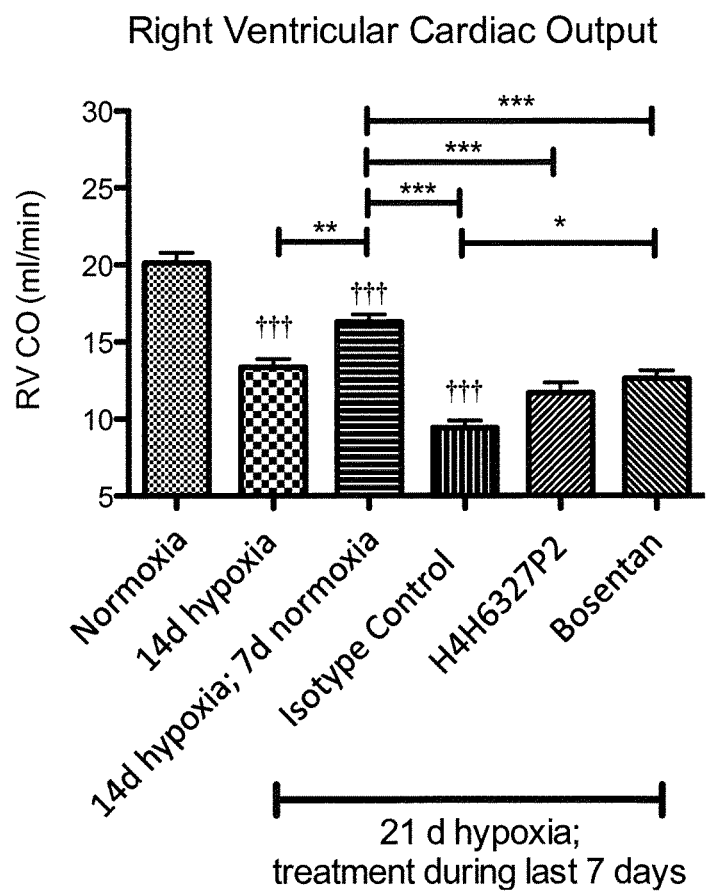
FIG. 9. Right Ventricular Cardiac Output (RV CO). H4H6327P2 tends to preserve right ventricular cardiac output (RV CO). Reduction of RV CO during chronic hypoxia is associated with elevated vascular resistance in the pulmonary arteries. Greater preservation of RV CO in bosentan-treated vs antibody-treated animals suggest that bosentan may have greater efficacy in reducing RV afterload (i.e., pulmonary artery resistance). RV CO is restored once animals are returned to normoxia for several days. ††\ designates $P<0.001$ vs. Normoxia. *, , * denote $P<0.05, 0.01, 0.001$.
Figure 10:
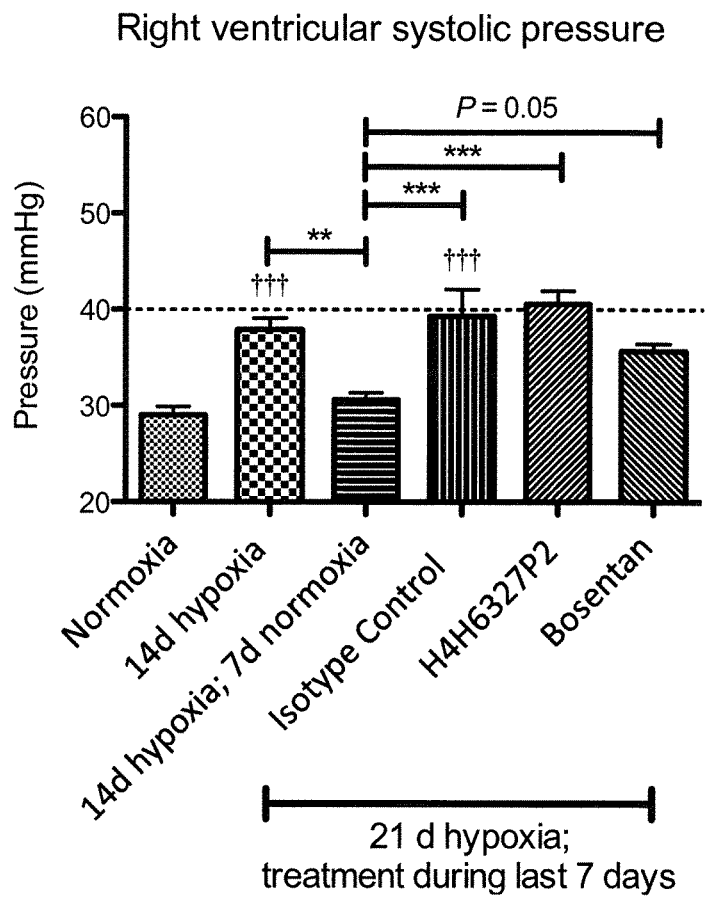
FIG. 10. Right Ventricular Systolic Pressure. H4H6327P2 treatment does not reduce right ventricular systolic pressure (RVSP). Elevated RVSP during chronic hypoxia is associated with increased vascular resistance in the pulmonary arteries; this is the pressure required to open the pulmonary valve. Bosentan tends to reduce the RVSP whereas anti-Big ET-1 antibody treatment does not. Elevation in RVSP is restored close to baseline when animals are returned to normoxia for several days. ††\ designates $P<0.001$ vs. Normoxia. , * denote $P<0.01, 0.001$.

Treatment with H4H6327P2 or bosentan attenuated distal pulmonary artery constriction and remodeling, including less vasoconstriction and vascular smooth muscle cell proliferation commonly associated with hypoxia-induced PH. Treatment with anti-big-ET-1 antibody H4H6327P2 significantly reduced chronic hypoxia-induced arteriole wall thickening compared with untreated or isotype-control cohorts (FIG. 5). Treatment with H4H6327P2 and bosentan also lessened lumen diameter loss, as evidenced by preservation of pulmonary artery cross sectional area (PA CSA) (FIG. 6), and attenuated right ventricular free wall (RVFW) thickening (FIG. 7). Anti-Big-ET-1 antibody treatment also preserved right ventricular cardiac output (RVCO), which is normally reduced in pulmonary hypertension due to elevated pulmonary artery vascular resistance, though to a lesser extent than bosentan (FIG. 9). However, anti-Big-ET-1 antibody treatment did not significantly reduce right ventricle hypertrophy, a compensatory mechanism which arises in order to maintain blood flow to pulmonary arteries (FIG. 8) or right ventricular systolic pressure (RSVP) (FIG. 10), both associated with increased vascular resistance due to pulmonary hypertension.

Conclusion

This study therefore demonstrates that anti-big-ET-1 antibodies of the present invention show the greatest efficacy in attenuating pulmonary hypertension induced vasculature remodeling, on par with bosentan, whereas bosentan treatment shows a greater effect in restoring measures of cardiac function.

Example 9: Reduction in Nocifensive Behaviors with Administration of Anti-Big ET-1 Antibodies In this example, the ability of anti-big ET-1 antibody H4H6327P2 to block big-ET-1 induced defensive responses to pain in the mouse was evaluated. H4H6327P2 blocks Endothelin Converting Enzyme (ECE) mediated cleavage of Big-ET-1 into the 21 amino acid biologically active ET-1. Exogenous administration of ET-1 in animals has been recorded to induce overt pain related behavior (nociception), such as abdominal writhing, flinching, biting or licking.

Experimental Procedure

Figure 11:
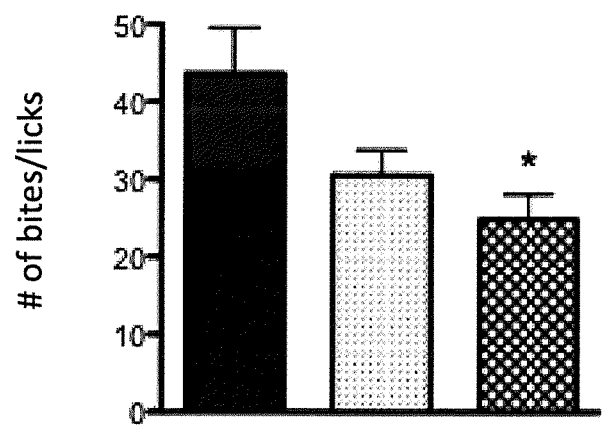
FIG. 11. Nocifensive Behaviors. Nocifensive behaviors are reduced in mice administered with anti-big ET-1 antibody H4H6327P2. 12 week old C57BL/6 male mice were separated into three experimental cohorts: a control group (n=6) receiving 30 mg/kg, of a non-big ET-1 binding isotype control antibody (Isotype) (solid bar); a low dose group (n=7) receiving 3 mg/kg of anti big-ET-1 antibody H4H6327P2 (gray bar); and a high dose group (n=7) receiving 30 mg/kg of H4H6327P2 (diagonal cross-hatch bar). * denotes $P<0.05$ vs. control.

In this study, 12 week old C57BL/6 male mice were separated into three experimental cohorts: a control group (n=6) receiving 30 mg/kg, of a non-big ET-1 binding isotype control antibody (Isotype); a low dose group (n=7) receiving 3 mg/kg of anti big-ET-1 antibody H4H6327P2; and a high dose group (n=7) receiving 30 mg/kg of H4H6327P2. All antibodies were administered subcutaneously. Approximately 48 hours after antibody dosing, all mice received a 2 ug (0.2 mg/ml) injection of big hET-1 peptide, solubilized in phosphate buffered saline, into the plantar side of the right hindpaw. Mice were immediately placed into clear cylinders and their nociceptive behaviors were video recorded for 60 minutes-post injection. An investigator blinded to cohort identity recorded the total number of right hindpaw licking/biting behaviors over the 60-minute test period. The data are reported as the cohort mean±SEM (FIG. 11).\

Results and Conclusion

Pre-treatment with H4H6327P2 significantly decreased big-hET-1 peptide-induced nocifensive behaviors over the 60-minute test period (p=0.0173 by repeated measures ANOVA). A dose-dependent effect was observed only in the 30 mg/kg dose group (p<0.05, Tukey). This example illustrates that administration of anti-Big-ET-1 antibodies may mitigate pain related behaviors by preventing the formation of the ET-1 by-product and subsequent receptor activation.

Example 10: Preventative Dosing with an Anti-Big ET-1 Antibody Attenuates Physiological Remodeling & Restores Lung Function in a Bleomycin-Induced Model of Pulmonary Fibrosis In this example, the ability of anti-Big-ET-1 antibody H4H6327P2 to act as a preventative treatment for bleomycin induced pulmonary fibrosis was evaluated.

Experimental Procedure

Bleomycin-induced lung injury was used to model pulmonary fibrosis in 10-week-old C57BL/6 male mice. Bleomycin sulfate was administered via a single oropharyngeal dose (3.2 U/kg (2.0 mg/kg) in a 2.0 ml/kg volume). Untreated control mice received a transoral instillation of sterile 0.9% saline (2.0 ml/kg). Bosentan, an orally active non-selective antagonist of endothelin receptor-A and -B, was used as a positive control for treatment, while vehicle and an irrelevant isotype matched antibody served as negative controls. Mice were allocated to treatment or control groups with dosing regimens as outlined in Table 11.

TABLE 11

Treatment Groups and Dosing Regimen for Mice in Bleomycin-Induced Pulmonary Fibrosis Model
Treatment and Dosing Groups (Days 0-20)

| Group | N | Bleomycin Dose | Treatment | Treatment Strategy |
|---|---|---|---|---|
| 1 | 10 | 0.9% saline; | PBS - 5% Glycerol | 5 ml/kg SC on days 0, 3, 6, 9, 12, 15 & 18 |
| 2 | 10 | 3.2 U/kg (2.0 mg/kg) Bleomycin; | PBS - 5% Glycerol | 5 ml/kg SC on days 0, 3, 6, 9, 12, 15 & 18 |
| 3 | 10 | 3.2 U/kg (2.0 mg/kg) Bleomycin; | Isotype Ctrl | 25 mg/kg SC at 5 ml/kg on days 0, 3, 6, 9, 12, 15 & 18 |
| 4 | 10 | 3.2 U/kg (2.0 mg/kg) Bleomycin; | H4H6327P2 | 25 mg/kg SC at 5 ml/kg on days 0, 3, 6, 9, 12, 15 & 18 |
| 5 | 10 | 3.2 U/kg (2.0 mg/kg) Bleomycin; | Bosentan | 300 mg/kg SID PO at 10 ml/kg volume on day 0 150 mg/kg BID PO at 10 ml/kg volume days 1-20 |

BID = bis in die/2x Daily administration, SID = 1x Daily administration, SC = Subcutaneous, PO = per os (oral)

Results

As a measure of treatment efficacy, right lung weights of animals in each cohort were measured 21 days post bleomycin exposure. Increase in lung weight is a commonly observed physiological effect of bleomycin-induced pulmonary fibrosis (Table 12; Group 1 vs. Group 2 & 3). Treatment with anti-Big-ET-1 antibody H4H6327P2 tended to lower lung wet weights, as well as the percentage of water-weight increase (edema) when compared to isotype control. However, only treatment with bosentan showed statistically significant reductions in wet lung weights.

TABLE 12

Outcome Parameters for Treatment Groups in Bleomycin-Induced Pulmonary Fibrosis Model

| Group | Treatment | Start Body Weight (g) AVG | End Body Weight (g) AVG | Wet Weight Rt. Lung (mg) AVG ± SEM | % Arterial Blood $O_2$ Saturation AVG ± SEM | Total Collagen Rt. Lung (ug) AVG ± SEM |
|---|---|---|---|---|---|---|
| 1 | Untreated Saline; 2.0 ml/kg | 25 | 27 | 95 ± 3 | 99 ± 0.2 | 279 ± 24 |
| 2 | Bleomycin* + Vehicle (PBS + 5% Glycerol) | 24 | 25 | 203 ± 13 | 85 ± 3 | 922 ± 91 |
| 3 | Bleomycin* + Isotype control (25 mg/kg) | 25 | 25 | 196 ± 18 | 84 ± 4 | 802 ± 115 |
| 4 | Bleomycin* + H4H6327P2 (25 mg/kg) | 25 | 26 | 158 ± 12 | 92 ± 2 | 613 ± 83 |
| 5 | Bleomycin* + Bosentan[#] (150 mg/kg B.I.D.) | 25 | 24 | 117 ± 6 | 93 ± 1 | 403 ± 38 |

*Bleomycin: Administered via a single oropharyngeal dose at 3.2 U/kg in a 2.0 ml/kg volume
B.I.D.: Bis In die (2x/day administration)

Conclusion

The effect of antibody or bosentan treatment on preserving lung function was also assessed. H4H6327P2 and bosentan both tended to restore arterial blood oxygen saturation closer to baseline levels 20 days post bleomycin administration, compared to vehicle or isotype control treated cohorts and also reduced collagen accumulation in the lung post bleomycin exposure.

Materials and Methods

Animal Handling Procedures:

Each cage was randomly assigned to a therapeutic treatment group so all mice in the cage received the same treatment. Initial average body weight for each treatment group was similar. Daily body weights were recorded throughout the study. Group body weight average and percent change were analyzed and graphed. Animals that exhibited body weight loss >25% or severe deterioration in health over the course of the study were euthanized.

Administration of Bleomycin:

Administration of bleomycin or saline was performed while animals were under anesthesia (isoflurane at a 3.5% to 2-liters/min oxygen flow rate). Sedated mice were placed on a 60-degree tilt board, head up with an elastic band around the incisors. A small cotton tip was used to roll tongue out of the mouth then forceps were used to hold tongue and to open the jaw. During a heavy inhalation, fluid was pipetted into the mouth. Tongue and jaw positions were maintained while mouse remained on the tilt board. Approximately 20 seconds elapsed after pipetting for fluid to disappear and "wheezing" to stop. After treatment instillation, mice were group-housed by treatment conditions (5 animals per cage) in disposable cages for 7 days because of excreted biohazard and then returned to home cages. Disposable cages differed from home cages only by use of a cage top bottle for water instead of use of Thoren rack watering system. All mice were housed in colony on 12 hr (7 am-7 pm) light-dark cycle.

Administration of Bosentan:

Bosentan was administered by oral gavage twice daily (9:30 am and 6:30 pm) during the week. The initial pretreatment dose and weekend day doses were administered as a single combined BID. As outlined in Table 11, Bosentan dosing continued daily through day 20 of study while antibodies and vehicle were subcutaneously dosed every 3 days through day 18.

Measurement of Pulmonary Function:

Pulmonary function was gauged by measuring arterial oxygen saturation using the Starr Life Sciences, MouseOx small animal vital signs monitor. Measurements were taken around the neck region following hair removal on Days 14 and 17. The MouseOx can monitor the cardio-pulmonary health and degree of lung injury by measuring the level of oxygen carried to the tissues on hemoglobin molecules in red blood cells. A throat collar sensor was used to measure arterial oxygen saturation via the carotid artery in conscious mice. Mice were lightly restrained by hand to confine subject to the cage top food hopper and to reduce movement. Software (MouseOx Ver. 6.3.12 with InstCal.) measures pulse distension, heart rate, Oxygen saturation, and breathing rate every second. Once a continuous 15 second block is recorded, the software calculates the average of the above parameters. Measurement time ranged from 1 to 3 minutes depending on mouse activity. An average arterial oxygen saturation for each treatment group was calculated and analyzed using one-way ANOVA with Bonferroni post-test comparisons of all treatment groups.

Terminal Procedures/Histology:

On Day 21, mice were administered a terminal dose of Ketamine/Xylazine (120 mg/kg/5 mg/kg IP, respectively). Upon sedation, the abdominal cavity was opened and blood for serum was collected by syringe via the inferior vena cava. The abdominal aorta was then severed. During exsanguination, the thoracic cavity was opened to expose the lungs. Suture was tied around the right bronchus above all right lung lobes. For all mice the entire right lung, consisting of the Superior, Middle, Inferior and the Post-Caval lobes was removed, weighed, flash frozen in liquid Nitrogen and then stored in −80 C freezer for collagen measurement. Before collagen extraction, right lung lobes were dried in a desiccator and re-weighed. Wet and dry lung weights and wet wt. to dry wt. ratios were calculated for each treatment group. Lungs were homogenized in a Pepsin-acetic acid solution to extract soluble collagen. Sircol collagen assay from Biocolor was used to quantify soluble collagen per right lung and collagen per mg of wet and dry lung tissue.

For each treatment group, use of the left lung lobe was randomly split between histology and Microarray. For histological subjects, an incision was made on the ventral neck, Submaxillary glands were separated and the trachea was exposed by cutting the surrounding muscle fibers. Suture was lightly tied around the trachea, distal to the mouth. A small hole was then cut into the trachea above the suture, proximal to the mouth. A 22 g blunt needle, affixed to a tube and 250 ml aspirator filled with 10% NBF, was inserted into the hole. Suture knot was then tightened around the threaded trachea to seal opening and hold needle in place. At 25 cm height, the left lung was inflated by gravity force for about 30-60 seconds. After inflation, needle was removed and suture was firmly tightened. The left lung still attached to bronchi, the trachea, thymus, esophagus and heart were removed as 1 piece and stored in formalin. After fixation, left lung lobe was isolated and removed for histological processing (Sirius Red, Masson's trichrome and H&E). Microarray designated mice had the left lung lobe placed in RNA-Later without inflation at room temperature for 24 hours and then placed in −20° C. freezer until gene sequencing.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated human antibody or antigen-binding fragment thereof that specifically binds human big-endothelin-1 (big-ET-1) (SEQ ID NO:434), and does not bind small-endothelin-1 (small-ET-1) (SEQ ID NO:435), wherein the antibody or antigen-binding fragment thereof blocks cleavage of big-ET-1 by endothelin-converting enzyme-1 (ECE-1) and comprises the complementarity determining regions (CDRs) of a heavy chain variable region (HCVR) having the amino acid sequence selected from the group consisting of SEQ ID NO:2, 18, 34, 50, 66, 146, 162, 194, 210, 226, 242, 258, 274, 290, 322, 338, 370, and 386, and the CDRs of a light chain variable region (LCVR) having the amino acid sequence selected from the group consisting of SEQ ID NO:10, 26, 42, 58, 74, 154, 170, 202, 218, 234, 250, 266, 282, 298, 330, 346, 378, and 394.

2. The isolated antibody or antigen-binding fragment of claim 1, wherein the antibody or antigen-binding fragment thereof binds human big-ET-1 (SEQ ID NO:434) but not mouse big-ET-1.

3. The isolated antibody or antigen-binding fragment of claim 1, wherein the antibody or antigen-binding fragment thereof binds human big-ET-1 (SEQ ID NO:434) and mouse big-ET-1.

4. The isolated antibody or antigen-binding fragment of claim 1, wherein said antibody or antigen-binding fragment thereof comprises heavy and light chain CDRs of the HCVR/LCVR sequence pair selected from the group consisting of SEQ ID NOs:2/10, 18/26, 34/42, 50/58, 66/74, 146/154, 162/170, 194/202, 210/218, 226/234, 242/250, 258/266, 274/282, 290/298, 322/330, 338/346, 370/378, and 386/394.

5. The isolated antibody or antigen-binding fragment of claim 4, wherein the antibody or antigen-binding fragment thereof comprises HCDR1-HCDR2-HCDR3-LCDR1-LCDR2-LCDR3 domains, respectively, selected from the group consisting of SEQ ID NOs: 4-6-8-12-14-16; 20-22-24-28-30-32; 36-38-40-44-46-48; 52-54-56-60-62-64; 68-70-72-76-78-80; 148-150-152-156-158-160; 164-166-168-172-174-176; 196-198-200-204-206-208; 212-214-216-220-222-224; 228-230-232-236-238-240; 244-246-248-252-254-256; 260-262-264-268-270-272; 276-278-280-284-286-288; 292-294-296-300-302-304; 324-326-328-332-334-336; 340-342-344-348-350-352; 372-374-376-380-382-384; and 388-390-392-396-398-400.

6. The isolated antibody or antigen-binding fragment of claim 5, wherein said antibody or antigen-binding fragment thereof comprises the HCVR/LCVR amino acid sequence pair selected from the group consisting of SEQ ID NOs:2/10, 18/26, 34/42, 50/58, 66/74, 146/154, 162/170, 194/202, 210/218, 226/234, 242/250, 258/266, 274/282, 290/298, 322/330, 338/346, 370/378, and 386/394.

7. A pharmaceutical composition comprising the antibody or antigen-binding fragment of claim 6 and a pharmaceutically acceptable carrier or diluent.

8. A pharmaceutical composition comprising the antibody or antigen-binding fragment of claim 1 and a pharmaceutically acceptable carrier or diluent.

9. The isolated antibody or antigen-binding fragment of claim 1, wherein the antibody or antigen-binding fragment thereof comprises heavy and light chain CDRs of the HCVR/LCVR sequence pair of SEQ ID NOs: 242/250.

10. The isolated antibody or antigen-binding fragment of claim 9, wherein the antibody or antigen-binding fragment thereof comprises HCDR1-HCDR2-HCDR3-LCDR1-LCDR2-LCDR3 domains, respectively, of SEQ ID NOs: 244-246-248-252-254-256.

11. The isolated antibody or antigen-binding fragment of claim 10, wherein the antibody or antigen-binding fragment thereof comprises the HCVR/LCVR amino acid sequence pair of SEQ ID NOs: 242/250.

12. A pharmaceutical composition comprising the antibody or antigen-binding fragment of claim 11 and a pharmaceutically acceptable carrier or diluent.

13. The isolated antibody or antigen-binding fragment of claim 1, wherein the antibody or antigen-binding fragment thereof comprises heavy and light chain CDRs of the HCVR/LCVR sequence pair of SEQ ID NOs: 18/26.

14. The isolated antibody or antigen-binding fragment of claim 13, wherein the antibody or antigen-binding fragment thereof comprises HCDR1-HCDR2-HCDR3-LCDR1-LCDR2-LCDR3 domains, respectively, of SEQ ID NOs: 20-22-24-28-30-32.

15. The isolated antibody or antigen-binding fragment of claim 14, wherein the antibody or antigen-binding fragment thereof comprises the HCVR/LCVR amino acid sequence pair of SEQ ID NOs: 18/26.

16. A pharmaceutical composition comprising the antibody or antigen-binding fragment of claim 15 and a pharmaceutically acceptable carrier or diluent.

17. The isolated antibody or antigen-binding fragment of claim 1, wherein the antibody or antigen-binding fragment thereof comprises heavy and light chain CDRs of the HCVR/LCVR sequence pair of SEQ ID NOs: 162/170.

18. The isolated antibody or antigen-binding fragment of claim 17, wherein the antibody or antigen-binding fragment thereof comprises HCDR1-HCDR2-HCDR3-LCDR1-LCDR2-LCDR3 domains, respectively, of SEQ ID NOs: 164-166-168-172-174-176.

19. The isolated antibody or antigen-binding fragment of claim 18, wherein the antibody or antigen-binding fragment thereof comprises the HCVR/LCVR amino acid sequence pair of SEQ ID NOs: 162/170.

20. A pharmaceutical composition comprising the antibody or antigen-binding fragment of claim 19 and a pharmaceutically acceptable carrier or diluent.

* * * * *